United States Patent
O'Neil et al.

(10) Patent No.: US 7,833,531 B2
(45) Date of Patent: Nov. 16, 2010

(54) METHOD FOR TREATING INSULIN SENSITIVITY BY LONG-ACTING GLP-1 RECEPTOR MIMETIBODY AGONISTS

(75) Inventors: Karyn T. O'Neil, Media, PA (US); Kristen Picha, Malvern, PA (US); Vedrana Stojanovic-Susulic, Princeton Junction, NJ (US)

(73) Assignee: Centocor, Inc., Malvem, PA (US)

( * ) Notice: Subject to any disclaimer, the term of this patent is extended or adjusted under 35 U.S.C. 154(b) by 193 days.

(21) Appl. No.: 11/962,214

(22) Filed: Dec. 21, 2007

(65) Prior Publication Data

US 2009/0098108 A1    Apr. 16, 2009

Related U.S. Application Data

(60) Provisional application No. 60/871,142, filed on Dec. 21, 2006.

(51) Int. Cl.
*A61K 39/00* (2006.01)
*A61K 38/00* (2006.01)
*C07K 16/00* (2006.01)

(52) U.S. Cl. ................. 424/178.1; 530/308; 530/387.1; 514/2

(58) Field of Classification Search ........................ None
See application file for complete search history.

(56) References Cited

U.S. PATENT DOCUMENTS

| | | |
|---|---|---|
| 3,773,919 A | 11/1973 | Boswell et al. |
| 4,239,754 A | 12/1980 | Sache et al. |
| 4,309,989 A | 1/1982 | Fahim |
| 4,399,216 A | 8/1983 | Axel et al. |
| 4,634,665 A | 1/1987 | Axel et al. |
| 4,656,134 A | 4/1987 | Ringold |
| 4,668,218 A | 5/1987 | Virtanen |
| 4,767,402 A | 8/1988 | Kost et al. |
| 4,873,316 A | 10/1989 | Meade et al. |
| 4,925,673 A | 5/1990 | Steiner et al. |
| 4,946,778 A | 8/1990 | Ladner et al. |
| 4,956,288 A | 9/1990 | Barsoum |
| 5,118,666 A | 6/1992 | Habener |
| 5,122,464 A | 6/1992 | Wilson et al. |
| 5,149,636 A | 9/1992 | Axel et al. |
| 5,179,017 A | 1/1993 | Axel et al. |
| 5,266,491 A | 11/1993 | Nagata et al. |
| 5,304,489 A | 4/1994 | Rosen |
| 5,404,871 A | 4/1995 | Goodman et al. |
| 5,458,135 A | 10/1995 | Patton et al. |
| 5,514,670 A | 5/1996 | Friedman et al. |
| 5,545,618 A | 8/1996 | Buckley et al. |
| 5,565,362 A | 10/1996 | Rosen |
| 5,770,222 A | 6/1998 | Unger et al. |
| 5,770,359 A | 6/1998 | Wilson et al. |
| 5,827,690 A | 10/1998 | Meade et al. |
| 5,827,739 A | 10/1998 | Wilson et al. |
| 5,839,446 A | 11/1998 | Waner et al. |
| 5,849,695 A | 12/1998 | Cohen et al. |
| 5,849,992 A | 12/1998 | Meade et al. |
| 5,851,198 A | 12/1998 | Castellano et al. |
| 5,871,753 A | 2/1999 | Crabtree et al. |
| 5,879,681 A | 3/1999 | Leone-Bay et al. |
| 5,977,071 A | 11/1999 | Galloway et al. |
| 5,994,616 A | 11/1999 | Rosen |
| 6,730,690 B2 * | 5/2004 | Olson et al. .................. 514/383 |

FOREIGN PATENT DOCUMENTS

| | | |
|---|---|---|
| EP | 237507 A1 | 9/1987 |
| WO | WO 92/16221 A1 | 10/1992 |
| WO | WO 94/06498 A1 | 3/1994 |
| WO | WO 94/08552 A2 | 4/1994 |
| WO | WO 94/16970 A1 | 8/1994 |
| WO | WO 97/22376 A1 | 6/1997 |
| WO | WO 97/25086 A2 | 7/1997 |
| WO | WO 98/35888 A1 | 8/1998 |
| WO | WO 98/53847 A1 | 12/1998 |
| WO | WO 01/66135 A1 | 9/2001 |
| WO | WO 2005/005604 A2 | 1/2005 |
| WO | WO 2005/097175 A2 | 10/2005 |
| WO | WO 2007/046834 A2 | 4/2007 |
| WO | WO 2007/076319 A2 | 7/2007 |
| WO | WO 2007/081302 A2 | 7/2007 |

OTHER PUBLICATIONS

Wells, Biochemistry 29:8509-8517, 1990.*
The Merck Manual, 17th ed., Merck Research Laboratories, Merck and Co., Whitehouse Station, NJ (1999).

(Continued)

*Primary Examiner*—Robert Landsman
*Assistant Examiner*—Gyan Chandra
(74) *Attorney, Agent, or Firm*—Kirk Baumeister

(57) ABSTRACT

The present invention provides to at least one novel human GLP-1 receptor agonist, or specified portion or variant, including isolated nucleic acids that encode at least one GLP-1 receptor agonist, or specified portion or variant, GLP-1 receptor agonist, or specified portion or variants, vectors, host cells, transgenic animals or plants, and methods of making and using thereof, including the use of long acting GLP-1 receptor agonists to improve insulin sensitivity or lipid profiles in obesity and related therapeutic and/or diagnostic compositions, methods and devices.

8 Claims, No Drawings

OTHER PUBLICATIONS

Sarmay et al. Molec. Immunol. 29 (5): 633-9 (1992).
Adelhorst, et al., *J. Biol. Chem.* 269:6275 (1994).
Elliott et al., *Lancet* 344:1125-1127 (1994).
Ausubel, et al., ed., Current Protocols in Molecular Biology, John Wiley & Sons, Inc., NY, NY (1987-2005).
Sambrook, et al., Molecular Cloning: A Laboratory Manual, 2nd Edition, Cold Spring Harbor, NY (1989).
Harlow and Lane, Antibodies, a Laboratory Manual, Cold Spring Harbor, NY (1989).
Colligan, et al., eds., Current Protocols in Immunology, John Wiley & Sons, Inc., NY (1994-2005).
Colligan et al., Current Protocols in Protein Science, John Wiley & Sons, NY, NY, (1997-2005).
Bird, R.E. et al., *Science*, 242: 423-426 (1988).
Cramer et al., Curr. Top. Microbol. Immunol. 240:95-118 (1999).
Hood et al., Adv. Exp. Med. Biol. 464:127-147 (1999).
Conrad et al., Plant Mol. Biol. 38:101-109 (1998).
Fischer et al., Biotechnol. Appl. Biochem. 30:99-108 (Oct. 1999).
Ma et al., Trends Biotechnol. 13:522-7 (1995).
Ma et al., Plant Physiol. 109:341-6 (1995).
Whitelam et al., Biochem. Soc. Trans. 22:940-944 (1994).
Berzofsky, et al., "Antibody-Antigen Interactions," *In Fundamental Immunology*, Paul, W. E., Ed., Raven Press: New York, NY (1984).
Kuby, Janis *Immunology*, W. H. Freeman and Company: New York, NY (1992).
Sprague, et al., J. Virol. 45:773-781 (1983).
Katsube, Y., et al., *Int J Mol. Med*, 1(5):863-868 (1998).
Alberts, B., et al., Molecular Biology of The Cell, Third Ed., Garland Publishing, Inc., New York, 1994.
Cunningham and Wells, Science 244:1081-1085 (1989).
Smith, et al., J. Mol. Biol. 224:899-904 (1992).
de Vos, et al., Science 255:306-312 (1992).
Hermanson, G. T., *Bioconjugate Techniques*, Academic Press: San Diego, CA (1996).
Fisch et al., *Bioconjugate Chem.*, 3:147-153 (1992).
Werlen et al., *Bioconjugate Chem.*, 5:411-417 (1994).
Kumaran et al., *Protein Sci.* 6(10):2233-2241 (1997).
Itoh et al., *Bioorg. Chem.*, 24(1): 59-68 (1996).
Capellas et al., *Biotechnol. Bioeng.*, 56(4):456-463 (1997).
Nursing 2001 Handbook of Drugs, 21st edition, Springhouse Corp., Springhouse, PA, 2001.
Health Professional's Drug Guide 2001, ed., Shannon, Wilson, Stang, Prentice-Hall, Inc, Upper Saddle River, NJ.
Gennaro, Ed., *Remington's Pharmaceutical Sciences*, 18th Edition, Mack Publishing Co. (Easton, PA) 1990.
"Remington: The Science & Practice of Pharmacy", 19th ed., Williams & Williams, (1995).
"Physician's Desk Reference", 52nd ed., Medical Economics, Montvale, NJ (1998).
Merck Manual, 12th-17th Editions, Merck & Company, Rahway, NJ (1972, 1977, 1982, 1987, 1992, 1999), Pharmacotherapy Handbook, Wells et al., eds., Second Edition, Appleton and Lange, Stamford, Conn. (1998, 2001).
Wells et al., eds., Pharmacotherapy Handbook, 2nd Edition, Appleton and Lange, Stamford, CT (2000).
PDR Pharmacopoeia, Tarascon Pocket Pharmacopoeia 2000, Deluxe Edition, Tarascon Publishing, Loma Linda, CA (2000).
Junginger, et al., Visualization of Drug Transport Across Human Skin and the Influence of Penetration Enhancers, *Drug Permeation Enhancement*, Hsieh, D. S., Eds., pp. 59-90 Marcel Dekker, Inc. New York 1994.
"Sustained and Controlled Release Drug Delivery Systems", J. R. Robinson ed., Marcel Dekker, Inc., N. Y., 1978.
Murphy, et al., Biochem. J. 227:277-279 (1991).
Bebbington, et al., Bio/Technology 10:169-175 (1992).
Cullen, et al., Molec. Cell. Biol. 5:438-447 (1985).
Boshart, et al., Cell 41:521-530 (1985).
F. W. Alt, et al., J. Biol. Chem. 253:1357-1370 (1978).
J. L. Hamlin and C. Ma, Biochem. et Biophys. Acta 1087(2):107-125 (1990).
M. J. Page and M. A. Sydenham, Biotechnology 9:64-68 (1991).
M. Gossen, and H. Bujard, Proc. Natl. Acad. Sci. USA 89: 5547-5551 (1992).
Sheilds et al, 2001, J. Biol. Chem., vol. 276 (9), 6591-6604.
Parlevliet, T.E., et al. "CNT0736, a noval GLP-1 analogue, ameliorates insulin resistance and reduces VLDL production high-fat-fed C57BI/6 mice", 67th Annu Meetin Sci Secc Am Diabetes Assoc (online), Jun. 22, 2007, Retrieved from the Internet: URL:http://integrity.prous.com/integrity/servlet/xmlxs1/pk_ref_list.xml_show_ficha_ref?pref_id=1111353.
Parlevliet, T.E., et al. "CNT0736, a nova GLP-1 analogue, ameliorates insulin resistance and reduces VLDL production high-fat-fed C57B1/6 mice", 67th Annu Meetin Sci Secc Am Diabetes Assoc (online), Jun. 22, 2007, Retrieved from the Internet: URL:http://integrity.prous.com/integrity/servlet/xmlxs1/pk_ref_list.xml_show_ficha_ref?p_ref_id=1112933.
Picha et al. "Sustained GLP-1R-dependent control of glucose homeostasis by a GLP-1 mimetibody" Diabetologaia, vol. 50, No. 1 suppl. Sep. 1, 2008, p. S245.

\* cited by examiner

METHOD FOR TREATING INSULIN SENSITIVITY BY LONG-ACTING GLP-1 RECEPTOR MIMETIBODY AGONISTS

This application claims priority to U.S. Provisional Application Ser. No. 60/871,142, filed 21 Dec. 2006, the entire contents of which is incorporated herein by reference.

BACKGROUND OF THE INVENTION

1. Field of the Invention

The present invention relates to mammalian glucagons like peptide-1 (GLP-1) receptor agonists, such as GLP-1 mimetibody constructs, specified portions and variants specific for biologically active proteins, fragment or ligands, GLP-1 receptor agonist encoding and complementary nucleic acids, host cells, and methods of making and using thereof, including improving insulin sensitivity or lipid profiles in obesity related disorders and related therapeutic formulations, administration and devices.

2. Related Art

Recombinant proteins are an emerging class of therapeutic agents. The use of recombinant proteins as potential therapeutics have provided an opportunity for advances in therapeutic protein formulations, also including the use of chemical modifications. Such modifications can potentially enhance the therapeutic utility of therapeutic proteins, potentially such as by increasing serum half lives (e.g., by blocking their exposure to proteolytic enzymes), enhancing biological activity, and/or reducing unwanted side effects. One such modification is the use of immunoglobulin fragments fused to receptor proteins, such as enteracept. Fusion proteins have also been constructed using the antibody Fc domain in an attempt to provide a longer half-life or to incorporate functions such as Fc receptor binding, protein A binding, and complement fixation.

Obesity is a chronic disease manifested by the excess of fat mass in proportion to body size. Approximately one third of Americans are over-weight based on Body Mass Index (BMI>25 kg/m$^2$), and obesity is considered to be reaching epidemic proportions. The importance of obesity's threat to health is emphasized by the fact that obesity is an underlying cause or a risk factor for developing other diseases such as Type 2 Diabetes, cardiovascular disease, osteoartritis, and sleep apnea. Even a modest decrease in body weight (5-10% of initial body weight) may significantly decrease risk factors for developing obesity-associated diseases and improve metabolic syndrome conditions characterized by obesity, atherogenic dyslipidemia, raised blood pressure and insulin resistance.

The need to treat obesity is widely recognized and efforts are being made by all major pharmaceutical companies to develop a successful therapy. Obesity is currently treated by: 1) life style changes, 2) three drugs currently on the market (Phentramine, Orlisata and Sibutramine) that have a modest effect on weight loss and are associated with significant side effects and 3) by surgery.

Glucagon-like peptide-1 (GLP-1) is a 30 amino acid hormone secreted from gut endocrine cells in response to nutrient ingestion. GLP-1 travels through the circulation and binds to the GLP-1 receptor on the pancreas, resulting in an increase in insulin secretion. In addition, it has been shown that GLP-1 reduces gastric emptying which decreases the amount of glucose that is released into the circulation. These actions combine to lower blood glucose levels. Thus, the mechanism of biological activity of GLP-1 suggests that it could be an attractive therapeutic for the treatment of type 2 diabetes.

GLP-1 also has the potential to treat obesity. Several studies have shown that GLP-1 administered either peripherally or intracerebroventricularly (ICV) decreases food intake in animal models. A study in humans delivering GLP-1 continuously for five days in obese, diabetic patients resulted in a reduction in food intake and a reduction in body weight. However, GLP-1 is not being developed as a therapeutic because of its exceptionally short half-life ($T_{1/2}$~1-2 min). It is rapidly degraded by dipeptidyl protease (DPP-IV), thus reducing the length of the peptide by 2 amino acids at the N-terminus and inactivating it.

There are several GLP-1 analogues that are currently in development or on the market. Byetta™ is a recently marketed GLP-1 analogue developed by Amylin and Eli Lilly. It was first identified in the saliva of the gila monster lizard, and is 53% identical to GLP-1. Byetta™ is resistant to DPP-IV, yet it still requires twice daily pre-prandial dosing partially due to its short in vivo half-life (less than 30 minutes). During clinical trials where Byetta™ was evaluated as a therapy for Type 2 Diabetes, HbAlc levels were lowered approximately 1% following 82 weeks of treatment. Interestingly, patients taking Byetta™ had a sustained decrease in body weight (5-10 pounds) during the course of the study, supporting the theory that GLP-1 analogues have potential for the treatment of obesity. Liraglutide is a lipidated GLP-1 analogue being developed by Novo Nordisk, and it is currently in clinical trials. Based upon the pharmacokinetics of the molecule, it is anticipated that liraglutide will be dosed once daily. A GLP-1 therapy that has an increased half-life such that it could be dosed once weekly or monthly would have a significant advantage over other GLP-1 peptides in development.

Diabetes is a growing epidemic that is estimated will affect over 300 million people by the year 2025 pending an effective pharmaceutical cure. Type 2 diabetes accounts for 90-95% of all cases. Complications resulting from sustained elevated plasma glucose levels include cardiovascular disease, nephropathy, neuropathy, and retinopathy. Current treatments for diabetes are associated with a variety of deleterious side effects including hypoglycemia and weight gain. In addition, current treatments for type 2 diabetes do not cure the disease but simply prolong the time until patients require insulin therapy.

Glucagon like peptide-1 (GLP-1) is a 30-amino acid peptide secreted from the L-cells of the intestine following food digestion. Because of a spectrum of favorable anti-diabetic actions including glucose-dependent insulinotropic action, an effect to slow gastric emptying, and a role in lowering food intake and body weight, GLP-1 has been widely explored as a potential therapy for treating type 2 diabetes. However, native GLP-1 is not a viable therapeutic because it is rapidly inactivated in vivo by the protease DPP-IV with a half life is less than 2 minutes. Exenatide is a DPP-IV resistant GLP-1 analogue currently approved for treatment of Type 2 diabetes. It is a small peptide that requires twice daily preprandial dosing because its in vivo half life is less than 30 minutes.

In addition to the pharmacodynamic effects described above, both GLP-1 and exenatide positively affect the peripheral actions of insulin. Euglycemic hyperinsulinemic clamp studies in diabetic rats showed that chronic, but not acute administration of GLP-1 or exenatide leads to a significant improvement in insulin sensitivity.

Accordingly, there is a need to provide improved and/or modified versions of GLP-1 therapeutic proteins, which overcome one or more of these and other problems known in the art.

SUMMARY OF THE INVENTION

The mimetibody constructs technology provides a novel delivery platform for peptide therapeutics. A GLP-1 mimetibody constructs may provide a means of delivering the GLP-1 peptide in a sustained manner, providing an improvement over GLP-1 peptides currently in development. Byetta™ shows sustained weight loss even though the half-life of the molecule is relatively short. A GLP-1 analogue with a sustained pharmacokinetic profile has the potential to reduce food intake and body weight to a greater extent and to improve insulin sensitivity and lipid profiles. Furthermore, the GLP-1 mimetibody constructs is quite different from other GLP-1 analogues in development or on the market. It is a large protein rather than a peptide, and it has two peptides per molecule. Based upon its size and dimeric structure, a GLP-1 mimetibody constructs is expected to have differentiable features relative to other molecules. For example, it is possible that activation of the GLP-1 receptor by a dimeric molecule is different from a monomeric molecule, resulting in differences in the signaling pathway. In addition, it is possible that the size of the molecule results in a very different tissue distribution profile, which may result in different pharmacodynamic properties.

The present invention provides human GLP-1 receptor agonists, including GLP-1 mimetibody constructs including modified proteins, peptides, immunoglobulins, cleavage products and other specified portions and variants thereof, as well as GLP-1 receptor agonist or mimetibody constructs compositions, encoding or complementary nucleic acids, vectors, host cells, compositions, formulations, devices, transgenic animals, transgenic plants, and methods of making and using thereof, as described and/or enabled herein, in combination with what is known in the art.

Preferably, such GLP-1 mimetibody constructs are improved for expression, purification and/or stability by changing O-linked glycosylation sites (such as but not limited to Val-Xaa-Ser) to N-linked glycosylation sites (such as, but not limited to, Asn-Xaa-Ser or Gln-Xaa-Ser). The present invention provides such improvements to GLP-1 CH1 deleted mimetibody constructs (e.g., alanine) or o-glycosylation sites, such as but not limited to the sequence Val-Xaa-Ser, can be substituted with N-glycosylation sites, such as Asn-Xaa-Ser or Gln-Xaa-Ser, as may be preferred, e.g., but not limited to, as done at the following residues presented in the Sequence Listing: Val-Xaa-Ser (O-glycosylation site) changes to N-glycosylation site Asn-Xaa-Ser at: position 44 in SEQ ID NOS:2, 4, 7-14, position 64 in SEQ ID NOS:43, 45, position 82 in SEQ ID NOS:44, 46 and 51; position 88 in SEQ ID NOS:48, 50, 53-55, position 89 in SEQ ID NO:47, position 90 in SEQ ID NO:49; position 103 and/or 185 in SEQ ID NOS:56 and 63; or position 39 in SEQ ID NOS:60 and 61; position 79 in SEQ ID NO:64 or any other suitable position as disclosed herein or as known in the art).

GLP-1 receptor agonists can be used to provide a novel therapy for the reduction of body weight in obese individuals. In animal models that are known to correlate with therapeutic efficacy, a GLP-1 receptor agonist, CNTO 736, a GLP-1 mimetibody constructs, decreases food intake and body weight, due to the reduction in fat mass.

The present invention also provides at least one isolated GLP-1 receptor agonist or mimetibody constructs or specified portion or variant as described herein and/or as known in the art. The GLP-1 mimetibody constructs can optionally comprise at least one CH3 region directly linked with at least one CH2 region directly linked with at least one portion of at least one hinge region or fragment thereof (H), directly linked with at least one partial variable region (V), directly linked with an optional linker sequence (L), directly linked to at least one GLP-1 therapeutic peptide (P).

In a preferred embodiment a pair of a CH3-CH2-hinge-partial V region sequence-linker-therapeutic peptide sequence, the pair optionally linked by association or covalent linkage, such as, but not limited to, at least one Cys-Cys disulfide bond or at least one $CH_4$ or other immunglobulin sequence. In one embodiment, a GLP-1 mimetibody constructs comprises formula (I):

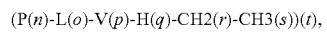

(P(n)-L(o)-V(p)-H(q)-CH2(r)-CH3(s))(t),    a wherein P is at least one bioactive GLP-1 peptide, variant or derivative, L is at least one linker sequence, which can be a polypeptide that provides structural flexibility by allowing the agonist or mimetibody constructs to have alternative orientations and binding properties, V is at least one portion of a C-terminus of an immunoglobulin variable region, H is at least one portion of an immunoglobulin variable hinge region, CH2 is at least a portion of an immunoglobulin CH2 constant region, CH3 is at least a portion of an immunoglobulin CH3 constant region, n is an integer from 1 to 10, and o, p, q, r, s, and t can be independently an integer from 0 to 10, mimicking different types of immunoglobulin molecules, e.g., but not limited to IgG1, IgG2, IgG3, IgG4, IgA1, IgA2, IgM, IgD, IgE, or any subclass thereof, and the like, or any combination thereof.

The variable region of the antibody sequence can be, but not limited to, at least one portion of at least one of SEQ ID NOS:47-55, or fragment thereof, further optionally comprising at least one substitution, insertion or deletion. The CH2, CH3 and hinge region can be, but not limited to, at least one portion of at least one of SEQ ID NOS:56-64, or fragment thereof as described in Table 3, further optionally comprising at least one substitution, insertion or deletion as as further described in FIGS. 32-40 of PCT publication WO 05/05604 (PCT US04/19898) filed Jun. 24, 2004 and published Jan. 20, 2005, with corresponding SEQ ID NOS:32-40.

Thus, a GLP-1 mimetibody constructs of the present invention mimics at least a portion of an antibody or immuoglobulin structure or function with its inherent properties and functions, while providing a GLP-1 therapeutic peptide and its inherent or acquired in vitro, in vivo or in situ properties or activities. The various portions of the antibody and therapeutic peptide portions of GLP-1 mimetibody constructs of the present invention can vary as described herein in combination with what is known in the art.

The present invention also provides at least one isolated GLP-1 receptor agonist or mimetibody constructs or specified portion or variant that has at least one activity, such as, but not limited to known biological activities of at least one bioactive GLP-1 peptide or polypeptide corresponding to the P portion of formula (I), as described herein or known in the art.

In one aspect, the present invention provides at least one isolated human GLP-1 receptor agonist or mimetibody constructs comprising at least one polypeptide sequence of SEQ ID NO:1, or optionally with one or more substitutions, deletions or insertions as described herein or as known in the art. In another aspect, at least one GLP-1 receptor agonist or mimetibody constructs or specified portion or variant of the invention mimics the binding of at least one GLP-1 peptide or polypeptide corresponding to the P portion of the mimetibody constructs in formula (I), to at least one epitope comprising at least 1-3, to the entire amino acid sequence of at least one ligand, e.g., but not limited to, a GLP-1 receptor, or fragment thereof, wherein the ligand binds to at least a portion of SEQ ID NO:1, or optionally with one or more substitutions, deletions or insertions as described herein or as known in the art. The at least one GLP-1 receptor agonist or mimetibody constructs can optionally bind GLP-1 receptor with an affinity of at least $10^{-9}$ M, at least $10^{-10}$ M, at least $10^{-11}$ M, or at least $10^{-12}$ M. A GLP-1 receptor agonist or mimetibody constructs can thus be screened for a corresponding activity according to known methods, such as, but not limited to the binding activity towards a receptor or fragment thereof.

The present invention further provides at least one anti-idiotype antibody to at least one GLP-1 receptor agonist or mimetibody constructs of the present invention. The anti-idiotype antibody or fragment specifically binds at least one GLP-1 receptor agonist or mimetibody constructs of the present invention. The anti-idiotype antibody includes any protein or peptide containing molecule that comprises at least a portion of an immunoglobulin molecule, such as but not limited to at least one complimetarity determining region (CDR) of a heavy or light chain or a ligand binding portion thereof, a heavy chain or light chain variable region, a heavy chain or light chain constant region, a framework region, or any portion thereof, that competitively binds a GLP-1 ligand binding region of at least one GLP-1 receptor agonist or mimetibody constructs of the present invention. Such idiotype antibodies of the invention can include or be derived from any mammal, such as but not limited to a human, a mouse, a rabbit, a rat, a rodent, a primate, and the like.

The present invention provides, in one aspect, isolated nucleic acid molecules comprising, complementary, having significant identity or hybridizing to, a polynucleotide encoding at least one GLP-1 receptor agonist or mimetibody constructs or GLP-1 receptor agonist or mimetibody constructs anti-idiotype antibody, or specified portions or variants thereof, comprising at least one specified sequence, domain, portion or variant thereof. The present invention further provides recombinant vectors comprising at least one of said isolated GLP-1 receptor agonist or mimetibody constructs or GLP-1 receptor agonist or mimetibody constructs anti-idiotype antibody encoding nucleic acid molecules, host cells containing such nucleic acids and/or recombinant vectors, as well as methods of making and/or using such GLP-1 receptor agonist or mimetibody constructs or GLP-1 receptor agonist or mimetibody constructs anti-idiotype antibody nucleic acids, vectors and/or host cells.

Also provided is an isolated nucleic acid encoding at least one isolated mammalian GLP-1 receptor agonist or mimetibody constructs or GLP-1 receptor agonist or mimetibody constructs anti-idiotype antibody; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 653, SP2/0, 293, HeLa, myeloma, or lymphoma cells, or any derivative, immortalized or transformed cell thereof.

The present invention also provides at least one method for expressing at least one GLP-1 receptor agonist or mimetibody constructs or GLP-1 receptor agonist or mimetibody constructs anti-idiotype antibody, or specified portion or variant in a host cell, comprising culturing a host cell as described herein and/or as known in the art under conditions wherein at least one GLP-1 receptor agonist or mimetibody constructs or GLP-1 receptor agonist or mimetibody constructs anti-idiotype antibody, or specified portion or variant is expressed in detectable and/or recoverable amounts. Also provided is a method for producing at least one GLP-1 receptor agonist or mimetibody constructs or GLP-1 receptor agonist or mimetibody constructs anti-idiotype antibody, comprising translating the GLP-1 receptor agonist or mimetibody constructs or GLP-1 receptor agonist or mimetibody constructs anti-idiotype antibody encoding nucleic acid under conditions in vitro, in vivo or in situ, such that the GLP-1 receptor agonist or mimetibody constructs or GLP-1 receptor agonist or mimetibody constructs anti-idiotype antibody is expressed in detectable or recoverable amounts.

Also provided is a method for producing at least one isolated human GLP-1 receptor agonist or mimetibody constructs or GLP-1 anti-idiotype antibody of the present invention, comprising providing a host cell or transgenic animal or transgenic plant capable of expressing in recoverable amounts the GLP-1 receptor agonist or mimetibody constructs or GLP-1 anti-idiotype antibody.

Further provided in the present invention is at least one GLP-1 receptor agonist or mimetibody constructs produced by the above methods.

The present invention also provides at least one composition comprising (a) an isolated GLP-1 receptor agonist or mimetibody constructs or specified portion or variant encoding nucleic acid and/or GLP-1 receptor agonist or mimetibody constructs as described herein; and (b) a suitable carrier or diluent. The carrier or diluent can optionally be pharmaceutically acceptable, according to known methods. The composition can optionally further comprise at least one further compound, protein or composition.

Also provided is a composition comprising at least one isolated human GLP-1 receptor agonist or mimetibody constructs and at least one pharmaceutically acceptable carrier or diluent. The composition can optionally further comprise an effective amount of at least one compound or protein selected from at least one of a diabetes drug, an insulin metabolism related drug, a glucose metabolism related drug, a detectable label or reporter, an anti-infective drug, a cardiovascular (CV) system drug, a central nervous system (CNS) drug, an autonomic nervous system (ANS) drug, a respiratory tract drug, a gastrointestinal (G1) tract drug, a hormonal drug, a drug for fluid or electrolyte balance, a hematologic drug, an antineoplastic, an immunomodulation drug, an ophthalmic, otic or nasal drug, a topical drug, a nutritional drug, a TNF antagonist, an antirheumatic, a muscle relaxant, a narcotic, a non-steroid anti-inflammatory drug (NTHE), an analgesic, an anesthetic, a sedative, a local anesthetic, a neuromuscular blocker, an antimicrobial, an antpsoriatic, a corticosteriod, an anabolic steroid, an erythropoietin, an immunization, an immunoglobulin, an immunosuppressive, a growth hormone, a hormone replacement drug, a radiopharmaceutical, an anti-depressant, an antipsychotic, a stimulant, an asthma medication, a beta agonist, an inhaled steroid, an epinephrine or analog, a cytokine, or a cytokine antagonist.

The present invention also provides at least one composition, device and/or method of delivery of a therapeutically or prophylactically effective amount of at least one GLP-1 receptor agonist or mimetibody constructs or specified portion or variant, according to the present invention.

The present invention further provides at least one GLP-1 receptor agonist or mimetibody constructs method or composition, for administering a therapeutically effective amount to modulate or treat at least one GLP-1 related condition in a cell, tissue, organ, animal or patient and/or, prior to, subsequent to, or during a related condition, as known in the art and/or as described herein.

The present invention further provides at least one GLP-1 receptor agonist or mimetibody constructs, specified portion or variant in a method or composition, when administered in a therapeutically effective amount, for modulation, for treating or reducing the symptoms of, at least one metabolic, immune, cardiovascular, infectious, malignant, and/or neurologic disease in a cell, tissue, organ, animal or patient and/or, as needed in many different conditions, such as but not limited to, prior to, subsequent to, or during a related disease or treatment condition, as known in the art.

The present invention further provides at least one GLP-1 receptor agonist or mimetibody constructs specified portion or variant in a method or composition, when administered in a therapeutically effective amount, for modulation, for treating or reducing the symptoms of at least one of a insuling sensitivity or lipid profile related disorder, a glucose metabolism related disorder, a bone and joint disorder, cardiovascular disorder, a dental or oral disorder, a dermatologic disorder, an ear, nose or throat disorder, an endocrine or metabolic disorder, a gastrointestinal disorder, a gynecologic disorder, a hepatic or biliary disorder, a an obstetric disorder, a hematologic disorder, an immunologic or allergic disorder, an infectious disease, a musculoskeletal disorder, a oncologic disorder, a neurologic disorder, a nutritrional disorder, an opthalmologic disorder, a pediatric disorder, a poisoning disorder, a psychiatric disorder, a renal disorder, a pulmonary disorder, or any other known disorder, (See, e.g., The Merck Manual, 17th ed., Merck Research Laboratories, Merck and Co., Whitehouse Station, N.J. (1999), entirely incoporated herein by reference), as needed in many different conditions, such as but not limited to, prior to, subsequent to, or during a related disease or treatment condition, as known in the art.

The present invention also provides at least one composition, device and/or method of delivery, for diagnosing GLP-1 related conditions, of at least one GLP-1 receptor agonist or mimetibody constructs, according to the present invention.

The present invention further provides at least one GLP-1 receptor agonist or mimetibody constructs method or composition, for diagnosing at least one GLP-1 related condition in a cell, tissue, organ, animal or patient and/or, prior to, subsequent to, or during a related condition, as known in the art and/or as described herein.

Also provided is a method for diagnosing or treating a disease condition in a cell, tissue, organ or animal, comprising: (a) contacting or administering a composition comprising an effective amount of at least one isolated human GLP-1 receptor agonist or mimetibody constructs of the invention with, or to, the cell, tissue, organ or animal. The method can optionally further comprise using an effective amount of 0.001-50 mg/kilogram, or equivalent concentration or molarity if done in vitro or in situ, of the cells, tissue, organ or animal per 0-24 hours, 1-7 days, 1-52 weeks, 1-24 months, 1-50 years or any range or value therein. The method can optionally further comprise using the contacting or the administrating by at least one mode selected from in vitro, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

The method can optionally further comprise administering, prior, concurrently or after the (a) contacting or administering, at least one composition comprising an effective amount of at least one compound or protein selected from at least one of a diabetes drug, an insulin metabolism related drug, a glucose metabolism related drug, a detectable label or reporter, an anti-infective drug, a cardiovascular (CV) system drug, a central nervous system (CNS) drug, an autonomic nervous system (ANS) drug, a respiratory tract drug, a gastrointestinal (G1) tract drug, a hormonal drug, a drug for fluid or electrolyte balance, a hematologic drug, an antineoplactic, an immunomodulation drug, an ophthalmic, otic or nasal drug, a topical drug, a nutritional drug, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, a cytokine antagonist, vitamins, growth factors, or antioxidants.

Also provided is a medical device, comprising at least one isolated human GLP-1 receptor agonist or mimetibody constructs of the invention, wherein the device is suitable to contacting or administering the at least one GLP-1 receptor agonist or mimetibody constructs by at least one mode selected from in vitro, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is an article of manufacture for human pharmaceutical or diagnostic use, comprising packaging material and a container comprising a solution or a lyophilized form of at least one isolated human GLP-1 receptor agonist or mimetibody constructs of the present invention. The article of manufacture can optionally comprise having the container as a component of an in vitro, a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present invention further provides any invention described herein.

DESCRIPTION OF THE INVENTION

The present invention provides isolated, recombinant and/or synthetic mimetibody constructs or specified portions or variants, as well as compositions and encoding nucleic acid molecules comprising at least one polynucleotide encoding at least one GLP-1 receptor agonist or mimetibody constructs. Such mimetibody constructs or specified portions or variants of the present invention comprise specific GLP-1 receptor agonist or mimetibody constructs sequences, domains, fragments and specified variants thereof, and methods of making and using said nucleic acids and mimetibody constructs or specified portions or variants, including therapeutic compositions, methods and devices.

Preferably, such GLP-1 mimetibody constructs are improved for expression, purification and/or stability by changing O-linked glycosylation sites (such as but not limited to Val-Xaa-Ser) to N-linked glycosylation sites (such as, but not limited to, Asn-Xaa-Ser or Gln-Xaa-Ser). The present invention provides such improvements to GLP-1 CH1 deleted mimetibody constructs.

The present invention also provides at least one isolated GLP-1 mimetibody constructs or specified portion or variant as described herein and/or as known in the art. The GLP-1 mimetibody constructs can optionally comprise at least one CH3 region directly linked with at least one CH2 region directly linked with at least one hinge region or fragment thereof (H), directly linked with at least one partial variable region (V), directly linked with an optional linker sequence (L), directly linked to at least one GLP-1 therapeutic peptide (P).

In a preferred embodiment a GLP-1 mimetibody constructs comprises formula (I):

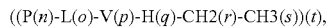

((P(n)-L(o)-V(p)-H(q)-CH2(r)-CH3(s))(t), b wherein P is at least one bioactive GLP-1 polypeptide, L is at least one linker sequence, which can be a polypeptide that provides structural flexablity by allowing the mimietibody to have alternative orientations and binding properties, V is at least one portion of a C-terminus of an immunoglobulin variable region, H is at least one portion of an immunoglobulin variable hinge region, CH2 is at least a portion of an immunoglobulin CH2 constant region, CH3 is at least a portion of an immunoglobulin CH3 constant region, m, n, o, p, q, r, s and t can be independently an integer between and including 0 and 10, mimicking different types of immunoglobulin molecules, e.g., but not limited to IgG1, IgG2, IgG3, IgG4, IgA1, IgA2, IgM, IgD, IgE, or any subclass thereof, and the like, or any combination thereof.

Preferably, such GLP-1 mimetibody constructs are improved for expression, purification and/or stability by changing O-linked glycosylation sites (such as but not limited to Val-Xaa-Ser) to N-linked glycosylation sites (such as, but not limited to, Asn-Xaa-Ser or Gln-Xaa-Ser). The present invention provides such improvements to GLP-1 CH1 deleted mimetibody constructs.

Thus, a GLP-1 mimetibody constructs of the present invention mimics an antibody structure with its inherent properties and functions, while providing a therapeutic peptide and its inherent or acquired in vitro, in vivo or in situ properties or activities. In a preferred embodiment where t=1, the monomer CH3-CH2-hinge-partial J sequence-linker-therapeutic peptide can be linked to other monomers by association or covalent linkage, such as, but not limited to, a Cys-Cys disulfide bond. The various portions of the antibody and the GLP-1 therapeutic peptide portions of at least one GLP-1 mimetibody constructs of the present invention can vary as described herein in combination with what is known in the art.

The portion of CH3-CH2-hinge may be extensively modified to form a variant in accordance with this invention, provided binding to the salvage receptor is maintained. In such variants, one may remove one or more native sites that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. A variant of CH3-CH2-hinge may lack one or more native sites or residues that affect or are involved in (1) disulfide bond formation, (2) incompatibility with a selected host cell, (3) heterogeneity upon expression in a selected host cell, (4) glycosylation, (5) interaction with complement, (6) binding to an Fc receptor other than a salvage receptor, or (7) antibody-dependent cellular cytotoxicity (ADCC). Exemplary CH3-CH2-hinge variants include molecules and sequences in which: 1. Sites involved in disulfide bond formation are removed. Such removal may avoid reaction with other cysteine-containing proteins present in the host cell used to produce the molecules of the invention. For this purpose, the cysteine residues may be deleted or substituted with other amino acids (e.g., alanyl, seryl). Even when cysteine residues are removed, the single chain CH3-CH2-hinge domains can still form a dimeric CH3-CH2-hinge domain that is held together non-covalently; 2. The CH3-CH2-hinge region is modified to make it more compatible with a selected host cell. For example, when the molecule is expressed recombinantly in a bacterial cell such as E. coli, one may remove the PA sequence in the hinge, which may be recognized by a digestive enzyme in E. coli such as proline iminopeptidase; 3. A portion of the hinge region is deleted or substituted with other amino acids to prevent heterogeneity when expressed in a selected host cell; 4. One or more glycosylation sites are removed. Residues that are typically glycosylated (e.g., valine or asparagine) may confer cytolytic response. Such residues may be deleted or substituted with unglycosylated residues (e.g., alanine) or o-glycosylation sites, such as but not limited to the sequence Val-Xaa-Ser, can be substituted with N-glycosylation sites, such as Asn-Xaa-Ser or Gln-Xaa-Ser, as may be preferred, e.g., as done at the following residues presented in the Sequence Listing: Val-Xaa-Ser (O-glycosylation site) changes to N-glycosylation site Asn-Xaa-Ser at: position 44 in SEQ ID NOS:2, 4, 7-14, position 64 in SEQ ID NOS:43, 45, position 82 in SEQ ID NOS:44, 46 and 51; position 88 in SEQ ID NOS:48, 50, 53-55, position 89 in SEQ ID NO:47, position 90 in SEQ ID NO:49; position 103 and/or 185 in SEQ ID NOS:56 and 63; or position 39 in SEQ ID NOS:60 and 61; position 79 in SEQ ID NO:64 or any other suitable position as disclosed herein or as known in the art); 5. Sites involved in interaction with complement, such as the C1q binding site, are removed. Complement recruitment may not be advantageous for the molecules of this invention and so may be avoided with such a variant; 6. Sites are removed that affect binding to Fc receptors other than a salvage receptor. The CH3-CH2-hinge region may have sites for interaction with certain white blood cells that are not required for the fusion molecules of the present invention and so may be removed; 7. The ADCC site is removed. ADCC sites are known in the art; see, for example, Molec. Immunol. 29 (5): 633-9 (1992) with regard to ADCC sites in IgG1. These sites, as well, are not required for the fusion molecules of the present invention and so may be removed.

Linker polypeptide provides structural flexibility by allowing the mimetibody constructs to have alternative orientations and binding properties. When present, its chemical structure is not critical. The linker is preferably made up of amino acids linked together by peptide bonds. Thus, in preferred embodiments, the linker is made up of from 1 to 20 amino acids linked by peptide bonds, wherein the amino acids are selected from the naturally occurring amino acids. Some of these amino acids may be glycosylated, as is well understood by those in the art. In a more preferred embodiment, the 1 to 20 amino acids are selected from glycine, alanine, serine, proline, asparagine, glutamine, and lysine. Even more preferably, a linker is made up of a majority of amino acids that are sterically unhindered, such as glycine and alanine. Thus, preferred linkers are poly(Gly-Ser), polyglycines (particularly $(Gly)_4$, $(Gly)_5$), poly(Gly-Ala), and polyalanines. Other specific examples of linkers are: $(Gly)_3Lys(Gly)_4$ (SEQ ID NO:65), $(Gly)_3AsnGlySer(Gly)_2$ (SEQ ID NO:66), $(Gly)_3Cys(Gly)_4$ (SEQ ID NO:67), and GlyProAsnGlyGly (SEQ ID NO:68).

To explain the above nomenclature, for example, $(Gly)_3Lys(Gly)_4$ means Gly-Gly-Gly-Lys-Gly-Gly-Gly-Gly. Combinations of Gly and Ala are also preferred. The linkers shown here are exemplary; linkers within the scope of this invention may be much longer and may include other residues.

Non-peptide linkers are also possible. For example, alkyl linkers such as —NH—$(CH_2)s$—C(O)—, wherein s=2-20 could be used. These alkyl linkers may further be substituted by any non-sterically hindering group such as lower alkyl (e.g., $C_1$-$C_6$) lower acyl, halogen (e.g., Cl, Br), CN, NH2, phenyl, etc. An exemplary non-peptide linker is a PEG linker which has a molecular weight of 100 to 5000 kD, preferably 100 to 500 kD. The peptide linkers may be altered to form derivatives in the same manner as described above.

As used herein, a "GLP-1 peptide," or "GLP-1 peptide, variant, or derivative" can be at least one GLP-1 peptide, GLP-1 fragment, GLP-1 homolog, GLP-1 analog, or GLP-1 derivative. A GLP-1 peptide has from about twenty-five to about forty-five naturally occurring or non-naturally occurring amino acids that have sufficient homology to native GLP-1 (7-37) such that they exhibit insulinotropic activity by binding to the GLP-1 receptor on β-cells in the pancreas. GLP-1 (7-37) has the amino acid sequence of SEQ ID NO:15: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly.

A GLP-1 fragment is a polypeptide obtained after truncation of one or more amino acids from the N-terminus and/or C-terminus of GLP-1 (7-37) or an analog or derivative thereof. A GLP-1 homolog is a peptide in which one or more amino acids have been added to the N-terminus and/or C-terminus of GLP-1 (7-37), or fragments or analogs thereof. A GLP-1 analog is a peptide in which one or more amino acids of GLP-1 (7-37) have been modified and/or substituted. A GLP-1 analog has sufficient homology to GLP-1 (7-37) or a fragment of GLP-1 (7-37) such that the analog has insulinotropic activity. A GLP-1 derivative is defined as a molecule having the amino acid sequence of a GLP-1 peptide, a GLP-1 homolog or a GLP-1 analog, but additionally having chemical modification of one or more of its amino acid side groups, α-carbon atoms, terminal amino group, or terminal carboxylic acid group.

Numerous active GLP-1 fragments, analogs and derivatives are known in the art and any of these analogs and derivatives can also be part of the GLP-1 receptor agonist or mimetibody constructs of the present invention. Some GLP-1 analogs and GLP-1 fragments known in the art are disclosed in U.S. Pat. Nos. 5,118,666, 5,977,071, and 5,545,618, and Adelhorst, et al., *J. Biol. Chem.* 269:6275 (1994). Examples include, but not limited to, GLP-1 (7-34), GLP-1 (7-35), GLP-1 (7-36), Gln9-GLP-1(7-37), D-Gln9-GLP-1(7-37), Thr16-Lys18-GLP-1 (7-37), and Lys18-GLP-1 (7-37).

A "GLP-1 receptor agonist or mimetibody constructs," "GLP-1 receptor agonist or mimetibody constructs portion," or "GLP-1 receptor agonist or mimetibody constructs fragment" and/or "GLP-1 receptor agonist or mimetibody constructs variant" and the like has, mimics or simulates at least one biological activity, such as but not limited to ligand binding, in vitro, in situ and/or preferably in vivo, of at least one GLP-1 peptide, variant or derivative, such as but not limited to at least one of SEQ ID NO:1. For example, a suitable GLP-1 receptor agonist or mimetibody constructs, specified portion, or variant can also modulate, increase, modify, activate, at least one GLP-1 receptor signaling or other measurable or detectable activity.

GLP-1 mimetibody constructs useful in the methods and compositions of the present invention are characterized by suitable affinity binding to protein ligands, for example, GLP-1 receptors, and optionally and preferably having low toxicity. In particular, a GLP-1 mimetibody constructs, where the individual components, such as the portion of variable region, constant region (without a CH1 portion) and framework, or any portion thereof (e.g., a portion of the J, D or V regions of the variable heavy or light chain; at least a portion of at least one hinge region, the constant heavy chain or light chain, and the like) individually and/or collectively optionally and preferably possess low immunogenicity, is useful in the present invention. The mimetibody constructs that can be used in the invention are optionally characterized by their ability to treat patients for extended periods with good to excellent alleviation of symptoms and low toxicity. Low immunogenicity and/or high affinity, as well as other undefined properties, may contribute to the therapeutic results achieved. "Low immunogenicity" is defined herein as raising significant HAMA, HACA or HAHA responses in less than about 75%, or preferably less than about 50, 45, 40, 35, 30, 35, 20, 15, 10, 9, 8, 7, 6, 5, 4, 3, 2, and/or 1% of the patients treated and/or raising low titres in the patient treated (less than about 300, preferably less than about 100 measured with a double antigen enzyme immunoassay) (see, e.g., Elliott et al., *Lancet* 344:1125-1127 (1994)).

Utility. The isolated nucleic acids of the present invention can be used for production of at least one GLP-1 receptor agonist or mimetibody constructs, fragment or specified variant thereof, which can be used to effect a cell, tissue, organ or animal (including mammals and humans), to modulate, treat, alleviate, help prevent the incidence of, or reduce the symptoms of, at least one insulin sensitivity or lipid profile related condition, selected from, but not limited to, at least one of a insulin sensitivity or lipid profile related disorder, any overweight condition related to excess body fat, an insulin metabolism related disorder, a glucose metabolism related disorder, an immune disorder or disease, a cardiovascular disorder or disease, an infectious, malignant, and/or neurologic disorder or disease, as well as other known or specified protein related conditions.

Such a method can comprise administering an effective amount of a composition or a pharmaceutical composition comprising at least one GLP-1 receptor agonist or receptor agonist or mimetibody constructs or specified portion or variant to a cell, tissue, organ, animal or patient in need of such modulation, treatment, alleviation, prevention, or reduction in symptoms, effects or mechanisms. The effective amount can comprise an amount of about 0.0001 to 500 mg/kg per single or multiple administration, or to achieve a serum concentration of 0.01-5000 µg/ml serum concentration per single or multiple administration, or any effective range or value therein, as done and determined using known methods, as described herein or known in the relevant arts.

Citations. All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2005); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2005); Colligan et al., Current Protocols in Protein Science, John Wiley & Sons, NY, N.Y., (1997-2005).

Mimetibody constructs of the Present Invention. The GLP-1 mimetibody constructs can optionally comprise at least one CH3 region directly linked with at least one CH2 region directly linked with at least one portion of at least one hinge region fragment (H), such as comprising at least one core hinge region, directly linked with at least one partial variable region (V), directly linked with an optional linker sequence (L), directly linked to at least one GLP-1 therapeutic peptide (P). In a preferred embodiment, a pair of a CH3-CH2-H-V-L-P can be linked by association or covalent linkage, such as, but not limited to, a Cys-Cys disulfide bond. Thus, a GLP-1 mimetibody constructs of the present invention mimics an antibody structure with its inherent properties and functions, while providing a therapeutic peptide and its inherent or acquired in vitro, in vivo or in situ properties or activities. The various portions of the antibody and therapeutic peptide portions of at least one GLP-1 mimetibody constructs of the present invention can vary as described herein in combination with what is known in the art.

Mimetibody constructs of the present invention thus provide at least one suitable property as compared to known proteins, such as, but not limited to, at least one of increased half-life, increased activity, more specific activity, increased avidity, increased or decrease off rate, a selected or more suitable subset of activities, less immungenicity, increased quality or duration of at least one desired therapeutic effect, less side effects, and the like.

Fragments of mimetibody constructs according to Formula (I) can be produced by enzymatic cleavage, synthetic or recombinant techniques, as known in the art and/or as described herein. Mimetibody constructs can also be produced in a variety of truncated forms using antibody genes in which one or more stop codons have been introduced upstream of the natural stop site. The various portions of mimetibody constructs can be joined together chemically by conventional techniques, or can be prepared as a contiguous protein using genetic engineering techniques. For example, a nucleic acid encoding at least one of the constant regions of a human antibody chain can be expressed to produce a contiguous protein for use in mimetibody constructs of the present invention. See, e.g., Ladner et al., U.S. Pat. No. 4,946,778 and Bird, R. E. et al., Science, 242: 423-426 (1988), regarding single chain antibodies.

As used herein, the term "human mimetibody constructs" refers to an antibody in which substantially every part of the protein (e.g., GLP-1 peptide, $C_H$ domains (e.g., $C_H^2$, $C_H^3$), hinge, V) is expected to be substantially non-immunogenic in humans with only minor sequence changes or variations. Such changes or variations optionally and preferably retain or reduce the immunogenicity in humans relative to non-modified human antibodies, or mimetibody constructs of the present invention. Thus, a human antibody and corresponding GLP-1 mimetibody constructs of the present invention is distinct from a chimeric or humanized antibody. It is pointed out that the GLP-1 mimetibody constructs can be produced by a non-human animal or cell that is capable of expressing human immunoglobulins (e.g., heavy chain and/or light chain) genes.

Human mimetibody constructs that are specific for at least one protein ligand thereof can be designed against an appropriate ligand, such as an isolated GLP-1 receptor, or a portion thereof (including synthetic molecules, such as synthetic peptides). Preparation of such mimetibody constructs are performed using known techniques to identify and characterize ligand binding regions or sequences of at least one protein or portion thereof.

In a preferred embodiment, at least one GLP-1 receptor agonist or mimetibody constructs or specified portion or variant of the present invention is produced by at least one cell line, mixed cell line, immortalized cell or clonal population of immortalized and/or cultured cells. Immortalized protein producing cells can be produced using suitable methods. Preferably, the at least one GLP-1 receptor agonist or mimetibody constructs or specified portion or variant is generated by providing nucleic acid or vectors comprising DNA derived or having a substantially similar sequence to, at least one human immunoglobulin locus that is functionally rearranged, or which can undergo functional rearrangement, and which further comprises a agonist or mimetibody constructs structure as described herein, e.g., but not limited to Formula (I), wherein portions of C-terminal variable regions can be used for V, hinge regions for H, CH2 for CH2 and CH3 for CH3, as known in the art.

The term "functionally rearranged," as used herein refers to a segment of nucleic acid from an immunoglobulin locus that has undergone V(D)J recombination, thereby producing an immunoglobulin gene that encodes an immunoglobulin chain (e.g., heavy chain), or any portion thereof. A functionally rearranged immunoglobulin gene can be directly or indirectly identified using suitable methods, such as, for example, nucleotide sequencing, hybridization (e.g., Southern blotting, Northern blotting) using probes that can anneal to coding joints between gene segments or enzymatic amplification of immunoglobulin genes (e.g., polymerase chain reaction) with primers that can anneal to coding joints between gene segments. Whether a cell produces a GLP-1 receptor agonist or mimetibody constructs or portion or variant comprising a particular variable region or a variable region comprising a particular sequence (e.g., at least one P sequence) can also be determined using suitable methods.

Mimetibody constructs, specified portions and variants of the present invention can also be prepared using at least one GLP-1 receptor agonist or mimetibody constructs or specified portion or variant encoding nucleic acid to provide transgenic animals or mammals, such as goats, cows, horses, sheep, and the like, that produce such mimetibody constructs or specified portions or variants in their milk. Such animals can be provided using known methods as applied for antibody encoding sequences. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Mimetibody constructs, specified portions and variants of the present invention can additionally be prepared using at least one GLP-1 receptor agonist or mimetibody constructs or specified portion or variant encoding nucleic acid to provide transgenic plants and cultured plant cells (e.g., but not limited to tobacco and maize) that produce such mimetibody constructs, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize or corn have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain mimetibody constructs (scFv's), including tobacco seeds and potato tubers. See, e.g., Conrad et al., Plant Mol. Biol. 38:101-109 (1998) and references cited therein. Thus, mimetibody constructs, specified portions and variants of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. The above references are entirely incorporated herein by reference.

The mimetibody constructs of the invention can bind human protein ligands with a wide range of affinities ($K_D$). In a preferred embodiment, at least one human GLP-1 receptor agonist or mimetibody constructs of the present invention can optionally bind at least one protein ligand with high affinity. For example, at least one GLP-1 receptor agonist or mimetibody constructs of the present invention can bind at least one protein ligand with a $K_D$ equal to or less than about $10^{-7}$ M or, more preferably, with a $K_D$ equal to or less than about 0.1-9.9 (or any range or value therein)$\times 10^{-7}$, $10^{-8}$, $10^{-9}$, $10^{-11}$, $10^{-12}$, or $10^{-13}$ M, or any range or value therein.

The affinity or avidity of a GLP-1 receptor agonist or mimetibody constructs for at least one protein ligand can be determined experimentally using any suitable method, e.g., as used for determining antibody-antigen binding affinity or avidity. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular GLP-1 receptor agonist or mimetibody constructs-ligand interaction can vary if measured under different conditions (e.g., salt concentration, pH). Thus, measurements of affinity and other ligand-binding parameters (e.g., $K_D$, $K_a$, $K_d$) are preferably made with standardized solutions of GLP-1 receptor agonist or mimetibody constructs and ligand, and a standardized buffer, such as the buffer described herein or known in the art.

Nucleic Acid Molecules. Using the information provided herein, such as the nucleotide sequences encoding at least 90-100% of the contiguous amino acids of at least one of SEQ ID NOS:1 and 6, as well as at least one portion of an antibody, wherein the above sequences are inserted as the P sequence of Formula (I) to provide a GLP-1 receptor agonist or mimetibody constructs of the present invention, further comprising specified fragments, variants or consensus sequences thereof, or a deposited vector comprising at least one of these sequences, a nucleic acid molecule of the present invention encoding at least one GLP-1 receptor agonist or mimetibody constructs or specified portion or variant can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combination thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, nucleic acid molecules comprising the coding sequence for a GLP-1 receptor agonist or mimetibody constructs or specified portion or variant; and nucleic acid molecules which comprise a nucleotide sequence substantially different from those described above but which, due to the degeneracy of the genetic code, still encode at least one GLP-1 receptor agonist or mimetibody constructs as described herein and/or as known in the art. Of course, the genetic code is well known in the art. Thus, it would be routine for one skilled in the art to generate such degenerate nucleic acid variants that code for specific GLP-1 receptor agonist or mimetibody constructs or specified portion or variants of the present invention. See, e.g., Ausubel, et al., supra, and such nucleic acid variants are included in the present invention.

As indicated herein, nucleic acid molecules of the present invention which comprise a nucleic acid encoding a GLP-1 receptor agonist or mimetibody constructs or specified portion or variant can include, but are not limited to, those encoding the amino acid sequence of a GLP-1 receptor agonist or mimetibody constructs fragment, by itself, the coding sequence for the entire GLP-1 receptor agonist or mimetibody constructs or a portion thereof, the coding sequence for a GLP-1 receptor agonist or mimetibody constructs, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding a GLP-1 receptor agonist or mimetibody constructs or specified portion or variant can be fused to a marker sequence, such as a sequence encoding a peptide that facilitates purification of the fused GLP-1 receptor agonist or mimetibody constructs or specified portion or variant comprising a GLP-1 receptor agonist or mimetibody constructs fragment or portion.

Polynucleotides Which Selectively Hybridize to a Polynucleotide as Described Herein. The present invention provides isolated nucleic acids that hybridize under selective hybridization conditions to a polynucleotide disclosed herein, or others disclosed herein, including specified variants or portions thereof. Thus, the polynucleotides of this embodiment can be used for isolating, detecting, and/or quantifying nucleic acids comprising such polynucleotides.

Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 40-99% sequence identity and can be employed to identify orthologous or paralogous sequences.

Optionally, polynucleotides of this invention will encode at least a portion of a GLP-1 receptor agonist or mimetibody constructs or specified portion or variant encoded by the polynucleotides described herein. The polynucleotides of this invention embrace nucleic acid sequences that can be employed for selective hybridization to a polynucleotide encoding a GLP-1 receptor agonist or mimetibody constructs or specified portion or variant of the present invention. See, e.g., Ausubel, supra; Colligan, supra, each entirely incorporated herein by reference.

Construction of Nucleic Acids. The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. See, e.g., Ausubel, supra; or Sambrook, supra.

Recombinant Methods for Constructing Nucleic Acids. The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under suitable stringency conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Synthetic Methods for Constructing Nucleic Acids. The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes. The present invention further provides recombinant expression cassettes comprising a nucleic acid of the present invention. A nucleic acid sequence of the present invention, for example a cDNA or a genomic sequence encoding a GLP-1 receptor agonist or mimetibody constructs or specified portion or variant of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution, as known in the art. A polynucleotide of the present invention can be expressed in either sense or anti-sense orientation as desired. It will be appreciated that control of gene expression in either sense or anti-sense orientation can have a direct impact on the observable characteristics. Another method of suppression is sense suppression. Introduction of nucleic acid configured in the sense orientation has been shown to be an effective means by which to block the transcription of target genes.

Vectors And Host Cells. The present invention also relates to vectors that include isolated nucleic acid molecules of the present invention, host cells that are genetically engineered with the recombinant vectors, and the production of at least one GLP-1 receptor agonist or mimetibody constructs or specified portion or variant by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced into a cell using suitable known methods, such as electroporation and the like, other known methods include the use of the vector as a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites optionally for at least one of transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one GLP-1 receptor agonist or mimetibody constructs or specified portion or variant of the present invention can be expressed in a modified form, such as a fusion protein, and can include not only secretion signals, but also additional heterologous functional regions. For instance, a region of additional amino acids, particularly charged amino acids, can be added to the N-terminus of a GLP-1 receptor agonist or mimetibody constructs or specified portion or variant to improve stability and persistence in the host cell, during purification, or during subsequent handling and storage. Also, peptide moieties can be added to a GLP-1 receptor agonist or mimetibody constructs or specified portion or variant of the present invention to facilitate purification. Such regions can be removed prior to final preparation of a GLP-1 receptor agonist or mimetibody constructs or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Illustrative of cell cultures useful for the production of the mimetibody constructs, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610, DG-44) and BSC-1 (e.g., ATCC CRL-26) cell lines, hepG2 cells, P3X63Ag8.653, SP2/0-Ag14, 293 cells, HeLa cells and the like, which are readily available from, for example, American Type Culture Collection, Manassas, Va. Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851).

Expression vectors for these cells can include one or more of the following expression control sequences, such as, but not limited to an origin of replication; a promoter (e.g., late or early SV40 promoters, the CMV promoter (e.g., U.S. Pat. Nos. 5,168,062; 5,385,839), an HSV tk promoter, a pgk (phosphoglycerate kinase) promoter, an EF-1 alpha promoter (e.g., U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of a GLP-1 Receptor Agonist or Mimetibody Constructs or Specified Portion or Variant Thereof. A GLP-1 receptor agonist or mimetibody constructs or specified portion or variant can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2005), e.g., Chapters 1, 4, 6, 8, 9, 10, each entirely incorporated herein by reference.

Mimetibody constructs or specified portions or variants of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the GLP-1 receptor agonist or mimetibody constructs or specified portion or variant of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Mimetibody Constructs, Specified Fragments and/or Variants. The isolated mimetibody constructs of the present invention comprise a GLP-1 receptor agonist or mimetibody constructs or specified portion or variant encoded by any one of the polynucleotides of the present invention as discussed more fully herein, or any isolated or prepared GLP-1 receptor agonist or mimetibody constructs or specified portion or variant thereof.

Preferably, the GLP-1 receptor agonist or mimetibody constructs or ligand-binding portion or variant binds at least one GLP-1 protein ligand and thereby provides at least one GLP-1 biological activity of the corresponding protein or a fragment thereof. Different therapeutically or diagnostically significant proteins are well known in the art and suitable assays or biological activities of such proteins are also well known in the art.

Non-limiting examples of suitable GLP-1 peptides, variants and derivatives for this invention appear as SEQ ID NO:1: His-Xaa2-Xaa3-Gly-Xaa5-Xaa6-Xaa7-Xaa8-Xaa9-Xaa10-Xaa11-Xaa12-Xaa13-Xaa 14-Xaa15-Xaa16-Xaa17-Xaa18-Xaa19-Xaa20-Xaa21-Phe-Xaa23-Xaa24-Xaa25-Xaa26-Xaa27-Xaa28-Xaa29-Xaa30-Xaa31, wherein: Xaa2 is Ala, Gly, Ser, Thr, Leu, Ile, Val, Glu, Asp, or Lys; Xaa3 is Glu, Asp, or Lys; Xaa5 is Thr, Ala, Gly, Ser, Leu, Ile, Val, Arg, His, Glu, Asp, or Lys; Xaa6 is Phe, His, Trp, or Tyr; Xaa7 is Thr or Asn; Xaa8 is Ser, Ala, Gly, Thr, Leu, Ile, Val, Glu, Asp, or Lys; Xaa9 is Asp or Glu; Xaa10 is Val, Ala, Gly, Ser, Thr, Leu, Ile, Met, Tyr, Trp, His, Phe, Glu, Asp, or Lys; Xaa11 is Ser, Val, Ala, Gly, Thr, Leu, Ile, Glu, Asp, or Lys; Xaa12 is Ser, Val, Ala, Gly, Thr, Leu, Ile, Glu, Asp or Lys; Xaa13 is Tyr, Gln, His, Glu, or Lys; Xaa14 is Leu, Ala, Met, Gly, Ser, Thr, Leu, Ile, Val, Glu, Asp, or Lys; Xaa15 is Glu, Ala, Thr, Ser, Gly, Gln, Asp or Lys; Xaa16 is Gly, Ala, Ser, Thr, Leu, Ile, Val, Gln, Asn, Arg, Cys, Glu, Asp or Lys; Xaa17 is Gln, Asn, Arg, His, Glu, Asp or Lys; Xaa18 is Ala, Gly, Ser, Thr, Leu, Ile, Val, Arg, Glu, Asp or Lys; Xaa19 is Ala, Gly, Ser, Thr, Leu, Ile, Val, Met, Glu, Asp or Lys; Xaa20 is Lys, Arg, His, Gln, Trp, Tyr, Phe, Glu or Asp; Xaa21 is Glu, Leu, Ala, His, Phe, Tyr, Trp, Arg, Gln, Thr, Ser, Gly, Asp or Lys; Xaa23 is Ile, Ala, Val, Leu or Glu; Xaa24 is Ala, Gly, Ser, Thr, Leu, Ile, Val, His, Glu, Asp or Lys; Xaa25 is Trp, Phe, Tyr, Glu, Asp or Lys; Xaa26 is Leu, Gly, Ala, Ser, Thr, Ile, Val, Glu, Asp or Lys; Xaa27 is Val, Leu, Gly, Ala, Ser, Thr, Ile, Arg, Glu, Asp or Lys; Xaa28 is Lys, Asn, Arg, His, Glu or Asp; Xaa29 is Gly, Ala, Ser, Thr, Leu, Ile, Val, Arg, Trp, Tyr, Phe, Pro, His, Glu, Asp or Lys; Xaa30 is Arg, His, Thr, Ser, Trp, Tyr, Phe, Glu, Asp or Lys; and Xaa31 is Gly, Ala, Ser, Thr, Leu, Ile, Val, Arg, Trp, Tyr, Phe, His, Glu, Asp, Lys.

Another preferred group of GLP-1 peptides, variants or derivatives are exemplified in SEQ ID NO:6: His-Xaa2-Xaa3-Gly-Thr-Xaa6-Xaa7-Xaa8-Xaa9-Xaa10-Ser-Xaa12-Tyr-Xaa14-Glu-Xaa16-Xaa17-Xaa18-Xaa19-Lys-Xaa21-Phe-Xaa23-Ala-Trp-Leu-Xaa27-Xaa28-Gly-Xaa30, wherein: Xaa2 is Ala, Gly, or Ser; Xaa3 is Glu or Asp; Xaa6 is Phe or Tyr; Xaa7 is Thr or Asn; Xaa8 is Ser, Thr or Ala; Xaa9 is Asp or Glu; Xaa10 is Val, Gln, Met or Ile; Xaa12 is Ser or Lys; Xaa14 is Leu, Gln, His, Glu, or Met; Xaa16 is Gly, Ala, Glu or Asp; Xaa17 is Gln or Glu; Xaa18 is Ala or Lys; Xaa19 is Ala, Val, Ile, Leu or Met; Xaa21 is Glu or Leu; Xaa23 is Ile, Ala, Val, Leu or Glu; Xaa 24 is Ala, Gln, His, Glu, or Lys; Xaa27 is Val, Gln, His, Glu, or Lys; Xaa28 is Lys or Asn; and Xaa30 is Arg or Glu.

These peptides can be prepared by methods disclosed and/or known in the art. The Xaas in the sequence (and throughout this specification, unless specified otherwise in a particular instance) include specified amino acid residues, derivatives or modified amino acids thereof. Because the enzyme, dipeptidyl-peptidase IV (DPP-IV), may be responsible for the observed rapid in vivo inactivation of administered GLP-1, GLP-1 peptides, homologs, analogs and derivatives that are protected from the activity of DPP-IV in the context of agonist or mimetibody constructs are preferred.

A GLP-1 receptor agonist or mimetibody constructs, or specified portion or variant thereof, that partially or preferably substantially provides at least one GLP-1 biological activity, can bind the GLP-1 ligand and thereby provide at least one activity that is otherwise mediated through the binding of GLP-1 to at least one ligand, such as a GLP-1 receptor, or through other protein-dependent or mediated mechanisms. As used herein, the term "GLP-1 receptor agonist or mimetibody constructs activity" refers to a GLP-1 receptor agonist or mimetibody constructs that can modulate or cause at least one GLP-1 dependent activity by about 20-10,000%, preferably by at least about 60, 70, 80, 90, 91, 92, 93, 94, 95, 96, 97, 98, 99, 100, 110, 120, 130, 140, 150, 160, 170, 180, 190, 200, 250, 300, 350, 400, 450, 500, 550, 600, 700, 800, 900, 1000, 2000, 3000, 4000, 5000, 6000, 7000, 8000, 9000% or more, depending on the assay.

The capacity of a GLP-1 receptor agonist or mimetibody constructs or specified portion or variant to provide at least one protein-dependent activity is preferably assessed by at least one suitable protein biological assay, as described herein and/or as known in the art. A human GLP-1 receptor agonist or mimetibody constructs or specified portion or variant of the invention can be similar to any class (IgG, IgA, IgM, etc.) or isotype and can comprise at least a portion of a kappa or lambda light chain. In one embodiment, the human GLP-1 receptor agonist or mimetibody constructs or specified portion or variant comprises IgG heavy chain variable fragments, hinge region, CH2 and CH3 of, at least one of isotypes, e.g., IgG1, IgG2, IgG3 or IgG4.

At least one GLP-1 receptor agonist or mimetibody constructs or specified portion or variant of the invention binds at least one ligand, subunit, fragment, portion or any combination thereof. The at least one GLP-1 peptide, variant or derivative of at least one GLP-1 receptor agonist or mimetibody constructs, specified portion or variant of the present invention can optionally bind at least one specified epitope of the ligand. The binding epitope can comprise any combination of at least one amino acid sequence of at least 1-3 amino acids to the entire specified portion of contiguous amino acids of the sequences of a protein ligand, such as a GLP-1 receptor or portion thereof.

Such mimetibody constructs can be prepared by joining together the various portions of Formula (I) of the GLP-1 receptor agonist or mimetibody constructs using known techniques, by preparing and expressing at least one nucleic acid molecules that encode the GLP-1 receptor agonist or mimetibody constructs using known techniques of recombinant DNA technology or by using any other suitable method, such as chemical synthesis.

Mimetibody constructs that bind to human GLP-1 ligands, such as receptors, and that comprise a defined heavy or light chain variable region or portion thereof, can be prepared using suitable methods, such as phage display (Katsube, Y., et al., *Int J Mol. Med,* 1(5):863-868 (1998)) or methods that employ transgenic animals, as known in the art. The GLP-1 receptor agonist or mimetibody constructs, specified portion or variant can be expressed using the encoding nucleic acid or portion thereof in a suitable host cell.

The invention also relates to mimetibody constructs, ligand-binding fragments and immunoglobulin chains comprising amino acids in a sequence that is substantially the same as an amino acid sequence described herein. Preferably, such mimetibody constructs or ligand-binding fragments thereof can bind human GLP-1 ligands, such as receptors, with high affinity (e.g., $K_D$ less than or equal to about $10^{-7}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes. The amino acids that make up mimetibody constructs or specified portions or variants of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994).

| SINGLE LETTER CODE | THREE LETTER CODE | NAME | THREE NUCL CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

A GLP-1 receptor agonist or mimetibody constructs or specified portion or variant of the present invention can include one or more amino acid substitutions, deletions or additions, either from natural mutations or human manipulation, as specified herein. Such or other sequences that can be used in the present invention, include, but are not limited to the following sequences presented in SEQ ID NOS:47-64.

A GLP-1 mimetibody constructs or specified portion or variant of the present invention can include one or more amino acid substitutions, deletions or additions, either from natural mutations or human manipulation, as specified herein. Such or other sequences that can be used in the present invention, include, but are not limited to the following sequences presented in Table 3, as shown corresponding to specified portions of SEQ ID NOS:47-64, where the partial variable region of the antibody sequence can be, but is not limited to, at least one portion of at least one of SEQ ID NOS:47-55, or fragment thereof as described in Table 3, further optionally comprising at least one substitution, insertion or deletion as further described in FIGS. 1-9 of PCT publication WO 05/05604 (PCT US04/19898) filed Jun. 24, 2004 and published Jan. 20, 2005, with corresponding SEQ ID NOS:1-9. The CH2, CH3 and hinge region can be, but not limited to, at least one portion of at least one of SEQ ID NOS:56-64, or fragment thereof as described in Table 3, further optionally comprising at least one substitution, insertion or deletion as further described in FIGS. 32-40 of PCT publication WO 05/05604 (PCT US04/19898) filed Jun. 24, 2004 and published Jan. 20, 2005, with corresponding SEQ ID NOS:32-40. Of course, the number of amino acid substitutions a skilled artisan would make depends on many factors, including those described above. Generally speaking, the number of amino acid substitutions, insertions or deletions for at least one of a GLP-1 receptor agonist or mimetibody constructs will not be more than 40, 30, 20, 19, 18, 17, 16, 15, 14, 13, 12, 11, 10, 9, 8, 7, 6, 5, 4, 3, 2, 1 amino acids, such as 1-30 or any range or value therein, as specified herein.

In formula I of the present invention ((P(n)-L(o)-V(p)-H (q)-CH2(r)-CH3(s))(t), the V, H, CH2, CH3 portions according to Formula I can be any suitable human or human compatable sequence, e.g., as presented in Table 3, where the partial variable region of the antibody sequence can be, but is not limited to, at least one portion of at least one of SEQ ID NOS:47-55, or fragment thereof as described in Table 3, further optionally comprising at least one substitution, insertion or deletion as further described in FIGS. 1-9 of PCT publication WO 05/05604 (PCT US04/19898) filed Jun. 24, 2004 and published Jan. 20, 2005, with corresponding SEQ ID NOS:1-9; and where the CH2, CH3 and hinge region can be, but not limited to, at least one portion of at least one of SEQ ID NOS:56-64, or fragment thereof as described in Table 3, further optionally comprising at least one substitution, insertion or deletion as as further described in FIGS. 32-40 of PCT publication WO 05/05604 (PCT US04/19898) filed Jun. 24, 2004 and published Jan. 20, 2005, with corresponding SEQ ID NOS:32-40, or as known in the art, or any combination or consensus sequence thereof, or any fusion protein thereof, preferably of human origin or engineered to minimize immunogenicity when administered to humans.

The P portion can comprise at least one GLP-1 therapeutic peptide known in the art or described herein, such as, but not limited to those presented in SEQ ID NO:1, or any combination or consensus sequence thereof, or any fusion protein thereof. In a preferred embodiment, the P portion can comprise at least one GLP-1 peptide having the sequence of at least one of SEQ ID NO:6, or any combination or consensus sequence thereof, or any fusion protein thereof.

The optional linker sequence can be any suitable peptide linker as known in the art. Preferred sequences include any combination of G and S. e.g., X1-X2-X3-X4- . . . -Xn, where X can be G or S, and n can be 5-30. Non-limiting examples include GS, GGS, GGGS (SEQ ID NO:16), GSGGGS (SEQ ID NO:17), GGSGGGS (SEQ ID NO:18), GGSGGGSGG (SEQ ID NO:19) and GGGSGGGSGG (SEQ ID NO:20); and the like.

Amino acids in a GLP-1 receptor agonist or mimetibody constructs or specified portion or variant of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one protein related activity, as specified herein or as known in the art. Sites that are critical for GLP-1 receptor agonist or mimetibody constructs or specified portion or variant binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Mimetibody constructs or specified portions or variants of the present invention can comprise as the P portion of Formula (I), e.g. but not limited to, at least one portion of at least one of SEQ ID NOS:1 and 6. A GLP-1 receptor agonist or mimetibody constructs or specified portion or variant can further optionally comprise at least one functional portion of at least one polypeptide as P portion of Formula (I), at least 90-100% of at least on of SEQ ID NOS:1 and 6. Non-limiting variants that can enhance or maintain at least one of the listed activities above include, but are not limited to, any of the above polypeptides, further comprising at least one mutation corresponding to at least one substitution, insertion or deletion that does not significantly affect the suitable biological activities or functions of said GLP-1 receptor agonist or mimetibody constructs.

In one embodiment, the P amino acid sequence, or portion thereof, has about 90-100% identity (i.e., 90, 91, 92, 93, 94, 95, 96, 97, 98, 99, 100 or any range or value therein) to the corresponding amino acid sequence of the corresponding portion of at least one of SEQ ID NOS:1 and 6. Preferably, 90-100% amino acid identity (i.e., 90, 91, 92, 93, 94, 95, 96, 97, 98, 99, 100 or any range or value therein) is determined using a suitable computer algorithm, as known in the art.

Mimetibody constructs or specified portions or variants of the present invention can comprise any number of contiguous amino acid residues from a GLP-1 receptor agonist or mimetibody constructs or specified portion or variant of the present invention, wherein that number is selected from the group of integers consisting of from 10-100% of the number of contiguous residues in a GLP-1 receptor agonist or mimetibody constructs. Optionally, this subsequence of contiguous amino acids is at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, 5, 6, 7, 8, 9, 10, 11, 12, 13, 14, 15, 16, 17, 18, 19, 20, or more.

As those of skill will appreciate, the present invention includes at least one biologically active GLP-1 receptor agonist or mimetibody constructs or specified portion or variant of the present invention. Biologically active mimetibody constructs or specified portions or variants have a specific activity at least 20%, 30%, or 40%, and preferably at least 50%, 60%, or 70%, and most preferably at least 80%, 90%, or 95%-1000% of that of the native (non-synthetic), endogenous or related and known inserted or fused protein or specified portion or variant. Methods of assaying and quantifying measures of enzymatic activity and substrate specificity are well known to those of skill in the art.

In another aspect, the invention relates to human mimetibody constructs and ligand-binding fragments, as described herein, which are modified by the covalent attachment of an organic moiety. Such modification can produce a GLP-1 receptor agonist or mimetibody constructs or ligand-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified mimetibody constructs and ligand-binding fragments of the invention can comprise one or more organic moieties that are covalently bonded, directly or indirectly, to the GLP-1 receptor agonist or mimetibody constructs or specified portion or variant. Each organic moiety that is bonded to a GLP-1 receptor agonist or mimetibody constructs or ligand-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, a GLP-1 receptor agonist or mimetibody constructs modified by the covalent attachment of polylysine is encompassed by the invention. Hydrophilic polymers suitable for modifying mimetibody constructs of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the GLP-1 receptor agonist or mimetibody constructs of the invention has a molecular weight of about 800 to about 150,000 Daltons as a separate molecular entity. For example, $PEG_{2500}$, $PEG_{5000}$, $PEG_{7500}$, $PEG_{9000}$, $PEG_{10000}$, $PEG_{12500}$, $PEG_{15000}$, and $PEG_{20,000}$, wherein the subscript is the average molecular weight of the polymer in Daltons, can be used.

The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying mimetibody constructs of the invention can be saturated or can contain one or more units of unsaturation. Fatty acids that are suitable for modifying mimetibody constructs of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified human mimetibody constructs and ligand-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—.

Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified mimetibody constructs of the invention can be produced by reacting an human GLP-1 receptor agonist or mimetibody constructs or ligand-binding fragment with a modifying agent. For example, the organic moieties can be bonded to the GLP-1 receptor agonist or mimetibody constructs in a non-site specific manner by employing an amine-reactive modifying agent, for example, an NHS ester of PEG. Modified human mimetibody constructs or ligand-binding fragments can also be prepared by reducing disulfide bonds (e.g., intra-chain disulfide bonds) of a GLP-1 receptor agonist or mimetibody constructs or ligand-binding fragment. The reduced GLP-1 receptor agonist or mimetibody constructs or ligand-binding fragment can then be reacted with a thiol-reactive modifying agent to produce the modified GLP-1 receptor agonist or mimetibody constructs of the invention. Modified human mimetibody constructs and ligand-binding fragments comprising an mimetibody constructs or specified portion or variant of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

GLP-1 Mimetibody Constructs Compositions. The present invention also provides at least one GLP-1 receptor agonist or mimetibody constructs or specified portion or variant composition comprising at least one, at least two, at least three, at least four, at least five, at least six or more mimetibody constructs or specified portions or variants thereof, as described herein and/or as known in the art that are provided in a non-naturally occurring composition, mixture or form. Such composition percentages are by weight, volume, concentration, molarity, or molality as liquid or dry solutions, mixtures, suspension, emulsions or colloids, as known in the art or as described herein.

Such compositions can comprise 0.00001-99.9999 percent by weight, volume, concentration, molarity, or molality as liquid, gas, or dry solutions, mixtures, suspension, emulsions or colloids, as known in the art or as described herein, on any range or value therein, such as but not limited to 0.00001, 0.00003, 0.00005, 0.00009, 0.0001, 0.0003, 0.0005, 0.0009, 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, 5, 6, 7, 8, 9, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9%. Such compositions of the present invention thus include but are not limited to 0.00001-100 mg/ml and/or 0.00001-100 mg/g.

The GLP-1 mimitibody composition can optionally further comprise an effective amount of at least one compound or protein selected from at least one of a diabetes drug, an insulin metabolism related drug, a glucose metabolism related drug, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplactic, an immunomodulation drug, an ophthalmic, otic or nasal drug, a topical drug, a nutritional drug or the like. Such drugs are well known in the art, including formulations, indications, dosing and administration for each presented herein (see e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The obesity, insulin sensitivity or lipid profile related drug can be at least one of a fat catabolic compound or treatment, caffeine, glitazones, insulin and derivatives, sulfonylureas, meglitinides, biguanides, alpha-glucosidase inhibitors, protein tyrosine phosphastase-1B, glycogen synthase kinase 3, gluconeogenesis inhibitors, pyruvate dehydrogenase kinase (PDH) inhibitors, lipolysis inhibitors, fat oxidation inhibitors, carnitine palmitoyltransferase I and/or II inhibitors, beta-3 adrenoceptor agonists, sodium and glucose cotransporter (SGLT) inhibitors, or compounds that act on one or more of at least one of: autoimmune suppression, immune regulation, activation, proliferation, migration and/or suppressor cell function of T-cells, inhibition of T cell receptor/peptide/MHC-II interaction, Induction of T cell anergy, deletion of autoreactive T cells, reduction of trafficking across blood brain barrier, alteration of balance of pro-inflammatory (Th1) and immunomodulatory (Th2) cytokines, inhibition of matrix metalloprotease inhibitors, neuroprotection, reduction of gliosis, promotion of re-myelination The at least one antacid, adsorbents, or antiflatulents can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizers can be at least one selected from pancreatin, pancrelipase, and ursodiol. The at least one antidiarrheal can be at least one selected from attapulgite, bismuth subsalicylate, calcium polycarbophil, diphenoxylate hydrochloride or atropine sulfate, loperamide, octreotide acetate, opium tincture, opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, sucralfate. (See, e.g., pp. 643-95 of Nursing 2001 Drug Handbook.) The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, troglitazone. The at least one thyroid hormone can be at least one selected from levothyroxine sodium, liothyronine sodium, liotrix, thyroid.

The at least one thyroid hormone antagonist can be at least one selected from methimazole, potassium iodide, potassium iodide (saturated solution), propylthiouracil, radioactive iodine (sodium iodide $^{131}$I), strong iodine solution. The at least one pituitary hormone can be at least one selected from corticotropin, cosyntropin, desmophressin acetate, leuprolide acetate, repository corticotropin, somatrem, somatropin, vasopressin. The at least one parathyroid-like drug can be at least one selected from calcifediol, calcitonin (human), calcitonin (salmon), calcitriol, dihydrotachysterol, etidronate disodium. (See, e.g., pp. 696-796 of Nursing 2001 Drug Handbook.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), sodium chloride. The at least one acidifier or alkalinizer can be at least one selected from sodium bicarbonate, sodium lactate, tromethamine. (See, e.g., pp. 797-833 of Nursing 2001 Drug Handbook.)

The at least one hematinic can be at least one selected from ferrous fumarate, ferrous gluconate, ferrous sulfate, ferrous sulfate (dried), iron dextran, iron sorbitol, polysaccharide-iron complex, sodium ferric gluconate complex. The at least one anticoagulant can be at least one selected from ardeparin sodium, dalteparin sodium, danaparoid sodium, enoxaparin sodium, heparin calcium, heparin sodium, warfarin sodium. The at least one blood derivative can be at least one selected from albumin 5%, albumin 25%, antihemophilic factor, anti-inhibitor coagulant complex, antithrombin III (human), factor IX (human), factor IX complex, plasma protein fractions. The at least one thrombolytic enzyme can be at least one selected from alteplase, anistreplase, reteplase (recombinant), streptokinase, urokinase. (See, e.g., pp. 834-66 of Nursing 2001 Drug Handbook.)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, zinc. The at least one calorics can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, medium-chain triglycerides. (See, e.g., pp. 1137-63 of Nursing 2001 Drug Handbook.)

GLP-1 receptor agonist or mimetibody constructs or specified portion or variant compositions of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences*, 18$^{th}$ Edition, Mack Publishing Co. (Easton, Pa.) 1990. Pharmaceutically acceptable carriers can be routinely selected that are suitable for the mode of administration, solubility and/or stability of the GLP-1 receptor agonist or mimetibody composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/GLP-1 receptor agonist or mimetibody constructs or specified portion or variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

GLP-1 receptor agonist or mimetibody constructs compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, the GLP-1 receptor agonist or mimetibody constructs or specified portion or variant compositions of the invention can include polymeric excipients/additives such as polyvinylpyrrolidones, ficolls (a polymeric sugar), dextrates (e.g., cyclodextrins, such as 2-hydroxypropyl-?-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the GLP-1 receptor agonist or mimetibody constructs compositions according to the invention are known in the art, e.g., as listed in "Remington: The Science & Practice of Pharmacy", 19th ed., Williams & Williams, (1995), and in the "Physician's Desk Reference", $52^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations. As noted above, the invention provides for stable formulations, which can preferably include a suitable buffer with saline or a chosen salt, as well as optional preserved solutions and formulations containing a preservative as well as multi-use preserved formulations suitable for pharmaceutical or veterinary use, comprising at least one GLP-1 receptor agonist or mimetibody constructs or specified portion or variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, 5.0 or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one GLP-1 receptor agonist or mimetibody constructs or specified portion or variant with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one GLP-1 receptor agonist or mimetibody constructs or specified portion or variant, and a second vial comprising an aqueous diluent of prescribed buffer or preservative, wherein said packaging material comprises a label that instructs a patient to reconstitute the at least one GLP-1 receptor agonist or mimetibody constructs or specified portion or variant in the aqueous diluent to form a solution that can be held over a period of twenty-four hours or greater.

The at least one GLP-1 receptor agonist or mimetibody constructs or specified portion or variant used in accordance with the present invention can be produced by recombinant means, including from mammalian cell or transgenic preparations, or can be purified from other biological sources, as described herein or as known in the art.

The range of amounts of at least one GLP-1 receptor agonist or mimetibody constructs or specified portion or variant in the product of the present invention includes amounts yielding upon reconstitution, if in a wet/dry system, concentrations from about 0.1 µg/ml to about 100 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic? polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one GLP-1 receptor agonist or mimetibody constructs or specified portion or variant and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one GLP-1 mimetibody constructs or specified portion or variant and preservative in an aqueous diluent is carried out using conventional dissolution and mixing procedures. To prepare a suitable formulation, for example, a measured amount of at least one GLP-1 receptor agonist or mimetibody constructs or specified portion or variant in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed formulations can be provided to patients as clear solutions or as dual vials comprising a vial of lyophilized at least one GLP-1 receptor agonist or mimetibody constructs or specified portion or variant that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40? C and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to at least one of 1-12 months, one-half, one and a half, and/or two years.

The solutions of at least one GLP-1 receptor agonist or mimetibody constructs or specified portion or variant in the invention can be prepared by a process that comprises mixing at least one GLP-1 receptor agonist or mimetibody constructs or specified portion or variant in an aqueous diluent. Mixing is carried out using conventional dissolution and mixing procedures. To prepare a suitable diluent, for example, a measured amount of at least one GLP-1 receptor agonist or mimetibody constructs or specified portion or variant in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed products can be provided to patients as clear solutions or as dual vials comprising a vial of lyophilized at least one GLP-1 receptor agonist or mimetibody constructs or specified portion or variant that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one GLP-1 receptor agonist or mimetibody constructs or specified portion or variant that is reconstituted with a second vial containing the aqueous diluent. The clear solution in this case can be up to one liter or even larger in size, providing a large reservoir from which smaller portions of the at least one GLP-1 receptor agonist or mimetibody constructs or specified portion or variant solution can be retrieved one or multiple times for transfer into smaller vials and provided by the pharmacy or clinic to their customers and/or patients.

Recognized devices comprising these single vial systems include those pen-injector devices for delivery of a solution such as Humaject?, NovoPen?, B-D®Pen, AutoPen?, and OptiPen?. Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one GLP-1 receptor agonist or mimetibody constructs or specified portion or variant in the aqueous diluent to form a solution and to use the solution over a period of 2-24 hours or greater for the two—vial, wet/dry, product. For the single-vial solution product, the label indicates that such solution can be used over a period of 2-96 hours or greater. The presently claimed products are useful for human pharmaceutical product use.

The formulations of the present invention can be prepared mimetibody constructs or specified portion or variant and a selected buffer, preferably a phosphate buffer containing saline or a chosen salt. Mixing the at least one GLP-1 receptor agonist or mimetibody constructs or specified portion or variant and buffer in an aqueous diluent is carried out using conventional dissolution and mixing procedures. To prepare a suitable formulation, for example, a measured amount of at least one GLP-1 receptor agonist or mimetibody constructs or specified portion or variant in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one GLP-1 receptor agonist or mimetibody constructs or specified portion or variant that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one GLP-1 receptor agonist or mimetibody constructs or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications. The present invention provides a method of increasing the function of pancreas, comprising administering an effective amount of at least one GLP-1 receptor agonist or mimetibody constructs composition to a cell, tissue, organ, or individual in need thereof. The GLP-1 receptor agonist or mimetibody constructs may promote islet differentiation, increase □-cell mass, and/or increase insulin secretion. The GLP-1 receptor agonist or mimetibody constructs can be administered in vitro, ex vivo, or in vivo.

For example, GLP-1 receptor agonist or mimetibody constructs treatment can be used in pancreas or islet transplantation patients or other cell therapies involving insulin-producing cells. Cell therapies may be delivered to the patient intravenously, subcutaneously, intramuscularly, or intraperitoneally, with or without the support of a device designed to enhance cell survival or prevent immune rejection. It can also be used in patients following surgical removal of a portion of the pancreas. GLP-1 receptor agonist or mimetibody constructs can be administered to living pancreas or islet donors to increase □-cell mass and function of pancreas prior to or after the procedure. It can also be used to stimulate the proliferation of □-cells in vitro prior to the transplantation, thereby increasing the □-cell mass and preventing the apoptosis of the islets once transplanted. It can further be used in culture of stem, progenitor, or precursor of insulin-producing cells to stimulate the differentiation and proliferation and for the prevention of apoptosis.

The present invention provides a method delaying the onset of or preventing diabetes in individuals at high risk to become diabetic, comprising administering an effective amount of at least one GLP-1 receptor agonist or mimetibody constructs composition to an individual in need thereof.

The present invention provides a method for modulating or treating at least one provides a method for modulating or treating at least one diabetes associated immune related disease, in a cell, tissue, organ, animal, or patient including, but not limited to, at least one of type I or type II diabetes mellitus, including adult onset or juvenile, insulin dependent, non-insulin dependent, and the like, including the associated signs and symptoms, such as but not limited to, insulin resistance, hyperglycemia, hypoglycemia, Cushing's syndrome, acanthosis nigricans, lipoatrrophic diabetes, retinopathy, nephropathy, polyneuropathy, mononeuropathy, autonomic neuropathy, ulcers, foot ulcers, joint problems, infections (e.g., fungal or bacterial), and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2001), each entirely incorporated by reference. Other non-limiting pancreatic disorders include pancreatitis, pancreatic tumors, or pancreatic cancer.

The present invention provides a method for modulating or treating at least one metabolic disorder that results in hyperglycemia. Non-limiting examples of such disorders include cirrhosis and impaired glucose tolerance associated with hypertension. The GLP-1 receptor agonist or mimetibody constructs treatment can also be used in conjunction with other medications known to induce hyperglycemia and/or diabetes. Non-limiting examples of such medications include immunosuppressive drugs such as cyclosporine or FK-506 given in organ transplantation, protease inhibitors prescribed for patients with AIDS, and atypical antipsychotics used in the treatment of schizophrenia.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one GLP-1 receptor agonist or mimetibody constructs or specified portion or variant to a cell, tissue, organ, animal or patient in need of such modulation, treatment or therapy.

Any method of the present invention can comprise administering an effective amount of a composition or pharmaceutical composition comprising at least one GLP-1 receptor agonist or mimetibody constructs or specified portion or variant to a cell, tissue, organ, animal or patient in need of such modulation, treatment or therapy. Such a method can optionally further comprise co-administration or combination therapy, wherein the administering of said at least one GLP-1 receptor agonist or receptor agonist or mimetibody constructs, specified portion or variant thereof, further comprises administering, before concurrently, and/or after, at least one selected from at least one of a diabetes or insulin metabolism related drug, a TNF antagonist (e.g., but not limited to a TNF antibody or fragment, a soluble TNF receptor or fragment, fusion proteins thereof, or a small molecule TNF antagonist), an antirheumatic, a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., GLP-letin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Cytokines include, but are not limited to all known cytokines. See, e.g., CopewithCytokines.com. Cytokine antagonists include, but are not limited to, any antibody, fragment or mimetic, any soluble receptor, fragment or mimetic, any small molecule antagonist, or any combination thereof.

Typically, treatment of pathologic conditions is effected by administering an effective amount or dosage of at least one GLP-1 receptor agonist or mimetibody constructs or GLP-1 receptor agonist composition that total, on average, a range from at least about 0.0001 to 500 milligrams of at least one GLP-1 receptor agonist or mimetibody constructs or specified portion or variant/kilogram of patient per dose, and preferably from at least about 0.001 to 100 milligrams GLP-1 receptor agonist or mimetibody constructs or specified portion or variant/kilogram of patient per single or multiple administration, depending upon the specific activity of contained in the composition. Alternatively, the effective serum concentration can comprise 0.001-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.0001, 0.0002, 0.0003, 0.0004, 0.0005. 0.0006, 0.0007, 0.0008, 00009, 0.001, 0.002, 0.003, 0.004, 0.005, 0.006, 0.007, 0.008, 0.009, 0.01, 0.02, 0.03, 0.04, 0.05. 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, and/or 30 mg/kg/administration, or any range, value or fraction thereof, or to achieve a serum concentration of 0.0001, 0.0002, 0.0003, 0.0004, 0.0005, 0.0006, 0.0007, 0.0008, 00009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.0001 to 100 milligrams per kilogram of body weight. Ordinarily 0.001 to 10, and preferably 0.001 to 1 milligrams per kilogram per administration or in sustained release form is effective to obtain desired results.

As a non-limiting example, treatment of humans or animals can be provided as a one-time or periodic dosage of at least one GLP-1 receptor agonist or mimetibody constructs or specified portion or variant of the present invention 0.0001 to 100 mg/kg, such as 0.0002, 0.0003, 0.0004, 0.0005, 0.0006, 0.0007, 0.0008, 00009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.9, 1.0, 1.1, 1.5, 2, 3, 4, 5, 6, 7, 8, 9, or 10 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single, infusion or repeated doses.

Dosage forms (composition) suitable for internal administration generally contain from about 0.0001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the GLP-1 receptor agonist or mimetibody constructs or specified portion or variant can be formulated as a solution, suspension, emulsion or lyophilized powder in association, or separately provided, with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Therapeutic Administration. Many known and developed modes of can be used for administering pharmaceutically effective amounts of at least one GLP-1 receptor agonist or mimetibody constructs or specified portion or variant according to the present invention. A GLP-1 receptor agonist or mimetibody constructs of the present invention can be delivered in a carrier, as a solution, emulsion, colloid, or suspension, or as a powder, using any of a variety of devices and methods suitable for administration by inhalation or other modes described here within or known in the art.

Parenteral Formulations and Administration. Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqouus solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or triglycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery. The invention further relates to the administration of at least one GLP-1 receptor agonist or mimetibody constructs or specified portion or variant by parenteral, subcutaneous, intramuscular, intravenous, bolus, vaginal, rectal, buccal, sublingual, intranasal, or transdermal means. Protein, GLP-1 receptor agonist or mimetibody constructs or specified portion or variant compositions can be prepared for use for parenteral (subcutaneous, intramuscular or intravenous) administration particularly in the form of liquid solutions or suspensions; for use in vaginal or rectal administration particularly in semisolid forms such as creams and suppositories; for buccal, or sublingual administration particularly in the form of tablets or capsules; or intranasally particularly in the form of powders, nasal drops or aerosols or certain agents; or transdermally particularly in the form of a gel, ointment, lotion, suspension or patch delivery system (e.g., but not limited to, Macroflux™ by Alza, Calif., USA, or any other know methods, devices or techniques) with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration. For pulmonary administration, preferably at least one GLP-1 receptor agonist or mimetibody constructs or specified portion or variant composition is delivered in a particle size effective for reaching the lower airways of the lung or sinuses. According to the invention, at least one GLP-1 receptor agonist or mimetibody constructs or specified portion or variant can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of GLP-1 receptor agonist or mimetibody constructs or specified portion or variants are also known in the art. All such devices can use of formulations suitable for the administration for the dispensing of GLP-1 receptor agonist or mimetibody constructs or specified portion or variant in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one GLP-1 receptor agonist or mimetibody constructs or specified portion or variant is delivered by a dry powder inhaler or a sprayer. There are a several desirable features of an inhalation device for administering at least one GLP-1 receptor agonist or mimetibody constructs or specified portion or variant of the present invention. For example, delivery by the inhalation device is advantageously reliable, reproducible, and accurate. The inhalation device can optionally deliver small dry particles, e.g. less than about 10 ?m, preferably about 1-5 ?m, for good respirability.

Administration of GLP-1 Receptor agonist or mimetibody constructs or specified portion or variant Compositions as a Spray. A spray including GLP-1 receptor agonist or mimetibody constructs or specified portion or variant composition protein can be produced by forcing a suspension or solution of at least one GLP-1 receptor agonist or mimetibody constructs or specified portion or variant through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one GLP-1 receptor agonist or mimetibody constructs or specified portion or variant composition protein delivered by a sprayer have a particle size less than about 10 ?m, preferably in the range of about 1 μm to about 5 μg, and most preferably about 2 μm to about 3 μm.

Formulations of at least one GLP-1 receptor agonist or mimetibody constructs or specified portion or variant composition protein suitable for use with a sprayer typically include GLP-1 receptor agonist or mimetibody constructs or specified portion or variant composition protein in an aqueous solution at a concentration of about 1 mg to about 20 mg of at least one GLP-1 receptor agonist or receptor agonist or mimetibody constructs or specified portion or variant composition protein per ml of solution. The formulation can include agents such as an excipient, a buffer, an isotonicity agent, a preservative, a surfactant, and, preferably, zinc. The formulation can also include an excipient or agent for stabilization of the GLP-1 receptor agonist or mimetibody constructs or specified portion or variant composition protein, such as a buffer, a reducing agent, a bulk protein, or a carbohydrate. Bulk proteins useful in formulating GLP-1 mimetibody constructs or specified portion or variant composition proteins include albumin, protamine, or the like. Typical carbohydrates useful in formulating GLP-1 receptor agonist or mimetibody constructs or specified portion or variant composition proteins include sucrose, mannitol, lactose, trehalose, glucose, or the like. The GLP-1 receptor agonist or mimetibody constructs or specified portion or variant composition protein formulation can also include a surfactant, which can reduce or prevent surface-induced aggregation of the GLP-1 receptor agonist or mimetibody constructs or specified portion or variant composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as mimetibody constructs, or specified portions or variants, can also be included in the formulation.

Administration of GLP-1 receptor Agonist or Mimetibody Constructs or Specified Portion or Variant Compositions by a Nebulizer. GLP-1 receptor agonist or mimetibody constructs or specified portion or variant composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of GLP-1 receptor agonist or mimetibody constructs or specified portion or variant composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of the GLP-1 receptor agonist or mimetibody constructs or specified portion or variant composition protein either directly or through a coupling fluid, creating an aerosol including the GLP-1 receptor agonist or mimetibody constructs or specified portion or variant composition protein. Advantageously, particles of GLP-1 receptor agonist or mimetibody constructs or specified portion or variant composition protein delivered by a nebulizer have a particle size less than about 10 μm, preferably in the range of about 1 μg to about 5 μm, and most preferably about 2 μm to about 3 μm.

Formulations of at least one GLP-1 receptor agonist or mimetibody constructs or specified portion or variant suitable for use with a nebulizer, either jet or ultrasonic, typically include GLP-1 receptor agonist or mimetibody constructs or specified portion or variant composition protein in an aqueous solution at a concentration of about 1 μg to about 20 mg of at least one GLP-1 mimetibody constructs or specified portion or variant protein per ml of solution. The formulation can include agents such as an excipient, a buffer, an isotonicity agent, a preservative, a surfactant, and, preferably, zinc. The formulation can also include an excipient or agent for stabilization of the at least one GLP-1 receptor agonist or mimetibody constructs or specified portion or variant composition protein, such as a buffer, a reducing agent, a bulk protein, or a carbohydrate. Bulk proteins useful in formulating at least one GLP-1 receptor agonist or mimetibody constructs or specified portion or variant composition proteins include albumin, protamine, or the like. Typical carbohydrates useful in formulating at least one GLP-1 receptor agonist or mimetibody constructs or specified portion or variant include sucrose, mannitol, lactose, trehalose, glucose, or the like. The at least one GLP-1 receptor agonist or mimetibody constructs or specified portion or variant formulation can also include a surfactant, which can reduce or prevent surface-induced aggregation of the at least one GLP-1 receptor agonist or mimetibody constructs or specified portion or variant caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as at least one GLP-1 receptor agonist or mimetibody constructs or specified portion or variant protein can also be included in the formulation.

Administration of GLP-1 Receptor Agonist or Mimetibody Constructs or Specified Portion or Variant Compositions By A Metered Dose Inhaler. In a metered dose inhaler (MDI), a propellant, at least one GLP-1 receptor agonist or mimetibody constructs or specified portion or variant, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of GLP-1 receptor agonist or mimetibody constructs or specified portion or variant composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one GLP-1 receptor agonist or mimetibody constructs or specified portion or variant for use with a metered-dose inhaler device will generally include a finely divided powder containing at least one GLP-1 receptor agonist or mimetibody constructs or specified portion or variant as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one GLP-1 receptor agonist or mimetibody constructs or specified portion or variant as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one GLP-1 receptor agonist or mimetibody constructs or specified portion or variant compositions via devices not described herein.

Mucosal Formulations and Administration. For absorption through mucosal surfaces, compositions and methods of administering at least one GLP-1 receptor agonist or mimetibody constructs or specified portion or variant include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Oral Formulations and Administration. Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations may contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat. No. 5,879,681 and U.S. Pat. No. 5,871,753 are used to deliver biologically active agents orally are known in the art.

Transdermal Formulations and Administration. For transdermal administration, the at least one GLP-1 receptor agonist or mimetibody constructs or specified portion or variant is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations. It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770, 222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLE 1

Cloning and Expression of a GLP-1 Mimetibody Constructs in Mammalian Cells. A typical mammalian expression vector contains at least one promoter element, which mediates the initiation of transcription of mRNA, the GLP-1 mimetibody constructs or specified portion or variant coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded GLP-1 mimetibody constructs or specified portion or variant. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279

(1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of GLP-1 mimetibody constructs or specified portion or variants.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells. The vector pC4 is used for the expression of GLP-1 mimetibody constructs or specified portion or variant. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the GLP-1 in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete GLP-1 mimetibody constructs or specified portion or variant is used, corresponding to HC and LC variable regions of a GLP-1 mimetibody constructs of the present invention, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 µg of the expression plasmid pC4 is cotransfected with 0.5 µg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 µg/ml G418. After 2 days, the cells are trypsinized and seeded in hybridoma cloning plates (Greiner, Germany) in alpha minus MEM supplemented with 10, 25, or 50 ng/ml of methotrexate plus 1 µg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

EXAMPLE 2

Non-Limiting Example of a GLP-1 Mimetibody Constructs of the Invention. GLP-1 is a 37-amino acid peptide secreted from the L-cells of the intestine following an oral glucose challenge. A mimetibody constructs construct incorporating a biologically active GLP-1 (7-37) peptide, variant or derivative is expected to prolong the in vivo lifetime of the peptide and provide a novel therapy for lowering blood glucose in Type 2 diabetic patients. Peptides encoding the native GLP-1 (7-37) peptide or a DPP-IV resistant analogue can be incorporated into the mimetibody constructs scaffold. Several of these molecules have been made, and the resulting mimetibody constructs have demonstrated activity in functional in vitro cell-based assays. It should be noted that different in vitro assays and in vivo models can be used in these studies and the potencies may not be comparable to each other or to results presented herein.

To generate GLP-1 mimetibody constructs variants, the GLP-1 peptide, the linker, the hinge, or the CH2 and CH3 sequences in the mimetibody constructs could be deleted, added, substituted, mutated or modified to improve expression, potency, stability, or effector functions.

The wild-type GLP-1 sequence as well as DPP-IV resistant GLP-1 variants, such as GLP-1 (A2S) or GLP-1 (A2G) can be incorporated into a mimetibody constructs scaffold. Mutations of the peptide could be made to improve the properties of a GLP-1 mimetibody constructs. For example mutations in the amino terminal residues may improve signaling while mutations in the helical domain may stabilize the helix and thereby improve binding to the receptor and/or stability of the mimetibody constructs.

The length and composition of the linker could be mutated to vary the flexibility or stability of the attachment between the GLP-1 peptide and the Fc region. Different isotypes could be incorporated into the hinge region of the molecule. In addition, mutations could be made within the hinge region of the mimetibody constructs to stabilize the molecule. For example, the human IgG4 hinge could be mutated to make the $Ser^{228}$->Pro variant, to stabilize the interchain disulfide bonds in the mimetibody constructs. Variations within the Fc portion of the mimetibody constructs could be made to improve the stability of the molecule and to change effector functions such as FcR binding. For example, one could use human or murine isotypes (or variations of these molecules) such as IgG4 with Ala/Ala mutations.

GLP-1 Mimetibody Constructs of the Present Invention. A specific, non-limiting, example of this invention is the GLP-1 mimetibody constructs (amino acid SEQ ID NO:2, 4 or 70, corresponding to DNA SEQ IDS:1, 3 and 69)) according to Formula (I):

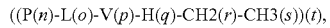

where P is a single copy of the bioactive GLP-1 peptide (7-36), L is a tandem repeat of either Gly-Ser or Gly-Gly-Gly-Ser flexible linker, V is the C-terminal of $V_H$ sequence, i.e., the J region of a naturally occurring IgG, H is the complete IgG1 hinge region and CH2 & CH3 are of the IgG1 isotype subclass. It is expected that the half-life of this construct will be many times that of the GLP-1 peptide alone or its variant or derivative and similar to that of an IgG.

In addition to the basic structure described above, variants with potentially favorable biological characteristics are described. These include constructs that may have a decreased tendency to self-associate, reduced immune effector functions or decreased immunogenicity. Other modifications that confer desired characteristics such as improved conformation of the biologically active peptide, and transfer across the blood-brain barrier are envisioned. The proposed variants and modifications may be combined in any fashion to yield constructs with desired activities.

Using recombinant DNA methods, the GLP-1 peptide was inserted into an intermediate vector between an immunoglobulin signal peptide and a human J sequence. This was done using complementary synthetic oligonucleotides with ends compatible with the restriction sites present in the vector. These oligonucleotides comprised coding sequences for the GLP-1 peptide, and a flexible linker composed of two GGGS repeats. A restriction fragment containing the above-mentioned functional elements was then transferred into an expression vector. This vector contained the anti-CD4 immunoglobulin promoter and enhancer, and the coding sequence for the human IgG1 hinge sequence, HC constant region 2 (CH2) and constant region 3 (CH3) as well as the necessary elements for plasmid replication and selection in bacteria and selection for stable expressers in mammalian cells.

This plasmid was introduced into the HEK293E cells and expression of the wt GLP-1 MMB was achieved in transiently transfected cells. Purification of GLP-1 MMB was accomplished by standard protein A and Superose 12 affinity chromatography, yielding approximately 1.5 mg/L of transfected cells. This protein was the starting material for the experiments described below.

The amino acid sequence of an exemplary GLP-1 mimetibody constructs are SEQ ID NOS:2, 4 and 70). Functional domains are annotated above the peptide coding sequence. It is thought that the J sequence will provide even more flexibility to allow the GLP-1 dimer to assume the proper conformation, and allow the dimer to protrude from the globular structure of the immunoglobulin and penetrate into the cleft between two GLP-1 receptors. There are three cysteines in the IgG1 hinge region. The first would normally pair to the immunoglobulin light chain (LC) and the other two participate in interchain bonds between two HCs. CH2 and CH3 regions constitute the bulk of the protein. One of the reasons that immunoglobulins are believed to have a long serum half-life is their ability to bind the FcRn that extends the serum half-life by returning pinocytosed immunoglobulin back to the extracellular space. The binding site of the FcRn overlaps the junction of the CH2 and CH3 regions (Sheilds et al, 2001, J. Biol. Chem., vol. 276 (9), 6591-6604).

It is well known that two IgG heavy chains are assembled during cellular processing via disulfide bonds between cysteines located in the hinge region to form a homodimer. It is expected that this will also occur between the modified peptides to form the assembled GLP-1 mimetibody constructs. In addition, it is expected that the intrachain disulfide bond between the two cysteines in the GLP-1 peptide will also form. The expected structure of GLP-1 mimetibody constructs contains two GLP-1 peptides. The spatial arrangement of the peptides at the N-terminus along with the flexibility of adjoining sequences should allow the peptides to form the bioactive dimer.

EXAMPLE 3

FACS Binding Assay. The activity of GLP-1 mimetibody constructs was tested in an in vitro FACS binding assay. To determine whether the GLP-1 MMB binds the GLP-1R, HEK293 cells ($1 \times 10^6$ cells) over-expressing the GLP-1R were incubated with GLP-1 MMB (20 nM) for 2 hours at 4° C. The cells were washed, and a fluorescently labeled secondary detection antibody (1 µg/mL goat anti-human IgG, Fc gamma specific) was added for 30 minutes at 4° C. The fluorescence intensity of the cells was monitored via flow cytometry. GLP-1 MMB binds to HEK293 cells over-expressing the GLP-1R. GLP-1 MMB does not bind to the control HEK293 cells. GLP-1 peptide analogue (A2S) is able to compete with GLP-1 MMB for binding to HEK293 cells over-expressing the GLP-1R.

EXAMPLE 4 cAMP Assay. GLP-1 binds to its receptor, a G-protein coupled receptor, resulting in a dose-dependent increase in the signaling molecule, 3',5'-cyclic AMP (cAMP). cAMP can be measured with an in vitro assay in cells expressing the GLP-1R (Applied Biosystems). Briefly, Rinm cells (100,000 cells) were incubated with increasing concentrations of GLP-1 peptide (0-30 nM) or GLP-1 MMB (0-100 nM). The cells were lysed, and the amount of cAMP was determined using a competitive assay that employs an alkaline-phosphatase labeled cAMP conjugate and a chemiluminescent substrate (Tropix® CDPD®). The concentration dependent cAMP activity for the wt GLP-1 MMB is comparable to the GLP-1 peptide ($EC_{50}$=11 nM vs. 0.4 nM, respectively). In a similar experiment, GLP-1 (A2G) MMB in IgG4 scaffold and GLP-1 (A2S) MMB in IgG4 scaffold both increased cAMP levels in Rinm cells to a significantly higher level than wt GLP-1 MMB in IgG4 scaffold

EXAMPLE 5

DPP-IV Cleavage Assay. Since GLP-1 is rapidly inactivated by DPP-IV, an in vitro assay was established to quantitate intact (i.e. uncleaved) GLP-1 MMB. Briefly, GLP-1 MMB or peptide (1.2 nM) was incubated at room temperature with DPP-IV (1 μg/mL, R&D Systems). After various times (0, 5, 10, 15, 20, 30, 40 minutes), a DPP-IV inhibitor (100 μM, Linco) was added to quench the reaction. The amount of intact GLP-1 MMB or peptide was measured using the GLP-1 Active ELISA (Linco) and the GLP-1 MMB or peptides for the respective standard curves. The GLP-1 MMB was significantly more resistant to cleavage by DPP-IV, relative to the GLP-1 peptide.

EXAMPLE 6

Human Serum Stability Assay. The stability of the GLP-1 MMB in serum was also measured to ensure that other serum proteases were not able to cleave and inactivate the GLP-1 MMB. Briefly, GLP1 peptide or the GLP1 MMB (30 nM) was incubated in human serum at 37° C. After various times, the reactions were quenched with a DPP-IV inhibitor (100 μM, Linco), and the samples were analyzed using the GLP-1 Active ELISA from Linco. The GLP-1 MMB is stable in human serum for 24 hours while the peptide is decayed rapidly.

EXAMPLE 7

GLP-1 MMB Causes Insulin Secretion in RINm Cells. To test the effect of GLP-1 MMB in insulin secretion, RINm cells were treated with increasing concentrations of GLP-1 (7-36) peptide (0-5 nM), exendin-4 peptide (0-5 nM), or various GLP-1 mimetibody constructs (5 or 50 nM) and the amount of insulin secreted was measured via ELISA. All GLP-1 MMBs tested had activities in stimulating insulin secretion in RINm cells. At 50 nM, the MMBs had activities comparable to that of the wide-type GLP-1 (7-36) peptide.

EXAMPLE 8

GLP-1 MMB Lowers Glucose Level in db/db Mice. Six week old db/db mice were fasted for two hours and then dosed intravenously with vehicle, GLP-1 peptide, or GLP-1 (A2S) MMB. Blood glucose was monitored 0.5, 1, 2, 3, and 4 hours post-dosing. The GLP-1 peptide lowered blood glucose at 30 minutes, but by 60 minutes, the blood glucose began to increase again likely due to the short half-life of the GLP-1 peptide. In comparison, GLP-1 (A2S) MMB at a dose 100-fold lower than the GLP-1 peptide dose induced a decrease in blood glucose throughout the entire 4 hour period. In addition, the decrease in blood glucose was dose dependent.

EXAMPLE 9

Pharmacokinetics of GLP-1 MMBs in Mice and in Cynomolgus Monkeys. To measure the pharmacokinetics of four GLP-1 mimetibody constructs (A2G, A2S, exedin-cap, and wt), C57/Bl6 mice were intravenously dosed with 1 mg/kg of the MMBs. Plasma was obtained via cardiac puncture after sacrificing mice at different time point. Various ELISAs were used to measure Fc, total MMB, active MMB, and acive peptide as they were metabolized in the animal. Active MMB reflects the intact N-terminus of the peptide still attached to the Fc region of the mimetibody constructs. Substitution of the second amino acid in the peptide (alanine) with either a serine or a glycine prolonged the lifetime of the active MMB in circulation.

Cynomolgus monkey were injected intravenously with 1.0 mg/kg of four different GLP-1 MMB constructs and serum samples were taken at different time points from 10 minutes to 5 days following dosing. Serum samples were evaluated by ELISA to quantify intact MMB. All four MMBs exhibit a rapid distribution phase, followed by a slower clearance phase. Pharmacokinetic constants were calculated for each of the constructs to indicate a $T^1/2$ of approximately 3 days with similar exposure determined by AUC from T=0 to T=120 hours.

EXAMPLE 10

Intracerebroventricular (icv) Dosing of CNTO 736 to Normal Rats Demonstrating Evidence Supporting Treatment for Insulin Sensitivity or Lipid Profile. The effect of acute treatment of CNTO 736 (Table 4, SEQ ID NO:70) on insulin sensitivity and lipid metabolism was evaluated in C57Bl mice maintained on a high fat diet for 10 weeks (DIO mice). CNTO 736 (1.0 or 0.1 mg/kg), exendin-4 (7.1 μg/kg) or vehicle was administered by intra-peritoneal injection, and the hyperinsulinemic euglycemic clamp was conducted 2 hours post dosing. The effect of chronic treatment of CNTO 736 on insulin sensitivity and lipid metabolism was evaluated in C57Bl mice maintained on a high fat diet for 10 weeks. During weeks 7 through 10, mice were dosed daily by intra-peritoneal injection with CNTO 736 (1.0 or 0.1 mg/kg), exendin-4 (7.1 μg/kg), or vehicle and a hyperinsulinemic-euglycemic clamp was performed on all animal two hours after the last dose.

The hyperinsulinemic-euglycemic clamp was performed under Acepromazine (6.25 mg/kg)/Midazolam (6.25 mg/kg)/Fentanyl (0.3125 mg/kg) anaesthesia in the following manner. Mice had free access to high fat food and water until 10 hours prior to the clamp. Basal rates of glucose and glycerol turnover were determined by giving a primed (p) continuous (c) infusion of 14C-glucose (p: 0.2 μCi; c: 0.3 μCi/h, Amersham, Little Chalfont, U.K.) and 3H-glycerol (p: 0.6 ?Ci; c: 0.9 ?Ci/h, Amersham) for 60 minutes. Subsequently, insulin was administered in a primed (4.5 mU) continuous (6.8 mU/h) i.v. infusion for approximately 2 h to attain steady state circulating insulin levels of ~4 ng/ml. A variable infusion of a 12.5% D-glucose solution was used to maintain euglycemia, as determined at 10 min intervals via tail bleeding (<3 μl, Freestyle, TheraSense, Disetronic Medical Systems BV, Vianen, The Netherlands). Blood samples (60 μl) were drawn during the basal period (after 50 and 60 min) and during the clamp period (after 70, 80, and 90 min) to determine the plasma concentration of glucose, FFA, insulin, 14C-glucose and 3H-glycerol.

To quantify VLDL production, 500 mg of Triton WR-1339 (Sigma, St. Louis, Mo., USA) per kg body weight was injected i.v. as a 10% (w/w) solution in sterile saline to block serum VLDL clearance. Blood samples (20 μl) were taken at t=0, 10, 20, 40 and 60 minutes after injection to determine the concentration of plasma triglycerides (TG). VLDL-TG production was calculated from the slope of the concentration curve and expressed as gmol/kg/min. Turnover rates of glucose (μmol/min/kg) was calculated in basal and hyperinsulinemic conditions as the rate of tracer infusion (dpm/min) divided by the plasma specific activity of 14C-glucose (dpm/μmol). The ratio was corrected for body weight. Endogenous glucose production (EGP) was calculated as the difference between the tracer-derived rate of glucose appearance and the infusion rate of glucose. Glucose disposal was calculated based on the concentration of 14C-glucose normalized to infusion rate of glucose. The statistical significance (p<0.05) in various measures of glucose turnover and VLDL production among groups was tested by analysis of variance.

EXAMPLE 11

Body Weights, Plasma Glucose, Insulin, Glycerol and Fatty Acid Levels in DIO Mice in Basal and Hyperinsulinemic Conditions After Acute and Chronic Treatment with GLP-1 MMB. As shown in Table 1 body weights and plasma parameters did not change significantly following acute treatment with CNTO 736 or exendin-4 with exception of reduced glucose level in basal condition after administration of high dose of CNTO 736 and elevated insulin level in hyperinsulinemic condition in exendin-4-treated mice. Chronic treatment with the high dose of CNTO 736 induced significant weight loss in DIO mice (Table 2). Both doses of CNTO 736 and exendin-4 decreased fasting blood glucose level. Glycerol and fatty acid levels did not change in response to treatment.

TABLE 1

Body weights and plasma parameters in DIO mice that received a single i.p. injection of CNTO 736, exendin-4, or vehicle under basal or hyperinsulinemic conditions.

| | Basal | | | | Hyperinsulinemic | | | |
| --- | --- | --- | --- | --- | --- | --- | --- | --- |
| Acute | Vehicle | CNTO 736 1 mgk | CNTO 736 0.1 mgk | Exendin | Vehicle | CNTO 736 1 mgk | CNTO 736 0.1 mgk | Exendin |
| Body weight (g) | 30.9 ± 2.3 | 31.2 ± 2.2 | 31.3 ± 1.6 | 31.4 ± 0.9 | 30.9 ± 2.3 | 31.2 ± 2.2 | 31.3 ± 1.6 | 31.4 ± 0.9 |
| Glucose (mmol/l) | 6.2 ± 2.4 | 4.4 ± 1.0* | 5.5 ± 1.2 | 4.6 ± 1.1 | 7.2 ± 1.0 | 8.0 ± 0.8 | 7.3 ± 0.5 | 7.7 ± 0.9 |
| FFA (mmol/l) | 1.3 ± 0.6 | 1.1 ± 0.5 | 1.1 ± 0.5 | 1.0 ± 0.22 | 0.7 ± 0.3 | 0.6 ± 0.4 | 0.7 ± 0.3 | 0.5 ± 0.2 |
| Insulin (ng/ml) | 1.1 ± 0.7 | 0.9 ± 0.6 | 1.1 ± 0.8 | 0.7 ± 0.5 | 3.1 ± 1.3 | 4.5 ± 1.7 | 3.5 ± 1.3 | 4.4 ± 0.8* |
| Glycerol (mmol/l) | 0.2 ± 0.1 | 0.2 ± 0.1 | 0.2 ± 0.1 | 0.2 ± 0.1 | 0.1 ± 0.1 | 0.1 ± 0.1 | 0.1 ± 0.1 | 0.1 ± 0.0 |

Values represent mean ± SD for at least 8 mice per group.
*p < 0.05 vs. control.

TABLE 2

Body weights and plasma parameters in DIO mice that received chronic i.p. injections of CNTO 736, exendin-4, or vehicle under basal or hyperinsulinemic conditions.

| | Basal | | | | Hyperinsulinemic | | | |
| --- | --- | --- | --- | --- | --- | --- | --- | --- |
| Chronic | Vehicle | CNTO 736 1 mgk | CNTO 736 0.1 mgk | Exendin | Vehicle | CNTO 736 1 mgk | CNTO 736 0.1 mgk | Exendin |
| Body weight (g) | 27.3 ± 1.8 | 25.1 ± 1.3* | 26.1 ± 1.9 | 26.3 ± 2.0 | 27.3 ± 1.8 | 25.1 ± 1.3* | 26.1 ± 1.9 | 26.3 ± 2.0 |
| Glucose (mmol/l) | 6.0 ± 1.0 | 4.1 ± 0.8** | 4.3 ± 1.0** | 4.9 ± 1.1* | 6.9 ± 0.9 | 7.6 ± 0.9 | 7.6 ± 1.1 | 7.3 ± 0.9 |
| FFA (mmol/l) | 1.1 ± 0.3 | 1.1 ± 0.2 | 1.1 ± 0.3 | 1.0 ± 0.3 | 0.5 ± 0.2 | 0.4 ± 0.1 | 0.5 ± 0.1 | 0.4 ± 0.1 |
| Insulin (ng/ml) | 1.0 ± 0.7 | 1.4 ± 1.3 | 1.1 ± 0.6 | 1.4 ± 0.7 | 5.4 ± 2.4 | 5.0 ± 1.9 | 4.6 ± 1.0 | 4.4 ± 0.9 |
| Glycerol (mmol/l) | 0.2 ± 0.0 | 0.2 ± 0.1 | 0.2 ± 0.0 | 0.2 ± 0.1 | 0.2 ± 0.1 | 0.1 ± 0.1 | 0.1 ± 0.1 | 0.1 ± 0.1 |

Values represent mean ± SD for at least 11 mice per group.
*p < 0.05 vs. control.
**p < 0.01 vs. control.

EXAMPLE 12

Hyperinsulinemic Euglycemic Clamp in DIO mice After acute Treatment with GLP-1 MMB. 4 groups (n=12 each) of C57Bl mice with diet-induced obesity were treated by intraperitoneally with 1 mg/kg and 0.1 mg/kg CNT0736, 7.1 ug/ml exenatide and PBS. 2 hours post dosing mice were subjected to hyperinsulinemic euglycemic clamp.

The data obtained suggest that acute treatment with CNTO 736 and exenatide tend to decrease the basal glucose production and increase the whole body glucose disposal, but the differences do not reach statistical significance between any of the treatment groups, likely due to the variable insulin levels achieved during basal and clamp condition. Percent of insulin-stimulated hepatic glucose production did not change in response to treatments.

Sprague-Dawley rats weighing 250-350 g were cannulized into the lateral ventricle at the following coordinates: −0.80 mm anterior, +1.2 mm lateral to bregma, −3.2 mm ventral to bregma. Animals were submitted for Angiotensin II testing to confirm that the cannulas were placed appropriately. Rats were acclimated to a reversed light/dark cycle and to handling. A 24-hour fasted/refed measurement was taken after a single PBS injection in order to establish a feeding baseline. Animals were evenly distributed according to 24-hour food intake from PBS injections (3 groups of 10 animals). Seventen days following PBS injection, rats were fasted for 24 hours and were dosed icv prior to entering the dark cycle. The rats were dosed with either CNTO 736 (3 nmols), exendin-4 (3 nmols), or PBS in a volume of 5 □L. Food intake and water intake were measured from 0-12 and 12-24 hours after dosing and body weight was measured after 24 and 48 hours. In the first 12 hours following dosing, there was a significant reduction in food and water intake with exendin-4 and CNTO 736 treatments. In the second 12 hours following dosing (12-24 hours), there was a significant reduction in food intake with both exendin-4 and CNTO 736 treatments, but a reduction in water intake was observed only with exendin-4 treatment. There was a significant reduction in body weight with exendin-4 treatment at both 24 and 48 hours, but not with CNTO 736.

EXAMPLE 14

Hyperinsulinemic Euglycemic Clamp in DIO Mice After Chronic Treatment with GLP-1 MMB. 4 groups (n=12 each) of C57Bl mice with diet-induced obesity were treated intraperitoneally with CNT0736 (1 or 0.1 mg/kg), exendin-4 (7.1 □g/kg) or PBS daily for 4 weeks. Two hours after the last dose, mice were subjected to hyperinsulinemic euglycemic clamp.

Chronic treatment with both doses of CNTO 736, but not exenatide significantly decreased basal hepatic glucose production. The high dose of CNTO 736 and exendin-4 significantly increased whole body glucose disposal in the hyperinsulinemic state. Both doses of CNTO 736 and exendin-4 increased insulin-inhibition of hepatic glucose production. Taken together, CNTO 736 and exendin-4 both improve insulin action including inhibition of hepatic glucose production and potentiation of glucose disposal. In contrast to exendin-4, CNTO 736 significantly decreased gluconeogenesis in the fasting state.

EXAMPLE 15

The Effect of GLP-1 MMB on Lipolysis. Acute or chronic administration of either dose of CNTO 736 or exendin-4 did not affect glycerol turnover in basal (fasting) or hyperinsulinemic conditions. Also, none of the drugs affected plasma free fatty acid (FFA) concentrations (Table 1 and 2).

EXAMPLE 16

The Effect of GLP-1 MMB on Lipolysis. Acute or chronic administration of either dose of CNTO 736 or exendin-4 did not affect glycerol turnover in basal (fasting) or hyperinsulinemic conditions. Also, none of the drugs affected plasma free fatty acid (FFA) concentrations (Table 1 and 2).

EXAMPLE 17

VLDL Production in Response to Acute and Chronic Treatment with GLP-MMB, Exenatide and Vehicle. Acute treatment with CNTO 736 and exenatide did not change the basal or hyperinsulinemic rate of VLDL production. In contrast, chronic treatment with either dose of CNTO 736, but not exenatide significantly decreased the basal and hyperinsulinemic rate of VLDL production.

Summary: The disclosed data suggest that chronic dosing with a GLP-1 MMB improves peripheral insulin sensitivity in mice with diet-induced obesity. In contrast to exendin-4, CNT0736 inhibited de novo glucose production. Moreover, chronic administration of GLP-1 MMB decreased VLDL production.

Advantages: The use of GLP-1 MMB as a therapeutic to treat type 2 diabetes provides the following advantages over other GLP-1 analogues. For example, it is likely to prolong the half-life of the GLP-1 peptide. Also, the wild-type GLP-1 peptide in the mimetibody constructs scaffold is resistant to protease degradation, specifically DPP-IV. This may allow for treatment with the wild-type GLP-1 peptide rather than a mutant peptide. Since GLP-1 is a native peptide, there may be less immune response in patients treated with a GLP-1 mimetibody constructs than in patients treated with a mutated GLP-1 analogue. In addition, the large size of the GLP-1 MMB may preclude it from crossing the blood brain barrier. This may offer an advantage since nausea and anxiety have been associated with GLP-1 engaging the GLP-1R in the brain. Furthermore, the mimetibody constructs platform results in expression of two peptides on each mimetibody constructs molecule. This may allow the GLP-1 peptides to interact with each other, forming a dimeric ligand that could increase affinity to the cell surface GLP-1 receptor.

It will be clear that the invention can be practiced otherwise than as particularly described in the foregoing description and examples.

In addition to its insulinotropic effect, CNTO 736 significantly improves peripheral insulin sensitivity including insulin-stimulated hepatic glucose production and insulin-stimulated glucose disposal.

CNTO 736 (but not exendin-4) inhibits hepatic gluconeogenesis. This is expected to allow for better control of fasting blood glucose and therefore better treatment outcomes in type 2 diabetic patients.

CNTO 736 (but not exendin-4) decreases VLDL production. This may provide additional benefits for the treatment of dislipidemia, obesity, and cardiovascular disorders frequently associated with diabetes. In addition, a GLP-1 MMB has the potential to treat these diseases in the absence of diabetes.

It will be clear that the invention can be practiced otherwise than as particularly described in the foregoing description and examples.

Numerous modifications and variations of the present invention are possible in light of the above teachings and, therefore, are within the scope of the present invention.

TABLE 3

| SEQ ID NO | | | TOTAL AA NO | REGIONS FR1 | FR4 |
|---|---|---|---|---|---|
| 47 | Heavy | Vh1 | 125 | 1-31 | 81-125 |
| 48 | chain | Vh2 | 97 | 1-30 | 80-97 |
| 49 | variable | Vh3a | 102 | 1-30 | 80-102 |
| 50 | region | Vh3b | 102 | 1-30 | 80-102 |
| 51 | | Vh3c | 94 | 1-30 | 80-94 |
| 52 | | Vh4 | 106 | 1-30 | 80-106 |
| 53 | | Vh5 | 97 | 1-30 | 80-97 |
| 54 | | Vh6 | 91 | 1-30 | 80-91 |
| 55 | | Vh7 | 91 | 1-30 | 80-91 |

| SEQ ID NO | | | AA NO | REGIONS hinge1 | hinge2 | hinge3 | hinge4 | CH2 | CH3 | CH4 |
|---|---|---|---|---|---|---|---|---|---|---|
| 56 | Heavy | IgA1 | 354 | 103-122 | | | | 123-222 | 223-354 | |
| 57 | chain | IgA2 | 340 | 103-108 | | | | 109-209 | 210-340 | |
| 58 | constant | IgD | 384 | 102-135 | 319-497 | | | 160-267 | 268-384 | |
| 59 | region | IgE | 497 | | | | | 104-210 | 211-318 | 319-497 |
| 60 | | IgG1 | 339 | 99-121 | | | | 122-223 | 224-339 | |
| 61 | | IgG2 | 326 | 99-117 | | | | 118-219 | 220-326 | |
| 62 | | IgG3 | 377 | 99-115 | | 131-145 | 146-168 | 169-270 | 271-377 | |
| 63 | | IgG4 | 327 | 99-110 | 324-476 | | | 111-220 | 221-327 | |
| 64 | | IgM | 476 | | | | | 105-217 | 218-323 | 324-476 |

TABLE 4

MMB CNTO 736 GLP-1 amino acid sequence

```
SIGNAL SEQUENCE..........................................
Met Ala Trp Val Trp Thr Leu Leu Phe Leu Met Ala Ala Ala Gln  (SEQ ID NO: 69)
ATG GCT TGG GTG TGG ACC TTG CTA TTC CTG ATG GCG GCC GCC CAA  (SEQ ID NO: 70)

.............. . GLP-1....................................
Ser Ile Gln Ala His Ala Glu Gly Thr Phe Thr Ser Asp Val Ser
AGT ATA CAG GCC CAT GCT GAA GGG ACC TTT ACT AGT GAT GTA AGT

..........................................................
Ser Tyr Leu Glu Gly Gln Ala Ala Lys Glu Phe Ile Ala Trp Leu
TCT TAT TTG GAA GGC CAA GCT GCC AAG GAA TTC ATT GCT TGG CTG

................ LINKER......................... VH....... .
Val Lys Gly Arg Gly Gly Gly Ser Gly Gly Gly Ser Gly Thr Leu
GTG AAA GGC CGA GGA GGT GGA TCC GGT GGA GGC TCC GGT ACC TTA

.................... HINGE...............................
Val Thr Val Ser Ser Glu Pro Lys Ser Cys Asp Lys Thr His Thr
GTC ACC GTC TCC TCA GAG CCC AAA TCT TGT GAC AAA ACT CAC ACG

.................... CH2..................................
Cys Pro Pro Cys Pro Ala Pro Glu Leu Leu Gly Gly Pro Ser Val
TGC CCA CCG TGC CCA GCA CCT GAA CTC CTG GGG GGA CCG TCA GTC

..........................................................
Phe Leu Phe Pro Pro Lys Pro Lys Asp Thr Leu Met Ile Ser Arg
TTC CTC TTC CCC CCA AAA CCC AAG GAC ACC CTC ATG ATC TCC CGG

..........................................................
Thr Pro glu Val Thr Cys Val Val Val Asp Val Ser His Glu Asp
ACC CCT GAG GTC ACA TGC GTG GTG GTG GAC GTG AGC CAC GAA GAC ..........................................................
Pro Glu Val Lys Phe Asn Trp Tyr Val Asp Gly Val Glu Val His
CCT GAG GTC AAG TTC AAC TGG TAC GTG GAC GGC GTG GAG GTG CAT ..........................................................
Asn Ala Lys Thr Lys Pro Arg GLu Glu Gln Tyr Asn Ser Thr tyr
AAT GCC AAG ACA AAG CCG CGG GAG GAG CAG TAC AAC AGC ACG TAC

.......................................................... .
```

TABLE 4-continued

MMB CNTO 736 GLP-1 amino acid sequence

```
Arg Val Val Ser Val Leu Thr Val Leu His Gln Asp Trp Leu Asn
CGG GTG GTC AGC GTC CTC ACC GTC CTG CAC CAG GAC TGG CTG AAT

................................................. .
Gly Lys Glu Tyr Lys Cys Lys Val Ser Asn Lys Ala Leu Pro Ala
GGC AAG GAG TAC AAG TGC AAG GTC TCC AAC AAA GCC CTC CCA GCC

........................... CH3.............. .
Pro Ile Glu Lys Thr Ile Ser Lys Ala Lys Gly Gln Pro Arg Glu
CCC ATC GAG AAA ACC ATC TCC AAA GCC AAA GGG CAG CCC CGA GAA

................................................. .
Pro Gln Val Tyr Thr Leu Pro Pro Ser Arg Asp Glu Leu Thr Lys
CCA CAG GTG TAC ACC CTG CCC CCA TCC CGG GAT GAG CTG ACC AAG

................................................. .
Asn Gln Val Ser Leu Thr Cys Leu Val Lys Gly Phe Tyr Pro Ser
AAC CAG GTC AGC CTG ACC TGC CTG GTC AAA GGC TTC TAT CCC AGC

................................................. .
Asp Ile Ala Val Glu Trp Glu Ser Asn Gly Gln Pro Glu Asn Asn
GAC ATC GCC GTG GAG TGG GAG AGC AAT GGG CAG CCG GAG AAC AAC

................................................. .
Tyr Lys Thr Thr Pro Pro Val Leu Asp Ser Asp Gly Ser Phe Phe
TAC AAG ACC ACG CCT CCC GTG CTG GAC TCC GAC GGC TCC TTC TTC

................................................. .
Leu Tyr Ser Lys Leu Thr Val Asp Lys Ser Arg Trp Gln Gln Gly
CTC TAC AGC AAG CTC ACC GTG GAC AAG AGC AGG TGG CAG CAG GGG

................................................. .
Asn Val Phe Ser Cys Ser Val Met His Glu Ala Leu His Asn His
AAC GTC TTC TCA TGC TCC GTG ATG CAT GAG GCT CTG CAC AAC CAC

.......................................... . STOP
Tyr Thr Gln Lys Ser Leu Ser Leu Ser Pro Gly Lys
TAC ACG CAG AAG AGC CTC TCC CTG TCT CCG GGT AAA TGA
```

---

What is claimed is:

1. A method for treating insulin sensitivity in an animal or human patient in need thereof, comprising administering a composition comprising an effective amount of at least one glucagon-like peptide 1 (GLP-1) receptor mimetibody agonist to at least one cell, tissue, organ or animal to improve insulin sensitivity of said animal or patient, wherein said mimetibody agonist comprises the GLP-1 receptor binding region of SEQ ID NO: 4.

2. A method according to claim 1, wherein said effective amount is 0.001-50 mg of the GLP-1 receptor mimetibody agonist of claim; 0.000001-500 mg of the GLP-1 receptor mimetibody agonist of claim 1; or 0.0001-100 mg of the GLP-1 receptor mimetibody agonist of claim 1 per kilogram, or equivalent concentration in said cells, tissue, organ or animal.

3. A method according to claim 1, wherein said administrating is by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

4. A method according to claim 1, wherein said effective amount treats said insulin sensitivity by lowering blood glucose levels in an animal in need thereof.

5. A method according to claim 1, wherein said effective amount treats said insulin sensitivity by increasing insulin secretion from insulin producing cells.

6. A method according to claim 5, wherein said effective amount treats said insulin sensitivity by inhibiting apoptosis of insulin producing cells.

7. A method according to claim 5, wherein said effective amount treats said insulin sensitivity thereby increasing the proliferation of insulin producing cells.

8. A method according to claim 1, wherein said insulin sensitivity is related to diabetes.

* * * * *

SEQUENCE LISTING

<160> NUMBER OF SEQ ID NOS: 70

<210> SEQ ID NO 1
<211> LENGTH: 31
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ala, Gly, Ser, Thr, Leu, Ile, Val, Glu,
      Asp or Lys.
<220> FEATURE:
<221> NAME/KEY: MISC_FEATURE
<222> LOCATION: (3)..(3)
<223> OTHER INFORMATION: Xaa is Glu, Asp or Lys.
<220> FEATURE:
<221> NAME/KEY: MISC_FEATURE
<222> LOCATION: (6)..(6)
<223> OTHER INFORMATION: Xaa is Phe, His, Trp or Tyr.
<220> FEATURE:
<221> NAME/KEY: MISC_FEATURE
<222> LOCATION: (7)..(7)
<223> OTHER INFORMATION: Xaa is Thr or Asn.
<220> FEATURE:
<221> NAME/KEY: MISC_FEATURE
<222> LOCATION: (8)..(8)
<223> OTHER INFORMATION: Xaa is Ala, Gly, Ser, Thr, Leu, Ile, Val, Glu,
      Asp or Lys.
<220> FEATURE:
<221> NAME/KEY: MISC_FEATURE

```
<222> LOCATION: (9)..(9)
<223> OTHER INFORMATION: Xaa is Glu or Asp.
<220> FEATURE:
<221> NAME/KEY: MISC_FEATURE
<222> LOCATION: (10)..(10)
<223> OTHER INFORMATION: Xaa10 is Val, Ala, Gly, Ser, Thr, Leu, Ile,
      Met, Tyr, Trp, His, Phe, Glu, Asp, or Lys
<220> FEATURE:
<221> NAME/KEY: MISC_FEATURE
<222> LOCATION: (11)..(11)
<223> OTHER INFORMATION: Xaa is Ser, Val, Ala, Gly, Thr, Leu, Ile, Glu,
      or Asp.
<220> FEATURE:
<221> NAME/KEY: MISC_FEATURE
<222> LOCATION: (12)..(12)
<223> OTHER INFORMATION: Xaa is Ala, Gly, Ser, Thr, Leu, Ile, Val, Glu,
      Asp or Lys.
<220> FEATURE:
<221> NAME/KEY: MISC_FEATURE
<222> LOCATION: (13)..(13)
<223> OTHER INFORMATION: Xaa is Tyr, Gln, His, Glu, or Lys.
<220> FEATURE:
<221> NAME/KEY: MISC_FEATURE
<222> LOCATION: (14)..(14)
<223> OTHER INFORMATION: Xaa14 is Leu, Ala, Met, Gly, Ser, Thr, Leu,
      Ile, Val, Glu, Asp or Lys.
<220> FEATURE:
<221> NAME/KEY: MISC_FEATURE
<222> LOCATION: (15)..(15)
<223> OTHER INFORMATION: Xaa is Glu, Ala, Thr, Ser, Gly, Gln, Asp, or
      Lys.
<220> FEATURE:
<221> NAME/KEY: MISC_FEATURE
<222> LOCATION: (16)..(16)
<223> OTHER INFORMATION: Xaa is Ala, Gly, Ser, Thr, Leu, Ile, Val, Gln,
      Asn, Arg, Cys, Glu, Asp or Lys.
<220> FEATURE:
<221> NAME/KEY: MISC_FEATURE
<222> LOCATION: (17)..(17)
<223> OTHER INFORMATION: Xaa is Gln, Asn, Arg, His, Glu, Asp or Lys.
<220> FEATURE:
<221> NAME/KEY: MISC_FEATURE
<222> LOCATION: (18)..(18)
<223> OTHER INFORMATION: Xaa is Ala, Gly, Ser, Thr, Leu, Ile, Val, Glu,
      Asp or Lys.
<220> FEATURE:
<221> NAME/KEY: MISC_FEATURE
<222> LOCATION: (19)..(19)
<223> OTHER INFORMATION: Xaa is Ala, Gly, Ser, Thr, Leu, Ile, Val, Glu,
      Asp or Lys.
<220> FEATURE:
<221> NAME/KEY: MISC_FEATURE
<222> LOCATION: (20)..(20)
<223> OTHER INFORMATION: Xaa20 is Lys, Arg, His, Gln, Trp, Tyr, Phe, Glu
      or Asp.
<220> FEATURE:
<221> NAME/KEY: MISC_FEATURE
<222> LOCATION: (21)..(21)
<223> OTHER INFORMATION: Xaa21 is Glu, Leu, Ala, His, Phe, Tyr, Trp,
      Arg, Gln, Thr, Ser, Gly, Asp or Lys.
<220> FEATURE:
<221> NAME/KEY: MISC_FEATURE
<222> LOCATION: (23)..(23)
<223> OTHER INFORMATION: Xaa is Ala, Val, Leu, or Glu.
<220> FEATURE:
<221> NAME/KEY: MISC_FEATURE
<222> LOCATION: (24)..(24)
<223> OTHER INFORMATION: Xaa24 is Ala, Gly, Ser, Thr, Leu, Ile, Val,
      His, Glu, Asp or Lys.
<220> FEATURE:
<221> NAME/KEY: MISC_FEATURE
<222> LOCATION: (25)..(25)
<223> OTHER INFORMATION: Xaa25 is Trp, Phe, Tyr, Glu, Asp or Lys.
<220> FEATURE:
<221> NAME/KEY: MISC_FEATURE
<222> LOCATION: (26)..(26)
<223> OTHER INFORMATION: Xaa26 is Leu, Gly, Ala, Ser, Thr, Ile, Val,
      Glu, Asp or Lys.
<220> FEATURE:
```

```
<221> NAME/KEY: MISC_FEATURE
<222> LOCATION: (27)..(27)
<223> OTHER INFORMATION: Xaa is Val, Gln, His, Glu, or Lys.
<220> FEATURE:
<221> NAME/KEY: MISC_FEATURE
<222> LOCATION: (28)..(28)
<223> OTHER INFORMATION: Xaa is Lys, Asn, Arg, His, Glu, or Asp.
<220> FEATURE:
<221> NAME/KEY: MISC_FEATURE
<222> LOCATION: (29)..(29)
<223> OTHER INFORMATION: Xaa29 is Gly, Ala, Ser, Thr, Leu, Ile, Val,
      Arg, Trp, Tyr, Phe, Pro, His, Glu, Asp or Lys.
<220> FEATURE:
<221> NAME/KEY: MISC_FEATURE
<222> LOCATION: (30)..(30)
<223> OTHER INFORMATION: Xaa is Arg, His, Thr, Ser, Trp, Tyr, Phe, Glu,
      Asp or Lys.
<220> FEATURE:
<221> NAME/KEY: MISC_FEATURE
<222> LOCATION: (31)..(31)
<223> OTHER INFORMATION: Xaa31 is Gly, Ala, Ser, Thr, Leu, Ile, Val,
      Arg, Trp, Tyr, Phe, His, Glu, Asp, Lys.

<400> SEQUENCE: 1

His Xaa Xaa Gly Thr Xaa Xaa Xaa Xaa Xaa Xaa Xaa Xaa Xaa Xaa
1               5                   10                  15

Xaa Xaa Xaa Xaa Xaa Phe Xaa Xaa Xaa Xaa Xaa Xaa Xaa Xaa
            20                  25                  30

<210> SEQ ID NO 2
<211> LENGTH: 278
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Gln, Glu, Lys, His or Ala.
<220> FEATURE:
<221> NAME/KEY: MISC_FEATURE
<222> LOCATION: (12)..(12)
<223> OTHER INFORMATION: Xaa is Gln, Glu, Lys, His or Ala.
<220> FEATURE:
<221> NAME/KEY: MISC_FEATURE
<222> LOCATION: (13)..(13)
<223> OTHER INFORMATION: Xaa is Gln, Glu, Lys, His or Ala.
<220> FEATURE:
<221> NAME/KEY: MISC_FEATURE
<222> LOCATION: (19)..(19)
<223> OTHER INFORMATION: Xaa is Gln, Glu, Lys, His or Ala.
<220> FEATURE:
<221> NAME/KEY: MISC_FEATURE
<222> LOCATION: (24)..(24)
<223> OTHER INFORMATION: Xaa is Gln, Glu, Lys, or Ala.
<220> FEATURE:
<221> NAME/KEY: MISC_FEATURE
<222> LOCATION: (27)..(27)
<223> OTHER INFORMATION: Xaa is Gln, Glu, Lys, His or Ala.
<220> FEATURE:
<221> NAME/KEY: MISC_FEATURE
<222> LOCATION: (44)..(44)
<223> OTHER INFORMATION: Xaa is Asn or Gln.

<400> SEQUENCE: 2

His Ala Glu Gly Thr Phe Thr Ser Asp Xaa Ser Xaa Xaa Leu Glu Gly
1               5                   10                  15

Gln Ala Xaa Lys Glu Phe Ile Xaa Trp Leu Xaa Lys Gly Arg Gly Gly
            20                  25                  30

Gly Ser Gly Gly Gly Ser Gly Thr Leu Val Thr Xaa Ser Ser Glu Pro
        35                  40                  45

Lys Ser Cys Asp Lys Thr His Thr Cys Pro Pro Cys Pro Ala Pro Glu
    50                  55                  60
```

```
Leu Leu Gly Gly Pro Ser Val Phe Leu Phe Pro Pro Lys Pro Lys Asp
 65                  70                  75                  80

Thr Leu Met Ile Ser Arg Thr Pro Glu Val Thr Cys Val Val Val Asp
                 85                  90                  95

Val Ser His Glu Asp Pro Glu Val Lys Phe Asn Trp Tyr Val Asp Gly
            100                 105                 110

Val Glu Val His Asn Ala Lys Thr Lys Pro Arg Glu Glu Gln Tyr Asn
        115                 120                 125

Ser Thr Tyr Arg Val Val Ser Val Leu Thr Val Leu His Gln Asp Trp
130                 135                 140

Leu Asn Gly Lys Glu Tyr Lys Cys Lys Val Ser Asn Lys Ala Leu Pro
145                 150                 155                 160

Ala Pro Ile Glu Lys Thr Ile Ser Lys Ala Lys Gly Gln Pro Arg Glu
                165                 170                 175

Pro Gln Val Tyr Thr Leu Pro Pro Ser Arg Asp Glu Leu Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Lys
225                 230                 235                 240

Leu Thr Val Asp Lys Ser Arg Trp Gln Gln Gly Asn Val Phe Ser Cys
                245                 250                 255

Ser Val Met His Glu Ala Leu His Asn His Tyr Thr Gln Lys Ser Leu
            260                 265                 270

Ser Leu Ser Pro Gly Lys
        275

<210> SEQ ID NO 3
<211> LENGTH: 837
<212> TYPE: DNA
<213> ORGANISM: Homo sapiens
<220> FEATURE:
<221> NAME/KEY: MISC_FEATURE
<222> LOCATION: (28)..(28)
<223> OTHER INFORMATION: n is nucleotide G, C, A, or U/T as part of the
      codon of 28-30 encoding Gln, Glu, Lys, His or Ala.
<220> FEATURE:
<221> NAME/KEY: MISC_FEATURE
<222> LOCATION: (29)..(29)
<223> OTHER INFORMATION: n is any nucleotide G, C, A, or U/T as part of
      the codon of 28-30 encoding Gln, Glu, Lys, His or Ala.
<220> FEATURE:
<221> NAME/KEY: MISC_FEATURE
<222> LOCATION: (30)..(30)
<223> OTHER INFORMATION: n is any nucleotide G, C, A, or U/T as part of
      the codon of 28-30 encoding Gln, Glu, Lys, His or Ala.
<220> FEATURE:
<221> NAME/KEY: MISC_FEATURE
<222> LOCATION: (37)..(37)
<223> OTHER INFORMATION: n is any nucleotide G, C, A, or U/T as part of
      the codon of 37-39 encoding Gln, Glu, Lys, His or Ala.
<220> FEATURE:
<221> NAME/KEY: MISC_FEATURE
<222> LOCATION: (38)..(38)
<223> OTHER INFORMATION: n is any nucleotide G, C, A, or U/T as part of
      the codon of 37-39 encoding Gln, Glu, Lys, His or Ala.
<220> FEATURE:
<221> NAME/KEY: MISC_FEATURE
<222> LOCATION: (39)..(39)
<223> OTHER INFORMATION: n is any nucleotide G, C, A, or U/T as part of
      the codon of 37-39 encoding Gln, Glu, Lys, His or Ala.
<220> FEATURE:
<221> NAME/KEY: MISC_FEATURE
```

```
<222> LOCATION: (40)..(40)
<223> OTHER INFORMATION: n is any nucleotide G, C, A, or U/T as part of
      the codon of 40-42 encoding Gln, Glu, Lys, His or Ala.
<220> FEATURE:
<221> NAME/KEY: MISC_FEATURE
<222> LOCATION: (41)..(41)
<223> OTHER INFORMATION: n is any nucleotide G, C, A, or U/T as part of
      the codon of 40-42 encoding Gln, Glu, Lys, His or Ala.
<220> FEATURE:
<221> NAME/KEY: MISC_FEATURE
<222> LOCATION: (42)..(42)
<223> OTHER INFORMATION: n is any nucleotide G, C, A, or U/T as part of
      the codon of 40-42 encoding Gln, Glu, Lys, His or Ala.
<220> FEATURE:
<221> NAME/KEY: MISC_FEATURE
<222> LOCATION: (70)..(70)
<223> OTHER INFORMATION: n is any nucleotide G, C, A, or U/T as part of
      the codon of 70-72 encoding Gln, Glu, Lys, His or Ala.
<220> FEATURE:
<221> NAME/KEY: MISC_FEATURE
<222> LOCATION: (71)..(71)
<223> OTHER INFORMATION: n is any nucleotide G, C, A, or U/T as part of
      the codon of 70-72 encoding Gln, Glu, Lys, His or Ala.
<220> FEATURE:
<221> NAME/KEY: MISC_FEATURE
<222> LOCATION: (72)..(72)
<223> OTHER INFORMATION: n is any nucleotide G, C, A, or U/T as part of
      the codon of 70-72 encoding Gln, Glu, Lys, His or Ala.
<220> FEATURE:
<221> NAME/KEY: MISC_FEATURE
<222> LOCATION: (79)..(79)
<223> OTHER INFORMATION: n is any nucleotide G, C, A, or U/T as part of
      the codon of 79-81 encoding Gln, Glu, Lys, His or Ala.
<220> FEATURE:
<221> NAME/KEY: MISC_FEATURE
<222> LOCATION: (80)..(80)
<223> OTHER INFORMATION: n is any nucleotide G, C, A, or U/T as part of
      the codon of 79-81 encoding Gln, Glu, Lys, His or Ala.
<220> FEATURE:
<221> NAME/KEY: MISC_FEATURE
<222> LOCATION: (81)..(81)
<223> OTHER INFORMATION: n is any nucleotide G, C, A, or U/T as part of
      the codon of 79-81 encoding Gln, Glu, Lys, His or Ala.
<220> FEATURE:
<221> NAME/KEY: MISC_FEATURE
<222> LOCATION: (130)..(130)
<223> OTHER INFORMATION: n is any nucleotide G, C, A, or U/T as part of
      the codon of 130-132 encoding Asn or Gln.
<220> FEATURE:
<221> NAME/KEY: MISC_FEATURE
<222> LOCATION: (131)..(131)
<223> OTHER INFORMATION: n is any nucleotide G, C, A, or U/T as part of
      the codon of 130-132 encoding Asn or Gln.
<220> FEATURE:
<221> NAME/KEY: MISC_FEATURE
<222> LOCATION: (132)..(132)
<223> OTHER INFORMATION: n is any nucleotide G, C, A, or U/T as part of
      the codon of 130-132 encoding Asn or Gln.

<400> SEQUENCE: 3
catgctgaag ggacctttac tagtgatnnn agttctnnnn nngaaggcca agctgccaag       60
gaattcattn nntggctgnn naaaggccga ggaggtggat ccggtggagg ctccggtacc     120
ttagtcaccn nntcctcaga gcccaaatct tgtgacaaaa ctcacacgtg cccaccgtgc     180
ccagcacctg aactcctggg gggaccgtca gtcttcctct tccccccaaa acccaaggac     240
accctcatga tctcccggac ccctgaggtc acatgcgtgg tggtggacgt gagccacgaa     300
gaccctgagg tcaagttcaa ctggtacgtg gacggcgtgg aggtgcataa tgccaagaca     360
aagccgcggg aggagcagta caacagcacg taccgggtgg tcagcgtcct caccgtcctg     420
caccaggact ggctgaatgg caaggagtac aagtgcaagg tctccaacaa agccctccca     480
gcccccatcg agaaaaccat ctccaaagcc aagggcagc cccgagaacc acaggtgtac     540
```

```
accctgcccc catcccggga tgagctgacc aagaaccagg tcagcctgac ctgcctggtc    600
aaaggcttct atcccagcga catcgccgtg gagtgggaga gcaatgggca gccggagaac    660
aactacaaga ccacgcctcc cgtgctggac tccgacggct ccttcttcct ctacagcaag    720
ctcaccgtgg acaagagcag gtggcagcag gggaacgtct tctcatgctc cgtgatgcat    780
gaggctctgc acaaccacta cacgcagaag agcctctccc tgtctccggg taaatga      837
```

<210> SEQ ID NO 4
<211> LENGTH: 275
<212> TYPE: PRT
<213> ORGANISM: Homo sapiens

<400> SEQUENCE: 4

```
His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
                20                  25                  30

Gly Ser Gly Gly Gly Ser Gly Thr Leu Val Thr Asn Ser Ser Glu Ser
            35                  40                  45

Lys Tyr Gly Pro Pro Cys Pro Pro Cys Pro Ala Pro Glu Ala Ala Gly
        50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
        130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
        210                 215                 220

Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Lys
        275
```

<210> SEQ ID NO 5
<211> LENGTH: 828
<212> TYPE: DNA
<213> ORGANISM: Homo sapiens

<400> SEQUENCE: 5

```
catgctgaag ggacctttac tagtgatgta agttcttatt tggaaggcca agctgccaag      60
gaattcattg aatggctggt gaaaggccga ggaggtggat ccggtggagg ctccggtacc     120
ttagtcacca actcctcaga gtccaaatat ggtcccccat gcccaccatg cccggcgcct     180
gaggccgccg ggggaccatc agtcttcctg ttccccccaa aacccaagga cactctcatg     240
atctcccgga cccctgaggt cacgtgcgtg gtggtggacg tgagccagga agaccccgag     300
gtccagttca actggtacgt ggatggcgtg gaggtgcata atgccaagac aaagccgcgg     360
gaggagcagt tcaacagcac gtaccgtgtg gtcagcgtcc tcaccgtcct gcaccaggac     420
tggctgaacg gcaaggagta caagtgcaag gtctccaaca aaggcctccc gtcctccatc     480
gagaaaacca tctccaaagc caaagggcag cctcgagagc cacaggtgta caccctgccc     540
ccatcccagg aggagatgac caagaaccag gtcagcctga cctgcctggt caaaggcttc     600
taccccagcg acatcgccgt ggagtgggag agcaatgggc agccggagaa caactacaag     660
accacgcctc ccgtgctgga ctccgacggc tccttcttcc tctacagcag gctaaccgtg     720
gacaagagca ggtggcagga ggggaatgtc ttctcatgct ccgtgatgca tgaggctctg     780
cacaaccact acacacagaa aagcttgtcc ctgtctctgg gtaaatga                 828
```

```
<210> SEQ ID NO 6
<211> LENGTH: 30
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ala, Gly, Ser.
<220> FEATURE:
<221> NAME/KEY: MISC_FEATURE
<222> LOCATION: (3)..(3)
<223> OTHER INFORMATION: Xaa is Glu, Asp.
<220> FEATURE:
<221> NAME/KEY: MISC_FEATURE
<222> LOCATION: (6)..(6)
<223> OTHER INFORMATION: Xaa is Phe or Tyr.
<220> FEATURE:
<221> NAME/KEY: MISC_FEATURE
<222> LOCATION: (7)..(7)
<223> OTHER INFORMATION: Xaa is Thr or Asn.
<220> FEATURE:
<221> NAME/KEY: MISC_FEATURE
<222> LOCATION: (8)..(8)
<223> OTHER INFORMATION: Xaa is Ala, Ser, Thr.
<220> FEATURE:
<221> NAME/KEY: MISC_FEATURE
<222> LOCATION: (9)..(9)
<223> OTHER INFORMATION: Xaa is Glu or Asp.
<220> FEATURE:
<221> NAME/KEY: MISC_FEATURE
<222> LOCATION: (10)..(10)
<223> OTHER INFORMATION: Xaa is Val, Gln, Met or Ile.
<220> FEATURE:
<221> NAME/KEY: MISC_FEATURE
<222> LOCATION: (12)..(12)
<223> OTHER INFORMATION: Xaa is Ser or Lys.
<220> FEATURE:
<221> NAME/KEY: MISC_FEATURE
<222> LOCATION: (14)..(14)
<223> OTHER INFORMATION: Xaa is Leu, Gln, His, Glu, or Met.
<220> FEATURE:
<221> NAME/KEY: MISC_FEATURE
<222> LOCATION: (16)..(16)
<223> OTHER INFORMATION: Xaa is Gly, Ala, Glu, or Asp.
<220> FEATURE:
<221> NAME/KEY: MISC_FEATURE
<222> LOCATION: (17)..(17)
<223> OTHER INFORMATION: Xaa is Gln, or Glu.
<220> FEATURE:
```

```
<221> NAME/KEY: MISC_FEATURE
<222> LOCATION: (18)..(18)
<223> OTHER INFORMATION: Xaa is Ala or Lys.
<220> FEATURE:
<221> NAME/KEY: MISC_FEATURE
<222> LOCATION: (19)..(19)
<223> OTHER INFORMATION: Xaa is Ala, Leu, Ile, Val, or Met.
<220> FEATURE:
<221> NAME/KEY: MISC_FEATURE
<222> LOCATION: (21)..(21)
<223> OTHER INFORMATION: Xaa is Glu or Leu.
<220> FEATURE:
<221> NAME/KEY: MISC_FEATURE
<222> LOCATION: (23)..(23)
<223> OTHER INFORMATION: Xaa is Ala, Val, Ile, Leu, or Glu.
<220> FEATURE:
<221> NAME/KEY: MISC_FEATURE
<222> LOCATION: (27)..(27)
<223> OTHER INFORMATION: Xaa is Val, Gln, His, Glu, or Lys.
<220> FEATURE:
<221> NAME/KEY: MISC_FEATURE
<222> LOCATION: (28)..(28)
<223> OTHER INFORMATION: Xaa is Lys or Asn.
<220> FEATURE:
<221> NAME/KEY: MISC_FEATURE
<222> LOCATION: (30)..(30)
<223> OTHER INFORMATION: Xaa is Arg or Glu.

<400> SEQUENCE: 6

His Xaa Xaa Gly Thr Xaa Xaa Xaa Xaa Xaa Ser Xaa Tyr Xaa Glu Xaa
 1               5                  10                  15

Xaa Xaa Xaa Lys Xaa Phe Xaa Ala Trp Leu Xaa Xaa Gly Xaa
            20                  25                  30

<210> SEQ ID NO 7
<211> LENGTH: 63
<212> TYPE: PRT
<213> ORGANISM: Homo sapiens

<400> SEQUENCE: 7

His Ser Glu Gly Thr Phe Thr Ser Asp Val Ser Ser Tyr Leu Glu Gly
 1               5                  10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
    50                  55                  60

<210> SEQ ID NO 8
<211> LENGTH: 63
<212> TYPE: PRT
<213> ORGANISM: Homo sapiens

<400> SEQUENCE: 8

His Gly Glu Gly Thr Phe Thr Ser Asp Val Ser Ser Tyr Leu Glu Gly
 1               5                  10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
    50                  55                  60

<210> SEQ ID NO 9
<211> LENGTH: 63
```

```
<212> TYPE: PRT
<213> ORGANISM: Homo sapiens

<400> SEQUENCE: 9

His Asp Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
50                  55                  60

<210> SEQ ID NO 10
<211> LENGTH: 63
<212> TYPE: PRT
<213> ORGANISM: Homo sapiens

<400> SEQUENCE: 10

His Thr Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
50                  55                  60

<210> SEQ ID NO 11
<211> LENGTH: 63
<212> TYPE: PRT
<213> ORGANISM: Homo sapiens

<400> SEQUENCE: 11

His Val Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
50                  55                  60

<210> SEQ ID NO 12
<211> LENGTH: 52
<212> TYPE: PRT
<213> ORGANISM: Homo sapiens

<400> SEQUENCE: 12

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Thr Gly
            20                  25                  30

Gly Gly Ser Glu Ser Lys Tyr Gly Pro Pro Cys Pro Pro Cys Pro Ala
        35                  40                  45

Pro Glu Ala Ala
    50

<210> SEQ ID NO 13
```

```
<211> LENGTH: 43
<212> TYPE: PRT
<213> ORGANISM: Homo sapiens

<400> SEQUENCE: 13

His Ser Glu Gly Thr Phe Thr Ser Asp Val Ser Ser Tyr Leu Glu Gly
1               5                   10                  15
Gln Ala Ala Lys Glu Phe Ile Glu Trp Leu Val Lys Gly Arg Thr Gly
            20                  25                  30
Ser Cys Pro Pro Cys Pro Ala Pro Glu Ala Asn
            35                  40

<210> SEQ ID NO 14
<211> LENGTH: 72
<212> TYPE: PRT
<213> ORGANISM: Homo sapiens

<400> SEQUENCE: 14

His Gly Glu Gly Thr Phe Thr Ser Asp Val Ser Ser Tyr Leu Glu Gly
1               5                   10                  15
Gln Ala Ala Lys Glu Phe Ile Glu Trp Leu Val Lys Gly Gly Pro Ser
            20                  25                  30
Ser Gly Ala Pro Pro Pro Ser Gly Gly Ser Gly Gly Ser Gly
            35                  40                  45
Thr Leu Val Thr Asn Ser Ser Glu Ser Lys Tyr Gly Pro Pro Cys Pro
        50                  55                  60
Pro Cys Pro Ala Pro Glu Ala Ala
65                  70

<210> SEQ ID NO 15
<211> LENGTH: 31
<212> TYPE: PRT
<213> ORGANISM: Homo sapiens

<400> SEQUENCE: 15

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Gly
            20                  25                  30

<210> SEQ ID NO 16
<211> LENGTH: 4
<212> TYPE: PRT
<213> ORGANISM: Homo sapiens

<400> SEQUENCE: 16

Gly Gly Gly Ser
1

<210> SEQ ID NO 17
<211> LENGTH: 6
<212> TYPE: PRT
<213> ORGANISM: Homo sapiens

<400> SEQUENCE: 17

Gly Ser Gly Gly Gly Ser
1               5

<210> SEQ ID NO 18
<211> LENGTH: 7
<212> TYPE: PRT
<213> ORGANISM: Homo sapiens
```

```
<400> SEQUENCE: 18

Gly Gly Ser Gly Gly Gly Ser
1               5

<210> SEQ ID NO 19
<211> LENGTH: 9
<212> TYPE: PRT
<213> ORGANISM: Homo sapiens

<400> SEQUENCE: 19

Gly Gly Ser Gly Gly Ser Gly Gly
1               5

<210> SEQ ID NO 20
<211> LENGTH: 10
<212> TYPE: PRT
<213> ORGANISM: Homo sapiens

<400> SEQUENCE: 20

Gly Gly Gly Ser Gly Gly Gly Ser Gly Gly
1               5                   10

<210> SEQ ID NO 21
<211> LENGTH: 8
<212> TYPE: PRT
<213> ORGANISM: Homo sapiens

<400> SEQUENCE: 21

Gly Thr Leu Val Thr Val Ser Ser
1               5

<210> SEQ ID NO 22
<211> LENGTH: 8
<212> TYPE: PRT
<213> ORGANISM: Homo sapiens

<400> SEQUENCE: 22

Gly Thr Leu Val Ala Val Ser Ser
1               5

<210> SEQ ID NO 23
<211> LENGTH: 8
<212> TYPE: PRT
<213> ORGANISM: Homo sapiens

<400> SEQUENCE: 23

Gly Thr Ala Val Thr Val Ser Ser
1               5

<210> SEQ ID NO 24
<211> LENGTH: 4
<212> TYPE: PRT
<213> ORGANISM: Homo sapiens

<400> SEQUENCE: 24

Thr Val Ser Ser
1

<210> SEQ ID NO 25
<211> LENGTH: 4
<212> TYPE: PRT
<213> ORGANISM: Homo sapiens

<400> SEQUENCE: 25
```

Ala Val Ser Ser
1

<210> SEQ ID NO 26
<211> LENGTH: 23
<212> TYPE: PRT
<213> ORGANISM: Homo sapiens

<400> SEQUENCE: 26

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 27
<211> LENGTH: 20
<212> TYPE: PRT
<213> ORGANISM: Homo sapiens

<400> SEQUENCE: 27

Glu Ser Lys Tyr Gly Pro Pro Cys Pro Ser Cys Pro Ala Pro Glu Phe
1               5                   10                  15

Leu Gly Gly Pro
            20

<210> SEQ ID NO 28
<211> LENGTH: 20
<212> TYPE: PRT
<213> ORGANISM: Homo sapiens

<400> SEQUENCE: 28

Glu Ser Lys Tyr Gly Pro Pro Cys Pro Pro Cys Pro Ala Pro Glu Ala
1               5                   10                  15

Ala Gly Gly Pro
            20

<210> SEQ ID NO 29
<211> LENGTH: 23
<212> TYPE: PRT
<213> ORGANISM: Homo sapiens

<400> SEQUENCE: 29

Glu Pro Lys Ser Ala Asp Lys Thr His Thr Cys Pro Pro Cys Pro Ala
1               5                   10                  15

Pro Glu Ala Ala Gly Gly Pro
            20

<210> SEQ ID NO 30
<211> LENGTH: 23
<212> TYPE: PRT
<213> ORGANISM: Homo sapiens

<400> SEQUENCE: 30

Glu Pro Lys Ser Ala Asp Lys Thr His Thr Cys Pro Pro Cys Pro Ala
1               5                   10                  15

Pro Glu Leu Ala Gly Gly Pro
            20

<210> SEQ ID NO 31
<211> LENGTH: 23
<212> TYPE: PRT
<213> ORGANISM: Homo sapiens

```
<400> SEQUENCE: 31

Glu Pro Lys Ser Ala Asp Lys Thr His Thr Cys Pro Pro Cys Pro Ala
1               5                   10                  15

Pro Glu Ala Leu Gly Gly Pro
            20

<210> SEQ ID NO 32
<211> LENGTH: 23
<212> TYPE: PRT
<213> ORGANISM: Homo sapiens

<400> SEQUENCE: 32

Glu Pro Lys Ser Ala Asp Lys Thr His Thr Cys Pro Pro Cys Pro Ala
1               5                   10                  15

Pro Glu Leu Glu Gly Gly Pro
            20

<210> SEQ ID NO 33
<211> LENGTH: 23
<212> TYPE: PRT
<213> ORGANISM: Homo sapiens

<400> SEQUENCE: 33

Glu Pro Lys Ser Ser Asp Lys Thr His Thr Cys Pro Pro Cys Pro Ala
1               5                   10                  15

Pro Glu Phe Leu Gly Gly Pro
            20

<210> SEQ ID NO 34
<211> LENGTH: 23
<212> TYPE: PRT
<213> ORGANISM: Homo sapiens

<400> SEQUENCE: 34

Glu Pro Lys Ser Ala Asp Lys Thr His Ala Cys Pro Pro Cys Pro Ala
1               5                   10                  15

Pro Glu Leu Leu Gly Gly Pro
            20

<210> SEQ ID NO 35
<211> LENGTH: 23
<212> TYPE: PRT
<213> ORGANISM: Homo sapiens

<400> SEQUENCE: 35

Glu Pro Lys Ser Ala Asp Lys Ala His Thr Cys Pro Pro Cys Pro Ala
1               5                   10                  15

Pro Glu Leu Leu Gly Gly Pro
            20

<210> SEQ ID NO 36
<211> LENGTH: 23
<212> TYPE: PRT
<213> ORGANISM: Homo sapiens

<400> SEQUENCE: 36

Glu Pro Lys Ser Ala Asp Lys Thr His Thr Cys Pro Pro Cys Pro Ala
1               5                   10                  15

Pro Glu Leu Leu Gly Gly Pro
            20
```

```
<210> SEQ ID NO 37
<211> LENGTH: 19
<212> TYPE: PRT
<213> ORGANISM: Homo sapiens

<400> SEQUENCE: 37

Ala Asp Lys Thr His Thr Cys Pro Pro Cys Pro Ala Pro Glu Leu Leu
1               5                   10                  15

Gly Gly Pro

<210> SEQ ID NO 38
<211> LENGTH: 16
<212> TYPE: PRT
<213> ORGANISM: Homo sapiens

<400> SEQUENCE: 38

Thr His Thr Cys Pro Pro Cys Pro Ala Pro Glu Leu Leu Gly Gly Pro
1               5                   10                  15

<210> SEQ ID NO 39
<211> LENGTH: 20
<212> TYPE: PRT
<213> ORGANISM: Homo sapiens

<400> SEQUENCE: 39

Glu Ser Lys Tyr Gly Pro Pro Cys Pro Ser Cys Pro Ala Pro Glu Ala
1               5                   10                  15

Ala Gly Gly Pro
            20

<210> SEQ ID NO 40
<211> LENGTH: 20
<212> TYPE: PRT
<213> ORGANISM: Homo sapiens

<400> SEQUENCE: 40

Glu Ser Lys Tyr Gly Pro Pro Cys Pro Pro Cys Pro Ala Pro Glu Leu
1               5                   10                  15

Leu Gly Gly Pro
            20

<210> SEQ ID NO 41
<211> LENGTH: 13
<212> TYPE: PRT
<213> ORGANISM: Homo sapiens

<400> SEQUENCE: 41

Cys Pro Pro Cys Pro Ala Pro Glu Leu Leu Gly Gly Pro
1               5                   10

<210> SEQ ID NO 42
<211> LENGTH: 13
<212> TYPE: PRT
<213> ORGANISM: Homo sapiens

<400> SEQUENCE: 42

Cys Pro Pro Cys Pro Ala Pro Glu Ala Ala Gly Gly Pro
1               5                   10

<210> SEQ ID NO 43
<211> LENGTH: 102
<212> TYPE: PRT
<213> ORGANISM: Homo sapiens
```

```
<400> SEQUENCE: 43

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser His Glu Asp
            20                  25                  30

Pro Glu Val Lys Phe Asn Trp Tyr Val Asp Gly Val Glu Val His Asn
        35                  40                  45

Ala Lys Thr Lys Pro Arg Glu Glu Gln Tyr Asn Ser Thr Tyr Arg Asn
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys
            100

<210> SEQ ID NO 44
<211> LENGTH: 106
<212> TYPE: PRT
<213> ORGANISM: Homo sapiens

<400> SEQUENCE: 44

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Asn Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 45
<211> LENGTH: 102
<212> TYPE: PRT
<213> ORGANISM: Homo sapiens

<400> SEQUENCE: 45

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Gln Glu Asp
            20                  25                  30

Pro Glu Val Gln Phe Asn Trp Tyr Val Asp Gly Val Glu Val His Asn
        35                  40                  45

Ala Lys Thr Lys Pro Arg Glu Glu Gln Phe Asn Ser Thr Tyr Arg Asn
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Gly Leu Pro Ser Ser Ile Glu Lys
                85                  90                  95
```

```
Thr Ile Ser Lys Ala Lys
            100

<210> SEQ ID NO 46
<211> LENGTH: 107
<212> TYPE: PRT
<213> ORGANISM: Homo sapiens

<400> SEQUENCE: 46

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Asn Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 47
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: Vh1 heavy chain variable region
<220> FEATURE:
<221> NAME/KEY: MISC_FEATURE
<222> LOCATION: (1)..(31)
<223> OTHER INFORMATION: framework 1
<220> FEATURE:
<221> NAME/KEY: MISC_FEATURE
<222> LOCATION: (32)..(32)
<223> OTHER INFORMATION: X is any amino acid.
<220> FEATURE:
<221> NAME/KEY: MISC_FEATURE
<222> LOCATION: (33)..(46)
<223> OTHER INFORMATION: framework 2
<220> FEATURE:
<221> NAME/KEY: MISC_FEATURE
<222> LOCATION: (47)..(47)
<223> OTHER INFORMATION: X is any amino acid.
<220> FEATURE:
<221> NAME/KEY: MISC_FEATURE
<222> LOCATION: (48)..(79)
<223> OTHER INFORMATION: framework 3
<220> FEATURE:
<221> NAME/KEY: MISC_FEATURE
<222> LOCATION: (80)..(80)
<223> OTHER INFORMATION: X is any amino acid.
<220> FEATURE:
<221> NAME/KEY: MISC_FEATURE
<222> LOCATION: (81)..(125)
<223> OTHER INFORMATION: framework 4

<400> SEQUENCE: 47

Gln Val Gln Leu Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Xaa
            20                  25                  30

Trp Val Arg Gln Ala Pro Gly Gln Gly Leu Glu Trp Met Gly Xaa Arg
```

-continued

```
                35                  40                  45
Val Thr Met Thr Arg Asp Thr Ser Thr Ser Thr Ala Tyr Met Glu Leu
         50                  55                  60

Ser Ser Leu Arg Ser Glu Asp Thr Ala Val Tyr Tyr Cys Ala Arg Xaa
 65                  70                  75                  80

Trp Gly Gln Gly Thr Leu Val Thr Asn Ser Ser Gly Ser Thr Lys Gly
                 85                  90                  95

Pro Ser Val Phe Pro Leu Ala Pro Ser Ser Lys Ser Thr Ser Gly Gly
                100                 105                 110

Thr Ala Ala Leu Gly Cys Leu Val Lys Asp Tyr Phe Pro
                115                 120                 125

<210> SEQ ID NO 48
<211> LENGTH: 124
<212> TYPE: PRT
<213> ORGANISM: Homo sapiens
<220> FEATURE:
<221> NAME/KEY: MISC_FEATURE
<222> LOCATION: (1)..(124)
<223> OTHER INFORMATION: Vh2 heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: Xaa is any amino acid.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: Xaa is any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: Xaa is any amino acids.
<220> FEATURE:
<221> NAME/KEY: MISC_FEATURE
<222> LOCATION: (80)..(124)
<223> OTHER INFORMATION: framework 4

<400> SEQUENCE: 48

Gln Ile Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Xaa Trp
                 20                  25                  30

Ile Arg Gln Pro Pro Gly Lys Ala Leu Glu Trp Leu Ala Xaa Arg Leu
             35                  40                  45

Thr Ile Thr Lys Asp Thr Ser Lys Asn Gln Val Val Leu Thr Met Thr
         50                  55                  60

Asn Met Asp Pro Val Asp Thr Ala Thr Tyr Tyr Cys Ala Arg Xaa Trp
 65                  70                  75                  80

Gly Gln Gly Thr Leu Val Thr Asn Ser Ser Ala Ser Pro Thr Ser Pro
                 85                  90                  95

Lys Val Phe Pro Leu Ser Leu Ser Ser Lys Ser Thr Ser Gly Gly Thr
                100                 105                 110

Ala Ala Leu Gly Cys Leu Val Lys Asp Tyr Phe Pro
```

```
                                115                     120

<210> SEQ ID NO 49
<211> LENGTH: 100
<212> TYPE: PRT
<213> ORGANISM: Homo sapiens
<220> FEATURE:
<221> NAME/KEY: MISC_FEATURE
<222> LOCATION: (1)..(100)
<223> OTHER INFORMATION: Vh3a heavy chain variable region
<220> FEATURE:
<221> NAME/KEY: MISC_FEATURE
<222> LOCATION: (1)..(31)
<223> OTHER INFORMATION: framework 1
<220> FEATURE:
<221> NAME/KEY: MISC_FEATURE
<222> LOCATION: (32)..(32)
<223> OTHER INFORMATION: complementarity determinng region 1 (CDR1), Xaa
      is any amino acids.
<220> FEATURE:
<221> NAME/KEY: MISC_FEATURE
<222> LOCATION: (33)..(46)
<223> OTHER INFORMATION: framework 2
<220> FEATURE:
<221> NAME/KEY: MISC_FEATURE
<222> LOCATION: (47)..(47)
<223> OTHER INFORMATION: complementarity determinng region 2 (CDR2), Xaa
      is any amino acids.
<220> FEATURE:
<221> NAME/KEY: MISC_FEATURE
<222> LOCATION: (48)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), Xaa
      is any amino acids.
<220> FEATURE:
<221> NAME/KEY: MISC_FEATURE
<222> LOCATION: (81)..(100)
<223> OTHER INFORMATION: framework 4

<400> SEQUENCE: 49

Glu Val Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Xaa
            20                  25                  30

Trp Val Arg Gln Ala Pro Gly Lys Gly Leu Glu Trp Val Ser Xaa Arg
        35                  40                  45

Phe Thr Ile Ser Arg Asp Asn Ser Lys Asn Thr Leu Tyr Leu Gln Met
    50                  55                  60

Asn Ser Leu Arg Ala Glu Asp Thr Ala Val Tyr Tyr Cys Ala Arg Xaa
65                  70                  75                  80

Trp Gly Gln Gly Thr Leu Val Thr Asn Ser Ser Gly Thr Lys Ala
                85                  90                  95

Pro Ser Val Phe
            100

<210> SEQ ID NO 50
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: Vh3b heavy chain variable region
<220> FEATURE:
<221> NAME/KEY: MISC_FEATURE
<222> LOCATION: (1)..(30)
<223> OTHER INFORMATION: framework 1
```

```
<220> FEATURE:
<221> NAME/KEY: MISC_FEATURE
<222> LOCATION: (31)..(31)
<223> OTHER INFORMATION: complementarity determinng region 1 (CDR1), Xaa
      is any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), Xaa
      is any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), Xaa
      is any amino acids.
<220> FEATURE:
<221> NAME/KEY: MISC_FEATURE
<222> LOCATION: (80)..(102)
<223> OTHER INFORMATION: framework 4

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Xaa Trp
            20                  25                  30

Val Arg Gln Ala Pro Gly Lys Gly Leu Glu Trp Val Gly Xaa Arg Phe
        35                  40                  45

Thr Ile Ser Arg Asp Asp Ser Lys Asn Thr Leu Tyr Leu Gln Met Asn
    50                  55                  60

Ser Leu Lys Thr Glu Asp Thr Ala Val Tyr Tyr Cys Thr Thr Xaa Trp
65                  70                  75                  80

Gly Gln Gly Thr Leu Val Thr Asn Ser Ser Ala Ser Thr Lys Gly Pro
                85                  90                  95

Ser Val Phe Pro Leu Ala
            100

<210> SEQ ID NO 51
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: Vh3c heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), Xaa
      is any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), Xaa
      is any amino acids.
<220> FEATURE:
```

```
<221> NAME/KEY: MISC_FEATURE
<222> LOCATION: (47)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), Xaa
      is any amino acids.
<220> FEATURE:
<221> NAME/KEY: MISC_FEATURE
<222> LOCATION: (81)..(101)
<223> OTHER INFORMATION: framework 4

<400> SEQUENCE: 51

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Xaa Trp
            20                  25                  30

Val Arg Gln Ala Pro Gly Lys Gly Leu Glu Trp Val Gly Xaa Arg Phe
        35                  40                  45

Thr Ile Ser Arg Asp Asp Ser Lys Ser Ile Ala Tyr Leu Gln Met Asn
    50                  55                  60

Ser Leu Lys Thr Glu Asp Thr Ala Val Tyr Tyr Cys Thr Arg Asn Xaa
65                  70                  75                  80

Trp Gly Gln Gly Thr Leu Val Thr Asn Ser Ser Gly Ser Thr Lys Gly
                85                  90                  95

Pro Ser Val Leu Pro
            100

<210> SEQ ID NO 52
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: Vh4 heavy chain variable region
<220> FEATURE:
<221> NAME/KEY: MISC_FEATURE
<222> LOCATION: (1)..(33)
<223> OTHER INFORMATION: framework 1
<220> FEATURE:
<221> NAME/KEY: MISC_FEATURE
<222> LOCATION: (34)..(34)
<223> OTHER INFORMATION: complementarity determinng region 1 (CDR1), Xaa
      is any amino acids.
<220> FEATURE:
<221> NAME/KEY: MISC_FEATURE
<222> LOCATION: (35)..(48)
<223> OTHER INFORMATION: framework 2
<220> FEATURE:
<221> NAME/KEY: MISC_FEATURE
<222> LOCATION: (49)..(49)
<223> OTHER INFORMATION: complementarity determinng region 2 (CDR2), Xaa
      is any amino acids.
<220> FEATURE:
<221> NAME/KEY: MISC_FEATURE
<222> LOCATION: (50)..(81)
<223> OTHER INFORMATION: framework 3
<220> FEATURE:
<221> NAME/KEY: MISC_FEATURE
<222> LOCATION: (82)..(82)
<223> OTHER INFORMATION: complementarity determinng region 3 (CDR3), Xaa
      is any amino acids.
<220> FEATURE:
<221> NAME/KEY: MISC_FEATURE
<222> LOCATION: (83)..(108)
<223> OTHER INFORMATION: framework 4

<400> SEQUENCE: 52
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
            20                  25                  30

Ser Xaa Trp Ile Arg Gln Pro Pro Gly Lys Gly Leu Glu Trp Ile Gly
        35                  40                  45

Xaa Arg Val Thr Ile Ser Val Asp Thr Ser Lys Asn Gln Phe Ser Leu
50                  55                  60

Lys Leu Ser Ser Val Thr Ala Ala Asp Thr Ala Val Tyr Tyr Cys Ala
65                  70                  75                  80

Arg Xaa Trp Gly Gln Gly Thr Leu Val Thr Asn Ser Ser Ala Pro Thr
            85                  90                  95

Lys Ala Pro Asp Val Phe Pro Ile Ile Ser Gly Cys
            100                 105
```

```
<210> SEQ ID NO 53
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: Vh5 heavy chain variable region
<220> FEATURE:
<221> NAME/KEY: MISC_FEATURE
<222> LOCATION: (1)..(31)
<223> OTHER INFORMATION: MISC_FEATURE
<220> FEATURE:
<221> NAME/KEY: MISC_FEATURE
<222> LOCATION: (32)..(32)
<223> OTHER INFORMATION: complementarity determinng region 1 (CDR1), Xaa
      is any amino acids.
<220> FEATURE:
<221> NAME/KEY: MISC_FEATURE
<222> LOCATION: (33)..(46)
<223> OTHER INFORMATION: framework 2
<220> FEATURE:
<221> NAME/KEY: MISC_FEATURE
<222> LOCATION: (47)..(47)
<223> OTHER INFORMATION: complementarity determinng region 2 (CDR2), Xaa
      is any amino acids.
<220> FEATURE:
<221> NAME/KEY: MISC_FEATURE
<222> LOCATION: (48)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), Xaa
      is any amino acids.
<220> FEATURE:
<221> NAME/KEY: MISC_FEATURE
<222> LOCATION: (81)..(132)
<223> OTHER INFORMATION: framework 4

<400> SEQUENCE: 53

Glu Glu Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Xaa
            20                  25                  30

Trp Val Arg Gln Met Pro Gly Lys Gly Leu Glu Trp Met Gly Xaa Gln
        35                  40                  45

Val Thr Ile Ser Ala Asp Lys Ser Ile Ser Thr Ala Tyr Leu Gln Trp
50                  55                  60

Ser Ser Leu Lys Ala Ser Asp Thr Ala Met Tyr Tyr Cys Ala Arg Xaa
65                  70                  75                  80
```

```
Trp Gly Gln Gly Thr Leu Val Thr Asn Ser Ser Ala Ser Thr Lys Ala
                85                  90                  95

Pro Ser Val Phe Pro Leu Val Ser Cys Glu Asn Ser Pro Ser Asp Thr
            100                 105                 110

Ser Ser Val Ala Val Gly Cys Leu Ala Gln Asp Phe Leu Pro Asp Ser
            115                 120                 125

Ile Thr Phe Ser
        130

<210> SEQ ID NO 54
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: Vh6 heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), Xaa
      is any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), Xaa
      is any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), Xaa
      is any amino acids.
<220> FEATURE:
<221> NAME/KEY: MISC_FEATURE
<222> LOCATION: (80)..(125)
<223> OTHER INFORMATION: framework 4

<400> SEQUENCE: 54

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Xaa Trp
            20                  25                  30

Ile Arg Gln Ser Pro Ser Arg Gly Leu Glu Trp Leu Gly Xaa Arg Ile
        35                  40                  45

Thr Ile Asn Pro Asp Thr Ser Lys Asn Gln Phe Ser Leu Gln Leu Asn
    50                  55                  60

Ser Val Thr Pro Glu Asp Thr Ala Val Tyr Tyr Cys Ala Arg Xaa Trp
65                  70                  75                  80

Gly Gln Gly Thr Leu Val Thr Asn Ser Ser Gly Ser Ala Ser Ala Pro
                85                  90                  95

Thr Leu Phe Pro Leu Val Ser Cys Glu Asn Ser Pro Ser Asp Thr Ser
            100                 105                 110

Ser Val Ala Val Gly Cys Leu Ala Gln Asp Phe Leu Pro
            115                 120                 125
```

```
<210> SEQ ID NO 55
<211> LENGTH: 91
<212> TYPE: PRT
<213> ORGANISM: Homo sapiens
<220> FEATURE:
<221> NAME/KEY: MISC_FEATURE
<222> LOCATION: (1)..(91)
<223> OTHER INFORMATION: Vh7 heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), Xaa
      is any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), Xaa
      is any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), Xaa
      is any amino acids.
<220> FEATURE:
<221> NAME/KEY: MISC_FEATURE
<222> LOCATION: (80)..(91)
<223> OTHER INFORMATION: framework 4

<400> SEQUENCE: 55

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Xaa Trp
                20                  25                  30

Val Arg Gln Ala Pro Gly Gln Gly Leu Glu Trp Met Gly Xaa Arg Phe
            35                  40                  45

Val Phe Ser Leu Asp Thr Ser Val Ser Thr Ala Tyr Leu Gln Ile Ser
        50                  55                  60

Ser Leu Lys Ala Glu Asp Thr Ala Val Tyr Tyr Cys Ala Arg Xaa Trp
65                  70                  75                  80

Gly Gln Gly Thr Leu Val Thr Asn Ser Ser Ser
                85                  90

<210> SEQ ID NO 56
<211> LENGTH: 354
<212> TYPE: PRT
<213> ORGANISM: Homo sapiens
<220> FEATURE:
<221> NAME/KEY: MISC_FEATURE
<222> LOCATION: (1)..(354)
<223> OTHER INFORMATION: IgA1 heavy chain constant region
<220> FEATURE:
<221> NAME/KEY: MISC_FEATURE
<222> LOCATION: (1)..(102)
<223> OTHER INFORMATION: CH1
<220> FEATURE:
<221> NAME/KEY: MISC_FEATURE
<222> LOCATION: (103)..(121)
<223> OTHER INFORMATION: hinge
<220> FEATURE:
```

```
<221> NAME/KEY: MISC_FEATURE
<222> LOCATION: (122)..(222)
<223> OTHER INFORMATION: CH2
<220> FEATURE:
<221> NAME/KEY: MISC_FEATURE
<222> LOCATION: (223)..(354)
<223> OTHER INFORMATION: CH3

<400> SEQUENCE: 56
```

| | | | | | | | | | | | | | | | |
|---|---|---|---|---|---|---|---|---|---|---|---|---|---|---|---|
| Ala | Ser | Pro | Thr | Ser | Pro | Lys | Val | Phe | Pro | Leu | Ser | Leu | Cys | Ser | Thr |
| 1 | | | | 5 | | | | | 10 | | | | | 15 | |
| Gln | Pro | Asp | Gly | Asn | Val | Val | Ile | Ala | Cys | Leu | Val | Gln | Gly | Phe | Phe |
| | | | 20 | | | | | 25 | | | | | 30 | | |
| Pro | Gln | Glu | Pro | Leu | Ser | Val | Thr | Trp | Ser | Glu | Ser | Gly | Gln | Gly | Val |
| | | 35 | | | | | 40 | | | | | 45 | | | |
| Thr | Ala | Arg | Asn | Phe | Pro | Pro | Ser | Gln | Asp | Ala | Ser | Gly | Asp | Leu | Tyr |
| | 50 | | | | | 55 | | | | | 60 | | | | |
| Thr | Thr | Ser | Ser | Gln | Leu | Thr | Leu | Pro | Ala | Thr | Gln | Cys | Leu | Ala | Gly |
| 65 | | | | | 70 | | | | | 75 | | | | | 80 |
| Lys | Ser | Val | Thr | Cys | His | Val | Lys | His | Tyr | Thr | Asn | Pro | Ser | Gln | Asp |
| | | | | 85 | | | | | 90 | | | | | 95 | |
| Val | Thr | Val | Pro | Cys | Pro | Asn | Pro | Ser | Thr | Pro | Pro | Thr | Pro | Ser | Pro |
| | | | 100 | | | | | 105 | | | | | 110 | | |
| Ser | Thr | Pro | Pro | Thr | Pro | Ser | Pro | Ser | Cys | Cys | His | Pro | Arg | Leu | Ser |
| | | 115 | | | | | 120 | | | | | 125 | | | |
| Leu | His | Arg | Pro | Ala | Leu | Glu | Asp | Leu | Leu | Leu | Gly | Ser | Glu | Ala | Asn |
| | 130 | | | | | 135 | | | | | 140 | | | | |
| Leu | Thr | Cys | Thr | Leu | Thr | Gly | Leu | Arg | Asp | Ala | Ser | Gly | Val | Thr | Phe |
| 145 | | | | | 150 | | | | | 155 | | | | | 160 |
| Thr | Trp | Thr | Pro | Ser | Ser | Gly | Lys | Ser | Ala | Val | Gln | Gly | Pro | Pro | Glu |
| | | | | 165 | | | | | 170 | | | | | 175 | |
| Arg | Asp | Leu | Cys | Gly | Cys | Tyr | Ser | Asn | Ser | Ser | Val | Leu | Pro | Gly | Cys |
| | | | 180 | | | | | 185 | | | | | 190 | | |
| Ala | Glu | Pro | Trp | Asn | His | Gly | Lys | Thr | Phe | Thr | Cys | Thr | Ala | Ala | Tyr |
| | | 195 | | | | | 200 | | | | | 205 | | | |
| Pro | Glu | Ser | Lys | Thr | Pro | Leu | Thr | Ala | Thr | Leu | Ser | Lys | Ser | Gly | Asn |
| | 210 | | | | | 215 | | | | | 220 | | | | |
| Thr | Phe | Arg | Pro | Glu | Val | His | Leu | Leu | Pro | Pro | Pro | Ser | Glx | Glu | Glu |
| 225 | | | | | 230 | | | | | 235 | | | | | 240 |
| Leu | Ala | Leu | Asn | Glu | Leu | Val | Thr | Leu | Thr | Cys | Leu | Ala | Arg | Gly | Phe |
| | | | | 245 | | | | | 250 | | | | | 255 | |
| Ser | Pro | Lys | Asp | Val | Leu | Val | Arg | Trp | Leu | Gln | Gly | Ser | Gln | Glu | Leu |
| | | | 260 | | | | | 265 | | | | | 270 | | |
| Pro | Arg | Glu | Lys | Tyr | Leu | Thr | Trp | Ala | Ser | Arg | Gln | Glu | Pro | Ser | Gln |
| | | 275 | | | | | 280 | | | | | 285 | | | |
| Gly | Thr | Thr | Thr | Phe | Ala | Val | Thr | Ser | Ile | Leu | Arg | Val | Ala | Ala | Glu |
| | 290 | | | | | 295 | | | | | 300 | | | | |
| Asp | Trp | Lys | Lys | Gly | Asp | Thr | Phe | Ser | Cys | Met | Val | Gly | His | Glu | Ala |
| 305 | | | | | 310 | | | | | 315 | | | | | 320 |
| Leu | Pro | Leu | Ala | Phe | Thr | Gln | Lys | Thr | Ile | Asp | Arg | Leu | Ala | Gly | Lys |
| | | | | 325 | | | | | 330 | | | | | 335 | |
| Pro | Thr | His | Val | Asn | Val | Ser | Val | Val | Met | Ala | Glu | Val | Asp | Gly | Thr |
| | | | 340 | | | | | 345 | | | | | 350 | | |
| Cys | Tyr | | | | | | | | | | | | | | |

```
<210> SEQ ID NO 57
<211> LENGTH: 340
<212> TYPE: PRT
<213> ORGANISM: Homo sapiens
<220> FEATURE:
<221> NAME/KEY: MISC_FEATURE
<222> LOCATION: (1)..(340)
<223> OTHER INFORMATION: IgA2 heavy chain constant region
<220> FEATURE:
<221> NAME/KEY: MISC_FEATURE
<222> LOCATION: (1)..(102)
<223> OTHER INFORMATION: CH1
<220> FEATURE:
<221> NAME/KEY: MISC_FEATURE
<222> LOCATION: (103)..(108)
<223> OTHER INFORMATION: hinge
<220> FEATURE:
<221> NAME/KEY: MISC_FEATURE
<222> LOCATION: (109)..(209)
<223> OTHER INFORMATION: CH2
<220> FEATURE:
<221> NAME/KEY: MISC_FEATURE
<222> LOCATION: (210)..(340)
<223> OTHER INFORMATION: CH3
```

<400> SEQUENCE: 57

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala

```
                     275                 280                 285
Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                    325                 330                 335

Gly Thr Cys Tyr
            340

<210> SEQ ID NO 58
<211> LENGTH: 384
<212> TYPE: PRT
<213> ORGANISM: Homo sapiens
<220> FEATURE:
<221> NAME/KEY: MISC_FEATURE
<222> LOCATION: (1)..(384)
<223> OTHER INFORMATION: IgD heavy chain constant region
<220> FEATURE:
<221> NAME/KEY: MISC_FEATURE
<222> LOCATION: (1)..(101)
<223> OTHER INFORMATION: CH1
<220> FEATURE:
<221> NAME/KEY: MISC_FEATURE
<222> LOCATION: (102)..(135)
<223> OTHER INFORMATION: hinge 1
<220> FEATURE:
<221> NAME/KEY: MISC_FEATURE
<222> LOCATION: (136)..(159)
<223> OTHER INFORMATION: hinge 2
<220> FEATURE:
<221> NAME/KEY: MISC_FEATURE
<222> LOCATION: (160)..(267)
<223> OTHER INFORMATION: CH2
<220> FEATURE:
<221> NAME/KEY: MISC_FEATURE
<222> LOCATION: (268)..(384)
<223> OTHER INFORMATION: CH3

<400> SEQUENCE: 58

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175
```

```
Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
        290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Arg Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
        370                 375                 380
```

<210> SEQ ID NO 59
<211> LENGTH: 497
<212> TYPE: PRT
<213> ORGANISM: Homo sapiens
<220> FEATURE:
<221> NAME/KEY: MISC_FEATURE
<222> LOCATION: (1)..(497)
<223> OTHER INFORMATION: IgE heavy chain constant region
<220> FEATURE:
<221> NAME/KEY: MISC_FEATURE
<222> LOCATION: (1)..(103)
<223> OTHER INFORMATION: CH1
<220> FEATURE:
<221> NAME/KEY: MISC_FEATURE
<222> LOCATION: (104)..(210)
<223> OTHER INFORMATION: CH2
<220> FEATURE:
<221> NAME/KEY: MISC_FEATURE
<222> LOCATION: (211)..(318)
<223> OTHER INFORMATION: CH3
<220> FEATURE:
<221> NAME/KEY: MISC_FEATURE
<222> LOCATION: (319)..(497)
<223> OTHER INFORMATION: CH4

<400> SEQUENCE: 59

```
Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60
```

-continued

```
His Tyr Ala Thr Ile Ser Leu Leu Thr Val Ser Gly Ala Trp Ala Lys
 65                  70                  75                  80

Gln Met Phe Thr Cys Arg Val Ala His Thr Pro Ser Ser Thr Asp Trp
                 85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly His Phe Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Val Gly Pro Arg Ala Ala Pro Glu Val Tyr Ala Phe Ala Thr Pro Glu
                325                 330                 335

Trp Pro Gly Ser Arg Asp Lys Arg Thr Leu Ala Cys Leu Ile Gln Asn
            340                 345                 350

Phe Met Pro Glu Asp Ile Ser Val Gln Trp Leu His Asn Glu Val Gln
        355                 360                 365

Leu Pro Asp Ala Arg His Ser Thr Thr Gln Pro Arg Lys Thr Lys Gly
    370                 375                 380

Ser Gly Phe Phe Val Phe Ser Arg Leu Glu Val Thr Arg Ala Glu Trp
385                 390                 395                 400

Glu Gln Lys Asp Glu Phe Ile Cys Arg Ala Val His Glu Ala Ala Ser
                405                 410                 415

Pro Ser Gln Thr Val Gln Arg Ala Val Ser Val Asn Pro Gly Lys Asp
            420                 425                 430

Val Cys Val Glu Glu Ala Glu Gly Glu Ala Pro Trp Thr Trp Thr Gly
        435                 440                 445

Leu Cys Ile Phe Ala Ala Leu Phe Leu Leu Ser Val Ser Tyr Ser Ala
    450                 455                 460

Ala Leu Thr Leu Leu Met Val Gln Arg Phe Leu Ser Ala Thr Arg Gln
465                 470                 475                 480

Gly Arg Pro Gln Thr Ser Leu Asp Tyr Thr Asn Val Leu Gln Pro His
```

-continued

```
                485                 490                 495
Ala
```

<210> SEQ ID NO 60
<211> LENGTH: 339
<212> TYPE: PRT
<213> ORGANISM: Homo sapiens
<220> FEATURE:
<221> NAME/KEY: MISC_FEATURE
<222> LOCATION: (1)..(339)
<223> OTHER INFORMATION: IgG1 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(113)
<223> OTHER INFORMATION: hinge
<220> FEATURE:
<221> NAME/KEY: MISC_FEATURE
<222> LOCATION: (114)..(223)
<223> OTHER INFORMATION: CH2
<220> FEATURE:
<221> NAME/KEY: MISC_FEATURE
<222> LOCATION: (224)..(339)
<223> OTHER INFORMATION: CH3

<400> SEQUENCE: 60

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Asn Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

-continued

Pro Ser Asp Ile Ala Val Glu Trp Glu Ser Asx Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys Thr His Thr Cys Pro
            325                 330                 335

Pro Cys Pro

<210> SEQ ID NO 61
<211> LENGTH: 326
<212> TYPE: PRT
<213> ORGANISM: Homo sapiens
<220> FEATURE:
<221> NAME/KEY: MISC_FEATURE
<222> LOCATION: (1)..(326)
<223> OTHER INFORMATION: IgG2 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(110)
<223> OTHER INFORMATION: hinge
<220> FEATURE:
<221> NAME/KEY: MISC_FEATURE
<222> LOCATION: (111)..(219)
<223> OTHER INFORMATION: CH2
<220> FEATURE:
<221> NAME/KEY: MISC_FEATURE
<222> LOCATION: (220)..(326)
<223> OTHER INFORMATION: CH3

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

```
Ser Thr Phe Arg Asn Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 62
<211> LENGTH: 377
<212> TYPE: PRT
<213> ORGANISM: Homo sapiens
<220> FEATURE:
<221> NAME/KEY: MISC_FEATURE
<222> LOCATION: (1)..(377)
<223> OTHER INFORMATION: IgG3 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(115)
<223> OTHER INFORMATION: hinge 1
<220> FEATURE:
<221> NAME/KEY: MISC_FEATURE
<222> LOCATION: (116)..(130)
<223> OTHER INFORMATION: hinge 2
<220> FEATURE:
<221> NAME/KEY: MISC_FEATURE
<222> LOCATION: (131)..(145)
<223> OTHER INFORMATION: hinge 3
<220> FEATURE:
<221> NAME/KEY: MISC_FEATURE
<222> LOCATION: (146)..(160)
<223> OTHER INFORMATION: hinge 4
<220> FEATURE:
<221> NAME/KEY: MISC_FEATURE
<222> LOCATION: (161)..(270)
<223> OTHER INFORMATION: CH2
<220> FEATURE:
<221> NAME/KEY: MISC_FEATURE
<222> LOCATION: (271)..(377)
<223> OTHER INFORMATION: CH3

<400> SEQUENCE: 62

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
             85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Asn Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 63
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: IgG4 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(110)
```

```
<223> OTHER INFORMATION: hinge
<220> FEATURE:
<221> NAME/KEY: MISC_FEATURE
<222> LOCATION: (111)..(220)
<223> OTHER INFORMATION: CH2
<220> FEATURE:
<221> NAME/KEY: MISC_FEATURE
<222> LOCATION: (221)..(327)
<223> OTHER INFORMATION: CH3

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Asn Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 64
<211> LENGTH: 476
<212> TYPE: PRT
```

```
<213> ORGANISM: Homo sapiens
<220> FEATURE:
<221> NAME/KEY: MISC_FEATURE
<222> LOCATION: (1)..(476)
<223> OTHER INFORMATION: IgM heavy chain constant region
<220> FEATURE:
<221> NAME/KEY: MISC_FEATURE
<222> LOCATION: (1)..(104)
<223> OTHER INFORMATION: CH1
<220> FEATURE:
<221> NAME/KEY: MISC_FEATURE
<222> LOCATION: (105)..(217)
<223> OTHER INFORMATION: CH2
<220> FEATURE:
<221> NAME/KEY: MISC_FEATURE
<222> LOCATION: (218)..(323)
<223> OTHER INFORMATION: CH3
<220> FEATURE:
<221> NAME/KEY: MISC_FEATURE
<222> LOCATION: (324)..(476)
<223> OTHER INFORMATION: CH4

<400> SEQUENCE: 64

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Ser Lys Ser Lys Leu Ile Cys Gln Ala Thr Gly Phe Ser Pro Arg Gln
        130                 135                 140

Ile Gln Val Ser Trp Leu Arg Glu Gly Lys Gln Asn Gly Ser Gly Val
145                 150                 155                 160

Thr Thr Asp Gln Val Gln Ala Glu Ala Lys Glu Ser Gly Pro Thr Thr
                165                 170                 175

Tyr Lys Val Thr Ser Thr Leu Thr Ile Lys Glu Ser Asp Trp Leu Ser
                180                 185                 190

Gln Ser Met Phe Thr Cys Arg Val Asp His Arg Gly Leu Thr Phe Gln
            195                 200                 205

Gln Asn Ala Ser Ser Met Cys Val Pro Asp Gln Asp Thr Ala Ile Arg
        210                 215                 220

Val Phe Ala Ile Pro Pro Ser Phe Ala Ser Ile Phe Leu Thr Lys Ser
225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
                260                 265                 270

Asn Ile Ser Glu Ser His Pro Asn Ala Thr Phe Ser Ala Val Gly Glu
            275                 280                 285

Ala Ser Ile Cys Glu Asp Asp Trp Asn Ser Gly Glu Arg Phe Thr Cys
```

-continued

```
                290                 295                 300
Thr Val Thr His Thr Asp Leu Pro Ser Pro Leu Lys Gln Thr Ile Ser
305                 310                 315                 320

Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
            340                 345                 350

Leu Val Thr Gly Phe Ser Pro Ala Asp Val Phe Val Gln Trp Met
        355                 360                 365

Gln Arg Gly Gln Pro Leu Ser Pro Glu Lys Tyr Val Thr Ser Ala Pro
370                 375                 380

Met Pro Glu Pro Gln Ala Pro Gly Arg Tyr Phe Ala His Ser Ile Leu
385                 390                 395                 400

Thr Val Ser Glu Glu Trp Asn Thr Gly Glu Thr Tyr Thr Cys Val
                405                 410                 415

Val Ala His Glu Ala Leu Pro Asn Arg Val Thr Glu Arg Thr Val Asp
            420                 425                 430

Lys Ser Thr Gly Lys Pro Thr Ser Ala Asp Glu Glu Gly Phe Glu Asn
        435                 440                 445

Leu Trp Ala Thr Ala Ser Thr Phe Ile Val Leu Tyr Asn Val Ser Leu
450                 455                 460

Val Met Ser Asp Thr Ala Gly Thr Cys Tyr Val Lys
465                 470                 475

<210> SEQ ID NO 65
<211> LENGTH: 8
<212> TYPE: PRT
<213> ORGANISM: Homo sapiens

<400> SEQUENCE: 65

Gly Gly Gly Lys Gly Gly Gly Gly
1               5

<210> SEQ ID NO 66
<211> LENGTH: 8
<212> TYPE: PRT
<213> ORGANISM: Homo sapiens

<400> SEQUENCE: 66

Gly Gly Gly Asn Gly Ser Gly Gly
1               5

<210> SEQ ID NO 67
<211> LENGTH: 8
<212> TYPE: PRT
<213> ORGANISM: Homo sapiens

<400> SEQUENCE: 67

Gly Gly Gly Cys Gly Gly Gly Gly
1               5

<210> SEQ ID NO 68
<211> LENGTH: 5
<212> TYPE: PRT
<213> ORGANISM: Homo sapiens

<400> SEQUENCE: 68

Gly Pro Asn Gly Gly
1               5
```

<210> SEQ ID NO 69
<211> LENGTH: 297
<212> TYPE: PRT
<213> ORGANISM: Homo sapiens

<400> SEQUENCE: 69

Met Ala Trp Val Trp Thr Leu Leu Phe Leu Met Ala Ala Gln Ser
1               5                   10                  15

Ile Gln Ala His Ala Glu Gly Thr Phe Thr Ser Asp Val Ser Ser Tyr
                20                  25                  30

Leu Glu Gly Gln Ala Ala Lys Glu Phe Ile Ala Trp Leu Val Lys Gly
            35                  40                  45

Arg Gly Gly Gly Ser Gly Gly Ser Gly Thr Leu Val Thr Val Ser
        50                  55                  60

Ser Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
                100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
        130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
                180                 185                 190

Pro Arg Glu Pro Gln Val Tyr Thr Leu Pro Pro Ser Arg Asp Glu Leu
            195                 200                 205

Thr Lys Asn Gln Val Ser Leu Thr Cys Leu Val Lys Gly Phe Tyr Pro
        210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 70
<211> LENGTH: 894
<212> TYPE: DNA
<213> ORGANISM: Homo sapiens

<400> SEQUENCE: 70
atggcttggg tgtggacctt gctattcctg atggcggccg cccaaagtat acaggcccat    60
gctgaaggga cctttactag tgatgtaagt tcttatttgg aaggccaagc tgccaaggaa    120
ttcattgctt ggctggtgaa aggccgagga ggtggatccg gtggaggctc cggtacctta    180

-continued

```
gtcaccgtct cctcagagcc caaatcttgt gacaaaactc acacgtgccc accgtgccca      240
gcacctgaac tcctggggg  accgtcagtc ttcctcttcc ccccaaaacc caaggacacc      300
ctcatgatct cccggacccc tgaggtcaca tgcgtggtgg tggacgtgag ccacgaagac      360
cctgaggtca agttcaactg gtacgtggac ggcgtggagg tgcataatgc caagacaaag      420
ccgcgggagg agcagtacaa cagcacgtac cgggtggtca gcgtcctcac cgtcctgcac      480
caggactggc tgaatggcaa ggagtacaag tgcaaggtct ccaacaaagc cctcccagcc      540
cccatcgaga aaaccatctc caaagccaaa gggcagcccc gagaaccaca ggtgtacacc      600
ctgcccccat cccgggatga gctgaccaag aaccaggtca gcctgacctg cctggtcaaa      660
ggcttctatc ccagcgacat cgccgtggag tgggagagca atgggcagcc ggagaacaac      720
tacaagacca cgcctcccgt gctggactcc gacggctcct tcttcctcta cagcaagctc      780
accgtggaca gagcaggtg  gcagcagggg aacgtcttct catgctccgt gatgcatgag      840
gctctgcaca accactacac gcagaagagc ctctccctgt ctccgggtaa atga           894
```